(12) United States Patent
Nana et al.

(10) Patent No.: US 11,911,769 B2
(45) Date of Patent: Feb. 27, 2024

(54) NUCLEIC ACID AMPLIFICATION AND DETECTION DEVICES, SYSTEMS AND METHODS

(71) Applicant: Abbott Laboratories, Abbott Park, IL (US)

(72) Inventors: Sonal Sadaria Nana, Chicago, IL (US); Eric B. Shain, Glencoe, IL (US); Michael S. Hazell, Cambridge (GB); Eric D. Yeaton, Abbott Park, IL (US); Michael Giraud, Abbott Park, IL (US); Timothy J. Patno, Barrington, IL (US); Ali Attarwalla, Mount Prospect, IL (US); Dean Khan, Forest Park, IL (US); Matthew J. Hayes, Cambridge (GB)

(73) Assignee: Abbott Laboratories, Abbott Park, IL (US)

( * ) Notice: Subject to any disclaimer, the term of this patent is extended or adjusted under 35 U.S.C. 154(b) by 537 days.

(21) Appl. No.: 17/039,106

(22) Filed: Sep. 30, 2020

(65) Prior Publication Data

US 2021/0121888 A1    Apr. 29, 2021

Related U.S. Application Data

(63) Continuation of application No. 15/460,109, filed on Mar. 15, 2017, now abandoned.
(Continued)

(51) Int. Cl.
*G01N 33/48* (2006.01)
*G01N 33/50* (2006.01)
(Continued)

(52) U.S. Cl.
CPC ........... *B01L 7/52* (2013.01); *B01L 2200/147* (2013.01); *B01L 2300/0609* (2013.01);
(Continued)

(58) Field of Classification Search
CPC ......... B01L 2300/0654; B01L 2300/12; B01L 2300/16; G01N 21/93; G01N 30/74; G01N 30/8624
See application file for complete search history.

(56) References Cited

U.S. PATENT DOCUMENTS 8,329,453 B2    12/2012    Battrell et al.
8,349,564 B2    1/2013    Macioszek et al.
(Continued)

FOREIGN PATENT DOCUMENTS

| WO | 2006/052682 | 5/2006 |
|---|---|---|
| WO | 2017/160979 | 9/2017 |
| WO | 2017/161058 | 9/2017 |

OTHER PUBLICATIONS

Balandin (2011) "Thermal properties of graphene and nanostructured carbon materials" Nat Mater 10:569-581.
(Continued)

*Primary Examiner* — Russell S Negin
(74) *Attorney, Agent, or Firm* — Edward J. Baba; Mandar A. Joshi; Bozicevic, Field & Francis LLP

(57) ABSTRACT

The instant disclosure provides nucleic acid amplification systems and multi-reaction analysis systems useful in the efficient processing of samples, including clinical samples. Integrated systems that include nucleic acid amplification devices functionally combined with multi-reaction analysis systems are also included. Also provided are methods for monitoring multiple concurrent nucleic acid amplification reactions that include the use of devices and systems described herein.

17 Claims, 22 Drawing Sheets

Related U.S. Application Data

(60) Provisional application No. 62/308,632, filed on Mar. 15, 2016.

(51) Int. Cl.
*B01L 7/00* (2006.01)
*G01N 21/93* (2006.01)
*G01N 30/74* (2006.01)
*G01N 30/86* (2006.01)

(52) U.S. Cl.
CPC .............. *B01L 2300/0645* (2013.01); *B01L 2300/0654* (2013.01); *B01L 2300/12* (2013.01); *B01L 2300/16* (2013.01); *B01L 2300/1822* (2013.01); *B01L 2300/1894* (2013.01); *C12Q 2563/103* (2013.01); *C12Q 2563/107* (2013.01); *C12Q 2565/60* (2013.01); *G01N 21/93* (2013.01); *G01N 30/74* (2013.01); *G01N 30/8624* (2013.01)

(56) References Cited

U.S. PATENT DOCUMENTS

| | | |
|---|---|---|
| 8,840,848 B2 | 9/2014 | Kraihanzel |
| 9,089,828 B2 | 7/2015 | Howell et al. |
| 2002/0072112 A1 | 6/2002 | Atwood et al. |
| 2003/0157523 A1 | 8/2003 | Frantz et al. |
| 2004/0135578 A1* | 7/2004 | Peters .............. G01R 33/56554 324/309 |
| 2005/0153430 A1 | 7/2005 | Ohtaka |
| 2013/0137110 A1* | 5/2013 | Kraihanzel ............. G01F 23/24 435/6.12 |
| 2014/0005078 A1* | 1/2014 | Howell ................ G01N 21/253 506/39 |
| 2017/0022502 A1 | 1/2017 | Dickson et al. |
| 2017/0022603 A1 | 1/2017 | Ivanov et al. |

OTHER PUBLICATIONS

Dasgupta and Agarwal (1992) "Orthotropic thermal conductivity of plain-weave fabric composites using a homogenization technique" Journal of Composite Materials 26(18):2736-2758.

Sweeting and Liu (2004) "Measurement of thermal conductivity for fibre-reinforced composites" Composites Part A: applied science and manufacturing 35(7):933-938.

Wetherhold and Wang (1994) "Difficulties in the theories for predicting transverse thermal conductivity of continuous fiber composites" Journal of composite materials 28(15):1491-1498.

* cited by examiner

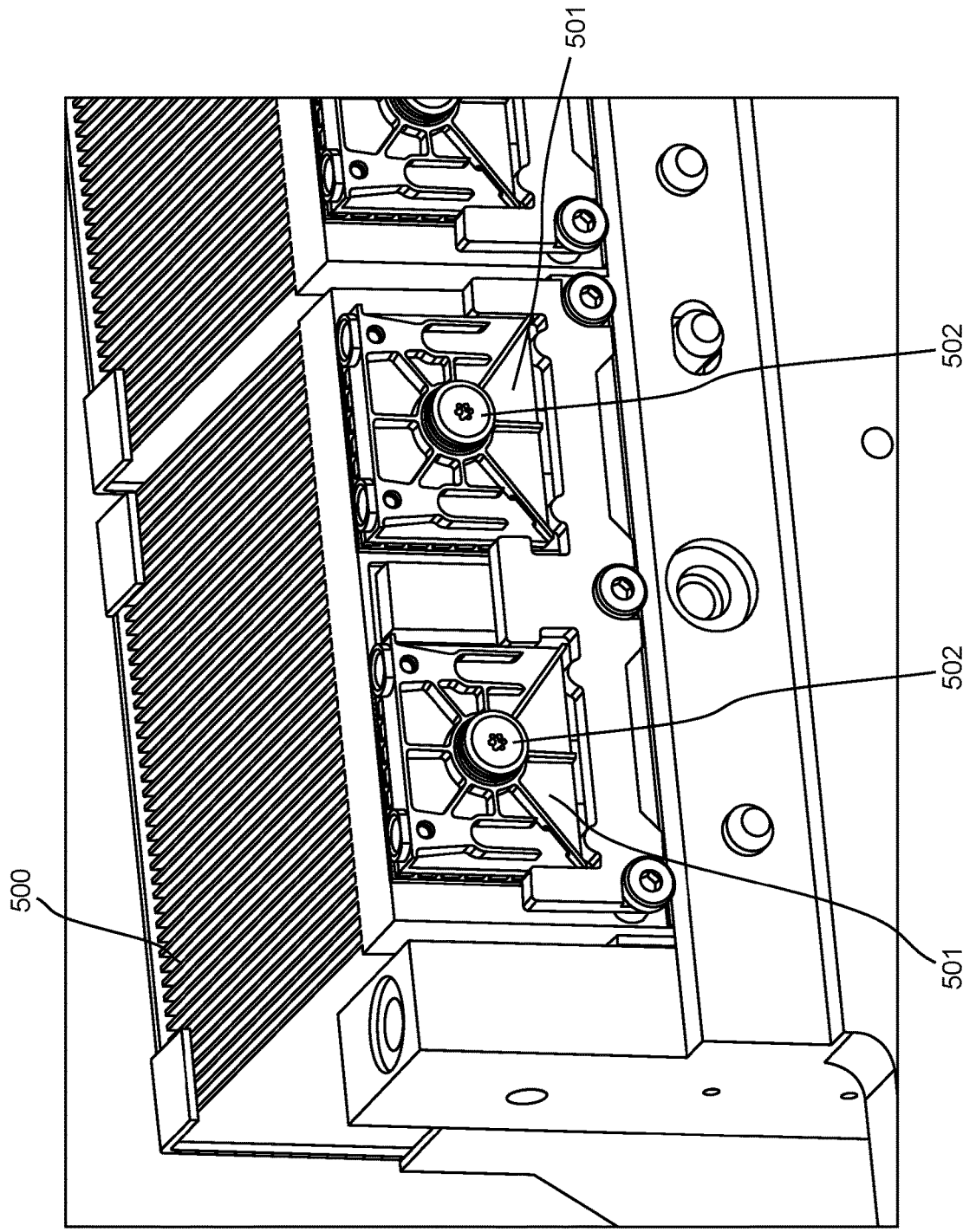

Amp Detect Functional Block Diagram

FIG. 16
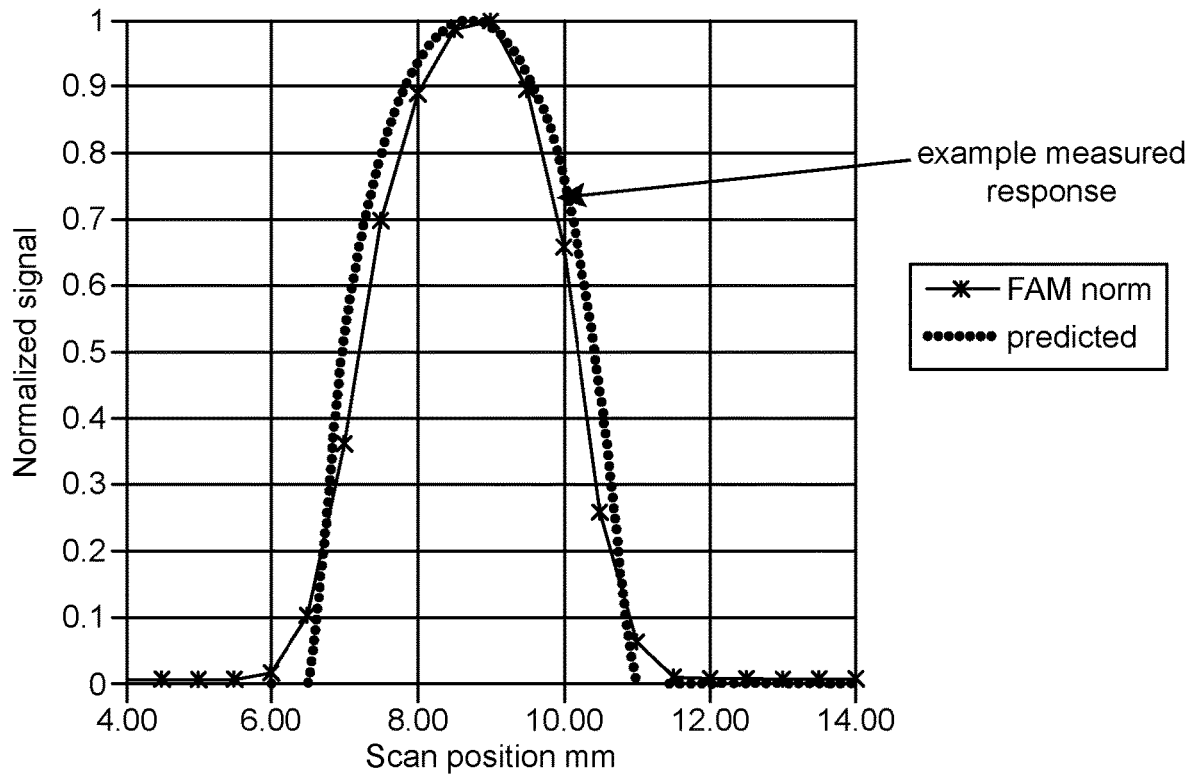
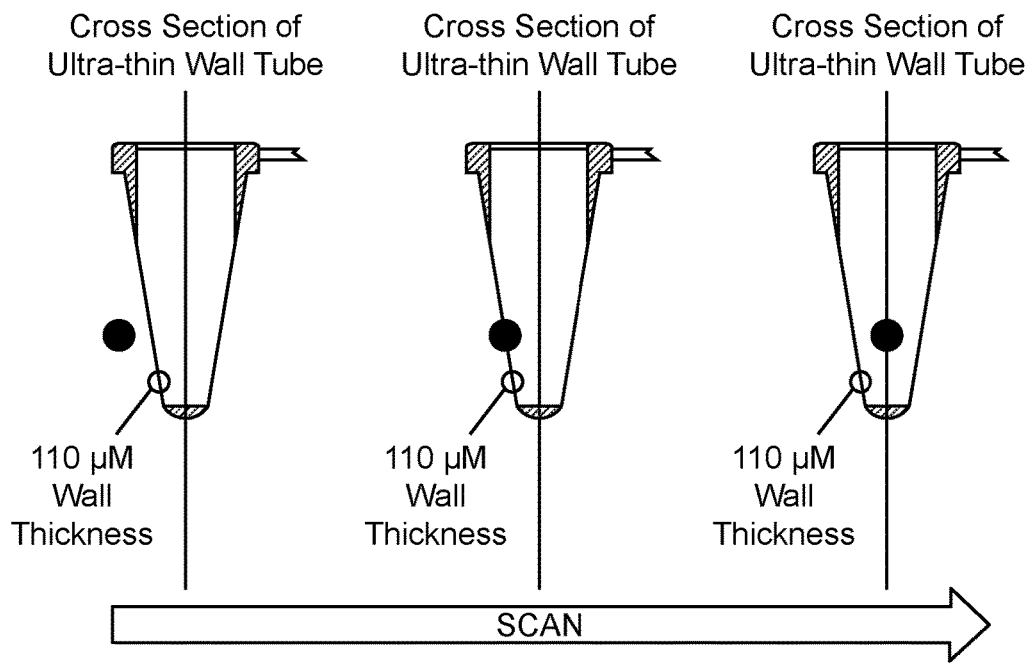

NUCLEIC ACID AMPLIFICATION AND DETECTION DEVICES, SYSTEMS AND METHODS

CROSS-REFERENCE TO RELATED APPLICATIONS

Pursuant to 35 U.S.C. § 119(e), this application claims priority to the filing date of the U.S. Provisional Patent Application Ser. No. 62/308,632, filed Mar. 15, 2016, the disclosure of which application is herein incorporated by reference.

BACKGROUND

The majority of clinical decisions are based on laboratory and health test data. An increasing variety of tests and a demand for clinical laboratories to process a greater volume of samples creates strain on testing facilities, personnel and equipment. In addition, health care testing needs are unpredictable on a day-to-day and even hour-to-hour basis making the efficient scheduling of test sample processing a challenging endeavor. In addition, the frequent occurrence of tests requiring rush or STAT processing in the clinical setting adds additional difficulties and can result in inefficient testing resource allocation.

Clinical testing facilities utilizing nucleic acid amplification based methods are not immune to such pressures. On the contrary the variety of nucleic acid based diagnostic tests is growing and demand from clinicians and patients for such tests is also expanding. There is a burden on clinical testing facilities to efficiently perform a wider range of different nucleic acid amplification based tests while maintaining the versatility to process rush samples out of order when they unexpectedly arrive.

SUMMARY

Aspects of the instant disclosure include nucleic acid amplification systems, thermal blocks for use therein, multi-reaction analysis systems useful in the efficient processing of samples, integrated systems that include nucleic acid amplification devices functionally combined with multi-reaction analysis systems and methods for monitoring multiple concurrent nucleic acid amplification reactions that include the use of such devices and systems.

Aspects of the instant disclosure include a thermal block for simultaneous nucleic acid amplification and reaction analysis; the thermal block comprising: a) two or more reaction vessel wells, each well comprising: i) a top opening configured to receive a reaction vessel inserted vertically into the well; ii) a side aperture configured to allow light to pass laterally into the reaction vessel well, wherein upon insertion of a reaction vessel into the well a majority of the sidewall of the reaction vessel is in thermal contact with the well and a portion of the sidewall is exposed to light by the aperture; b) a thermal transfer surface opposite the side apertures of the two reaction vessel wells; and c) a mounting hole positioned between the two reaction vessel wells and having a center axis perpendicular to the plane of the thermal transfer surface.

In some instances, aspects of the thermal block include where the block is bilaterally symmetrical along a vertical axis. In some instances, aspects of the thermal block include where the thermal transfer surface is essentially flat. In some instances, aspects of the thermal block include where the mounting hole is positioned equidistant from the two reaction vessels. In some instances, aspects of the thermal block include where the mounting hole is centrally positioned between the top and bottom sides of the thermal block. In some instances, aspects of the thermal block include where the mounting hole is centrally positioned between the right and left sides of the thermal block. In some instances, aspects of the thermal block include where the top surface of the thermal block comprises a raised flange encircling the circumference of each of the two reaction vessel wells. In some instances, aspects of the thermal block include where the surface of the thermal block opposite the thermal surface comprises a plurality of raised ridges, including where the plurality of raised ridges emanate radially from the mounting hole. In some instances, aspects of the thermal block include where the thermal block is constructed of aluminum. In some instances, aspects of the thermal block include where at least the two reaction vessel wells are nickel plated, at least a portion of the thermal block other than the two reaction vessel wells is nickel plated and/or the entire thermal block is nickel plated. In some instances, aspects of the thermal block include where the two reaction vessel wells comprise a lubrication coating, including wherein the lubrication coating is a dry lubrication coating. In some instances, aspects of the thermal block include a temperature detection area configured for the functional attachment of a temperature detector positioned proximally to each reaction vessel well, including where the temperature detection areas are positioned below the reaction vessel wells. In some instances, aspects of the thermal block include where each reaction vessel well further comprises a basal reservoir configured such that upon insertion of the reaction vessel into the well the reaction vessel does not contact the bottom of the well. In some instances, aspects of the thermal block include where the thermal block has a mass of 2 to 4 grams.

Aspects of the instant disclosure include a nucleic acid amplification module, the module comprising: a) a thermoelectric cooler unit comprising a mounting hole; b) a thermal block (e.g., as described above), wherein the thermal transfer surface is in thermal contact with a first surface of the thermoelectric cooler unit; and c) a heatsink configured to receive a mechanical fastener, wherein the heatsink is in thermal contact with a second surface of the thermoelectric cooler unit and the mounting holes are aligned such that the thermal block, thermoelectric cooler unit, and the heatsink are joined by a mechanical fastener positioned through the mounting holes and affixed to the heatsink.

In some instances, aspects of the nucleic acid amplification module include a conductive pad between the thermal block and the thermoelectric cooler unit or between the thermoelectric cooler unit and the heatsink, including wherein the conductive pad is a graphite pad. In some instances, aspects of the nucleic acid amplification module include where the module comprises conductive pads both between the thermal block and the thermoelectric cooler unit and between the thermoelectric cooler unit and the heatsink. In some instances, aspects of the nucleic acid amplification module include where the mechanical fastener joins the thermal block, thermoelectric cooler unit, and the heatsink by a compression force, including wherein the mechanical fastener is a compression screw. In some instances, aspects of the nucleic acid amplification module include where the compression force is between 100 and 200 pounds per square inch (psi). In some instances, aspects of the nucleic acid amplification module include where the thermal block and the thermoelectric cooler are supported by a support bar fastened to the heatsink. In some instances, aspects of the nucleic acid amplification module include a heatsink fan configured to force air past the heatsink, including wherein the heatsink is joined to the heatsink fan by a duct. In some instances, aspects of the nucleic acid amplification module include where the thermal block has an operating thermal slew rate of greater than 5° C. per second. In some instances, aspects of the nucleic acid amplification module include one or more resistance thermometers (RTDs) in thermal contact with the thermal block. In some instances, aspects of the nucleic acid amplification module include two RTDs in thermal contact with the thermal block, wherein each of the two RTDs are in proximity with a reaction vessel well of the thermal block. In some instances, aspects of the nucleic acid amplification module include an attached printed circuit board (PCB) for monitoring or controlling at least one electrical component of the module, including wherein the PCB is conformal coated. In some instances, aspects of the nucleic acid amplification module include at least one RTD in thermal contact with the thermal block and electrically connected to the PCB. In some instances, aspects of the nucleic acid amplification module include a RTD in thermal contact with the thermal block or the heatsink, wherein the RTD in thermal contact with the thermal block or the heatsink is configured to monitor the temperature of the thermal block or heatsink and trigger a cutoff of power to the thermal block or heatsink if the temperature indicates a thermal error condition. In some instances, aspects of the nucleic acid amplification module include where the heatsink is configured to receive a second mechanical fastener and the nucleic acid amplification module further comprises a second thermal block in thermal contact with a second thermoelectric cooler unit in thermal contact with the heatsink, wherein the second thermal block, the second thermoelectric cooler unit and the heatsink are joined by a second mechanical fastener positioned through mounting holes in the second thermal block and the second thermoelectric cooler unit and affixed to the heatsink. In some instances, aspects of the nucleic acid amplification module include where the first thermal block and the second thermal block comprise separate electrical connections and are controlled independently. In some instances, aspects of the nucleic acid amplification module includes one or more reaction vessel clamping bars, including where the one or more reaction vessel clamping bars provides a compression force on reaction vessels within the reaction vessel wells of 5 N or more.

Aspects of the instant disclosure include a multi-reaction analysis module for the optical analysis of a plurality of amplification reaction vessels, the module comprising: a) an optics detection unit comprising an optical signal processor and a plurality of linearly arranged optical blocks, each optical block comprising: i) an illumination component configured to illuminate a reaction with excitation light; ii) a optics block aperture configured to pass excitation light to the reaction vessel and receive emission light from the reaction vessel; iii) a measurement channel configured to pass emission light to the optical signal processor; and iv) a reference channel configured to pass reference light to the optical signal processor; b) a linear conveyer configured to convey the optics detection unit linearly past each reaction vessel of the plurality of amplification reactions, wherein each optics block aperture of the plurality of linearly arranged optical blocks is optically exposed to the sidewall of each reaction vessel.

In some instances, aspects of the multi-reaction analysis module include where the illumination component comprises one or more light emitting diode (LED) emitters or two or more light emitting diode (LED) emitters of different emission wavelengths, including where the wavelengths of the two or more LED emitters are at least 50 nm apart. In some instances, aspects of the multi-reaction analysis module include where the illumination component comprises frequency modulation. In some instances, aspects of the multi-reaction analysis module include where the illumination component comprises time division modulation. In some instances, aspects of the multi-reaction analysis module include where the optics detection unit comprises two or more optical blocks or three optical blocks.

Aspects of the instant disclosure include an integrated multi-reaction nucleic acid amplification and analysis system, the system comprising: a) a nucleic acid amplification module and a multi-reaction analysis module, wherein the spacing between the side apertures of the reaction vessel wells is unequal to the spacing between the optics block apertures of the optical blocks such that no more than one reaction vessel side aperture and one optics block aperture may be in alignment at any one time.

In some instances, aspects of the integrated multi-reaction nucleic acid amplification and analysis system include where the spacing between the side apertures is greater than the spacing between the optics block apertures. In some instances, aspects of the integrated multi-reaction system include where the spacing between the side apertures is less than the spacing between the optics block apertures. In some instances, aspects of the integrated multi-reaction system include two thermal blocks affixed to a single heatsink. In some instances, aspects of the integrated multi-reaction system include wherein the multi-reaction analysis module comprises three optical blocks. In some instances, aspects of the integrated multi-reaction system include where each illumination component comprises two or more LED emitters of differing wavelengths, including wherein the wavelengths of the two or more LED emitters are at least 50 nm apart.

Aspects of the instant disclosure include an integrated multi-reaction nucleic acid amplification and analysis system, the system comprising: a) a multi-reaction nucleic acid amplification module comprising two or more thermal blocks comprising two or more linearly arranged and evenly spaced reaction vessel wells each having a side aperture configured to allow light to pass laterally into the reaction vessel well; b) a traveling optics detection unit comprising: i) an optical signal processor; ii) a plurality of linearly arranged evenly spaced optical blocks, each optical block comprising an illumination component and a optics block aperture configured to pass excitation light to a reaction vessel and receive emission light from the reaction vessel; and iii) a linear conveyer configured to convey the traveling optics detection unit linearly past the side aperture of each of the two or more reaction vessel wells, wherein the spacing between the side apertures of the reaction vessel wells is unequal to the spacing between the optics block apertures of the optical blocks such that no more than one side aperture and one optics block aperture may be in alignment at any one time.

In some instances, aspects of the integrated multi-reaction system include where the traveling optics detection unit comprises three optical blocks. In some instances, aspects of the integrated multi-reaction system include where the illumination component comprises two or more LED emitters of differing wavelengths, including where the wavelengths of the two or more LED emitters are at least 50 nm apart.

Aspects of the instant disclosure include a method of monitoring nucleic acid amplification in a plurality of amplification reaction vessels, the method comprising: a) linearly scanning a traveling optics detection unit having an excitation component and a plurality of optics block apertures past the plurality of amplification reaction vessels, wherein no more than one optics block aperture is in optical alignment with a amplification reaction vessel at any one time; b) receiving a scan signal from the optics detection unit comprising background noise and emission peaks; c) determining emission peaks within the background noise according to a plurality of reaction vessel windows; d) measuring an intensity value for each reaction vessel window to monitor the amplification in each reaction vessel of the plurality.

In some instances, aspects of the method include where the optics unit comprises a plurality of excitation components that are time modulated. In some instances, aspects of the method include where the optics unit comprises a plurality of excitation components that are frequency modulated. In some instances, aspects of the method include where each optics block aperture is part of an optics block and the method further comprises cross-talk subtraction. In some instances, aspects of the method include where the method further comprises one or more calibration measurement steps before or during the linear scanning step. In some instances, aspects of the method include where the one or more calibration measurement steps comprise aligning the plurality of optics block apertures with a dark target, including where the dark target comprises black polycarbonate. In some instances, aspects of the method include where the one or more calibration measurement steps comprises toggling the excitation component on or off. In some instances, aspects of the method include where the one or more calibration measurement steps comprises measuring a reference channel and adjusting the power supplied to the excitation component based on the measured reference channel. In some instances, aspects of the method include where at least one of the one or more calibration measurement steps is performed at least once per scan. In some instances, aspects of the method include where at least one of the one or more calibration measurement steps is performed at least twice per scan. In some instances, aspects of the method include where the measurement from the calibration measurement step is applied to a value obtained from the scan during a signal processing pathway.

BRIEF DESCRIPTION OF THE FIGURES

FIG. 5 depicts one embodiment of a mounted pair of thermal blocks fastened to a single heat sink as described herein.

FIG. 16 demonstrates the peak pattern generated during a lateral scan of a reaction vessel according to an embodiment of the instant disclosure.

DEFINITIONS

Figure 1:
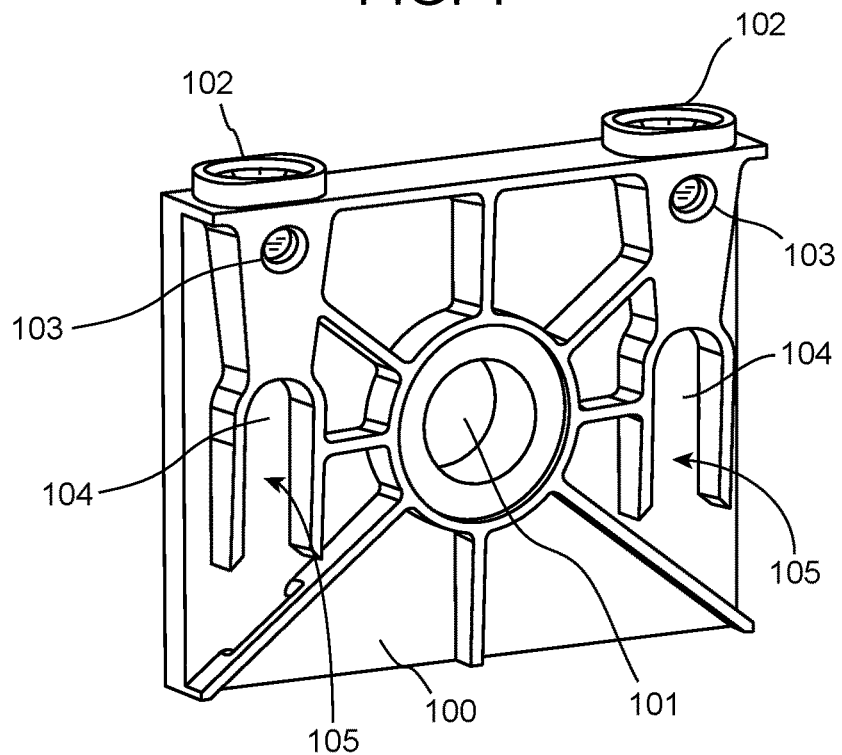
FIG. 1 depicts one embodiment of a thermal block as described herein.

The term "analyte" as used herein refers to a target molecule to be detected in a sample wherein detection of the analyte may be indicative of a biological state of the organism from which the sample was derived. For example, where an analyte is a nucleic acid analyte, detection of the nucleic acid analyte may be indicative of a biological state of the organisms from which the sample was derived including e.g., where detection of viral nucleic acid may indicate infection with a particular pathogen, etc.

The term "reaction vessel" as used herein generally referrers to a container within which an amplification reaction is performed. Such reaction vessels may be obtained from commercial sources, e.g., as off-the-shelf components, or may be custom manufactured. Reaction vessels useful in nucleic acid amplification reactions will generally be capable of rapidly transferring heat across the vessel, e.g., through the use of highly conductive materials (e.g., thermally conductive plastics) or physical modifications of the vessel (e.g., thin walls). Common reaction vessels include but are not limited to e.g., tubes, vials, multi-well plates, and the like. Reaction vessels may be constructed of a variety of materials including but not limited to e.g., polymeric materials. In some instances, a reaction vessel of the instant disclosure may be a reaction vessel and or reaction vessel system as described in e.g., which claims priority to U.S. Ser. No. 62/308,620, the disclosures of which are incorporated herein by reference in their entireties. In some instances, a component of a device or system or a method as described herein may be configured for use with or to be applicable with a reaction vessel and/or reaction vessel system as described in e.g., which claims priority to U.S. Ser. No. 62/308,620.

The term "polymeric materials" as used herein includes, e.g., plastics, resins, etc., and other materials generated by the joining of unit structures, e.g., in linear or branched form. Useful polymeric materials may include but are not limited to e.g., those commonly used in research and industrial settings, including but not limited to: acetal, cyclic olefin copolymer, ethylene propylene diene monomer rubber, ethylene propylene rubber, ethylene-chlorotrifluoroethylene copolymer (Halar®), ethylene-tetrafluoroethylene (Tefzel), fluorinated ethylene propylene (Teflon®), fluorinated polyethylene, high impact polystyrene, high-density polyethylene, low-density polyethylene, modified polyphenylene ether, Permanox, polyaryletherketone (PAEK) family polymeric materials (e.g., polyether ether ketone (PEEK) and the like), polycarbonate, polyetherimide, polyethylene teraphthalate, polyethylene terephthalate copolymer, polyfluoroalkoxy (Teflon®), polymethyl methacrylate (acrylic), polymethylpentene, polypropylene, polypropylene copolymer, polystyrene, polysulfone, polyvinylidenedifluoride, ResMer™, styrene acrylonitrile, tetrafluoroethylene, tetrafluoroethylene (Teflon®), Thermanox, thermoplastic elastomer, thermoplastic polyester polyurethane, Tritan™, cyclic olefin polymer (COP), and the like.

The term "assessing" includes any form of measurement, and includes determining if an element is present or not. The terms "determining", "measuring", "evaluating", "assessing" and "assaying" are used interchangeably and include quantitative and qualitative determinations. Assessing may be relative or absolute. "Assessing the identity of" includes determining the most likely identity of a particular compound or formulation or substance, and/or determining whether a predicted compound or formulation or substance is present or absent. "Assessing the quality of" includes making a qualitative or quantitative assessment of quality e.g., through the comparisons of a determined value to a reference or standard of known quality.

The term "bodily fluid" as used herein generally refers to fluids derived from a "biological sample" which encompasses a variety of sample types obtained from an individual or a population of individuals and can be used in a diagnostic, monitoring or screening assay. The definition encompasses blood and other liquid samples of biological origin. The definition also includes samples that have been manipulated in any way after their procurement, such as by mixing or pooling of individual samples, treatment with reagents, solubilization, or enrichment for certain components, such as nucleated cells, non-nucleated cells, pathogens, etc.

The term "biological sample" encompasses a clinical sample, and also includes cells in culture, cell supernatants, cell lysates, serum, plasma, biological fluid, and tissue samples. The term "biological sample" includes urine, saliva, cerebrospinal fluid, interstitial fluid, ocular fluid, synovial fluid, blood fractions such as plasma and serum, and the like.

The terms "control", "control assay", "control sample" and the like, refer to a sample, test, or other portion of an experimental or diagnostic procedure or experimental design for which an expected result is known with high certainty, e.g., in order to indicate whether the results obtained from associated experimental samples are reliable, indicate to what degree of confidence associated experimental results indicate a true result, and/or to allow for the calibration of experimental results. For example, in some instances, a control may be a "negative control" assay such that an essential component of the assay is excluded such that an experimenter may have high certainty that the negative control assay will not produce a positive result. In some instances, a control may be "positive control" such that all components of a particular assay are characterized and known, when combined, to produce a particular result in the assay being performed such that an experimenter may have high certainty that the positive control assay will not produce a positive result. Controls may also include "blank" samples, "standard" samples (e.g., "gold standard" samples), validated samples, etc.

The term "inputting", as used herein, is used to refer to any way of entering information into a computer, such as, e.g., through the use of a user interface. For example, in certain cases, inputting can involve selecting a reference spectrum or a spectral characteristic or library thereof that is already present on a computer system. In other cases, inputting can involve adding a spectrum or a spectral characteristic to a computer system, e.g., by measuring the spectrum of a sample on a device capable of interfacing with a computer. Inputting can also be done using a user interface.

By "data processing unit", as used herein, is meant any hardware and/or software combination that will perform the functions required of it. For example, any data processing unit herein may be a programmable digital microprocessor such as available in the form of an electronic controller, mainframe, server or personal computer (desktop or portable). Where the data processing unit is programmable, suitable programming can be communicated from a remote location to the data processing unit, or previously saved in a computer program product (such as a portable or fixed computer readable storage medium, whether magnetic, optical or solid state device based).

DETAILED DESCRIPTION

The instant disclosure provides nucleic acid amplification systems and multi-reaction analysis systems useful in the efficient processing of samples, including clinical samples. Integrated systems that include nucleic acid amplification devices functionally combined with multi-reaction analysis systems are also included. Also provided are methods for monitoring multiple concurrent nucleic acid amplification reactions that include the use of devices and systems described herein.

Before the present invention is described in greater detail, it is to be understood that this invention is not limited to particular embodiments described, as such may, of course, vary. It is also to be understood that the terminology used herein is for the purpose of describing particular embodiments only, and is not intended to be limiting, since the scope of the present invention will be limited only by the appended claims.

Where a range of values is provided, it is understood that each intervening value, to the tenth of the unit of the lower limit unless the context clearly dictates otherwise, between the upper and lower limit of that range and any other stated or intervening value in that stated range, is encompassed within the invention. The upper and lower limits of these smaller ranges may independently be included in the smaller ranges and are also encompassed within the invention, subject to any specifically excluded limit in the stated range. Where the stated range includes one or both of the limits, ranges excluding either or both of those included limits are also included in the invention.

Certain ranges are presented herein with numerical values being preceded by the term "about." The term "about" is used herein to provide literal support for the exact number that it precedes, as well as a number that is near to or approximately the number that the term precedes. In determining whether a number is near to or approximately a specifically recited number, the near or approximating unrecited number may be a number which, in the context in which it is presented, provides the substantial equivalent of the specifically recited number.

Unless defined otherwise, all technical and scientific terms used herein have the same meaning as commonly understood by one of ordinary skill in the art to which this invention belongs. Although any methods and materials similar or equivalent to those described herein can also be used in the practice or testing of the present invention, representative illustrative methods and materials are now described.

All publications and patents cited in this specification are herein incorporated by reference as if each individual publication or patent were specifically and individually indicated to be incorporated by reference and are incorporated herein by reference to disclose and describe the methods and/or materials in connection with which the publications are cited. The citation of any publication is for its disclosure prior to the filing date and should not be construed as an admission that the present invention is not entitled to antedate such publication by virtue of prior invention. Further, the dates of publication provided may be different from the actual publication dates which may need to be independently confirmed.

It is noted that, as used herein and in the appended claims, the singular forms "a", "an", and "the" include plural referents unless the context clearly dictates otherwise. It is further noted that the claims may be drafted to exclude any optional element. As such, this statement is intended to serve as antecedent basis for use of such exclusive terminology as "solely," "only" and the like in connection with the recitation of claim elements, or use of a "negative" limitation.

As will be apparent to those of skill in the art upon reading this disclosure, each of the individual embodiments described and illustrated herein has discrete components and features which may be readily separated from or combined with the features of any of the other several embodiments without departing from the scope or spirit of the present invention. Any recited method can be carried out in the order of events recited or in any other order which is logically possible.

Methods

The instant disclosure provides methods of amplifying a target nucleic acid, i.e., nucleic acid analyte, present in a sample and detecting a target nucleic acid by monitoring a nucleic acid amplification reaction. Methods of the instant disclosure include the use of devices and systems described herein, including nucleic acid amplification devices and multi-reaction monitoring/analysis devices and integrated systems thereof, in amplifying and/or monitoring the amplification of a target nucleic acid as described herein.

Real-Time Polymerase Chain Reaction

Such monitoring to detect the presence of a nucleic acid analyte and/or quantify the initial amount of a nucleic acid analyte in a sample, e.g., a biological sample, is the basis for what is commonly referred to as real-time polymerase chain reaction (real-time PCR).

The PCR process is a nucleic acid amplification method whereby a target nucleic acid sequence is amplified by a factor of $2^n$ by repeating (1) a denaturing temperature (e.g., of 95° C.) that serves to denature the two strands of a double stranded nucleic acid template; (2) an annealing temperature (e.g., on the order of 55° C. to 65° C.) that serves to anneal one or more complementary nucleic acids to a single strand of the denatured nucleic acid; and (3) an extension temperature that provides the permissive temperature for a nucleic acid polymerase to extend the complementary nucleic acid according to the sequence of the template, alternately n times (referred as a "thermal cycle").

In real-time PCR, the amount of nucleic acid is measured at a plurality of time points during the amplification reaction to determine the actual or relative amount of target nucleic acid analyte initially present in the sample. Real-time PCR may be quantitative, semi-quantitative or qualitative. Real-time PCR is generally carried out in a thermal cycler with the capacity to illuminate each amplification sample with a beam of light of at least one specified wavelength and detect the fluorescence emitted by an excited fluorophore that is either incorporated into the amplicon or unquenched during amplification. Non-specific fluorochromes (e.g., DNA binding dyes such as e.g., SYBR Green) or specific fluorescent hybridization probes may be used. Using different-colored labels, fluorescent probes can be used in multiplex assays for monitoring several target sequences in the same tube.

One method of using fluorescently labeled probes relies on a DNA-based probe with a fluorescent reporter at one end and a quencher of fluorescence at the opposite end of the probe. The close proximity of the reporter to the quencher prevents detection of its fluorescence. When bound to a target sequence, breakdown of the probe by the 5' to 3' exonuclease activity of the polymerase breaks the reporter-quencher proximity and thus allows unquenched emission of fluorescence, which can be detected after excitation with a particular wavelength of light. An increase in the product targeted by the reporter probe at each PCR cycle therefore causes a proportional increase in fluorescence due to the breakdown of the probe and release of the reporter. Any convenient polymerase with 5' to 3' exonuclease activity may find use in such assays including but not limited to wild-type Taq polymerase and modified or engineered polymerases including but not limited to e.g., those available from commercial suppliers such as e.g., New England Biolabs (Ipswich, MA), Life Technologies (Carlsbad, CA), Sigma Aldrich (St. Louis, MO) and Kapa Biosystems, Inc. (Wilmington, MA) such as e.g., KAPA2G DNA Polymerases.

In some instances, the methods as described herein and/or the devices and systems may be programmed, developed and/or used in conjunction with a method for multi-assay processing and analysis as described in e.g., which claims priority to U.S. Ser. No. 62/308,625, and/or a sample processing device and/or method related thereto as described in e.g., which claims priority to U.S. Ser. No. 62/308,625, the disclosures of which are incorporated herein by reference in their entireties.

Multi-Reaction Monitoring

Methods of the instant disclosure include multi-reaction monitoring where the amplification of a plurality, e.g., two or more, ongoing amplification reactions are analyzed in real-time to quantitatively, semi-quantitatively, or qualitatively determine whether a target nucleic acid is present in a sample. The number of reactions monitored in a multi-reaction monitoring method of the instant disclosure may vary and may range from 2 to 100 or more where the number of reactions is scalable with the number of multi-reaction monitoring devices used in the method.

In some instances, the number of samples monitored in a multi-reaction monitoring method utilizing a single multi-reaction analysis device, as described herein, may be limited by the range and/or rate of travel of an optics device attached to a conveyor which passes the optics device past the samples to facilitate monitoring. As such, the number of reaction vessels monitored by a single multi-reaction analysis device, as described herein, will vary and may range from 1 to 48 or more including but not limited to e.g., 1 to 44, 1 to 40, 1 to 36, 1 to 32, 1 to 28, 1 to 24, 1 to 20, 1 to 16, 1 to 12, 1 to 8, 1 to 4, 2 to 48, 2 to 44, 2 to 40, 2 to 36, 2 to 32, 2 to 28, 2 to 24, 2 to 20, 2 to 16, 2 to 12, 2 to 8, 2 to 4, 4 to 48, 4 to 44, 4 to 40, 4 to 36, 4 to 32, 4 to 28, 4 to 24, 4 to 20, 4 to 16, 4 to 12, 4 to 8, 8 to 48, 8 to 44, 8 to 40, 8 to 36, 8 to 32, 8 to 28, 8 to 24, 8 to 20, 8 to 16, 8 to 12, 12 to 48, 12 to 44, 12 to 40, 12 to 36, 12 to 32, 12 to 28, 12 to 24, 12 to 20, 12 to 16, 16 to 48, 16 to 44, 16 to 40, 16 to 36, 16 to 32, 16 to 28, 16 to 24, 16 to 20, 20 to 48, 20 to 44, 20 to 40, 20 to 36, 20 to 32, 20 to 28, 20 to 24, 24 to 48, 24 to 44, 24 to 40, 24 to 36, 24 to 32, 24 to 28, 6 to 26, 8 to 24, 10 to 22, 10 to 20, 10 to 18, 10 to 16, 10 to 14, 24, 20, 18, 16, 14, 12, etc.

Methods of multi-reaction monitoring, as described herein, generally include scanning a traveling optics detection unit, configured to optically assess a nucleic acid amplification reaction, past a plurality of reaction vessels in a manner sufficient to collect real-time measurements for the quantitative, semi-quantitative or qualitative assessment of amplification. In many embodiments, the plurality of reaction vessels is linearly aligned such that scanning linearly is sufficient to pass the traveling optics detection unit past all vessels of the plurality.

According to the methods described herein, the optical analysis may be performed through aligned apertures, including e.g., where, during the scanning, only one reaction vessel is analyzed at a time through a pair of aligned apertures. For example, in some instances, a traveling optics detection unit having a plurality of linearly arranged optical blocks is scanned past a plurality of amplification reaction vessels present in a nucleic acid amplification device and aligned apertures of the optical blocks and the nucleic acid amplification device allows for the optical monitoring of amplification in the reaction vessels.

In one embodiment, scanning of the optics block, emitting an excitation light, along the sidewall of the reaction vessel allows for the collection of an emissions peak defined by the path of the excitation light along the sidewall of the reaction vessel. For example, FIG. 16 depicts the passage of an analysis point across the cross section of an ultra-thin wall reaction vessel, allowing for the collection of the emission peak shown. Accordingly, in embodiments where the sidewall of the reaction vessel is scanned, either along the entire width of the reaction vessel or along the width of the reaction vessel exposed by an aperture or a portion thereof, more data is collected as compared to e.g., where a single point on a portion of the reaction vessel is analyzed. Following the collection of a scan, which may include a plurality of emission peaks and other non-signal elements, including e.g., noise, the scan may be further processed, including but not limited to through various signal processing pathways including e.g., for the detection and/or filtering and/or measurement of the peaks in the scan.

In some instances, methods for monitoring multiple amplification reactions as described herein may include various procedures directed at reducing the noise in the detection system, where "noise" encompasses any disturbance, including random disturbances and persistent disturbances, which obscures or reduces the clarity of a signal. Thus, noise may be electronic noise, optical noise, and the like. Noise also encompasses crosstalk between channels of a system where the channels are configured to function independently.

Methods for reducing noise in the systems described herein include but are not limited to time division multiplexing, frequency division multiplexing, spatial separation, and the like. In some instances, methods of the instant disclosure further include post-signal acquisition noise reduction, including e.g., where noise is filtered out using one or more filtering algorithms.

Time division multiplexing noise reduction, as it applies to the devices and systems described herein, generally involves separating or segmenting elements of a detection process across time so as to reduce the simultaneous generation and/or collection of signals, e.g., by different channels of the system, particularly where two channels may share a light path or have shared components of a light path.

In some instances, the methods as described herein include time division multiplexing of the elements of an illumination component used in multi-reaction analysis. For example, excitation elements, including e.g., LED emitters as described in more detail herein, may be sequentially toggled so as to prevent the simultaneous activation of two different LEDs of the system thereby preventing the simultaneous emission of excitation light from two different LEDs, including e.g., two LEDs of different wavelengths. Such methods may or may not involve "dark periods" also referred to as "dummy" periods, i.e., periods where all or both illumination elements are off. Dark periods may, in some instances, be utilized between the toggling of illumination elements to further prevent the simultaneous activation of both elements or the simultaneous presence of light from two different elements. Toggling of illumination elements may occur at any convenient frequency (i.e., interval) provided the frequency (i.e., interval) is sufficient for the detection needs of the system and the frequencies of multiple illumination elements are purposefully uncoordinated to prevent simultaneous activation of elements.

Figure 22:
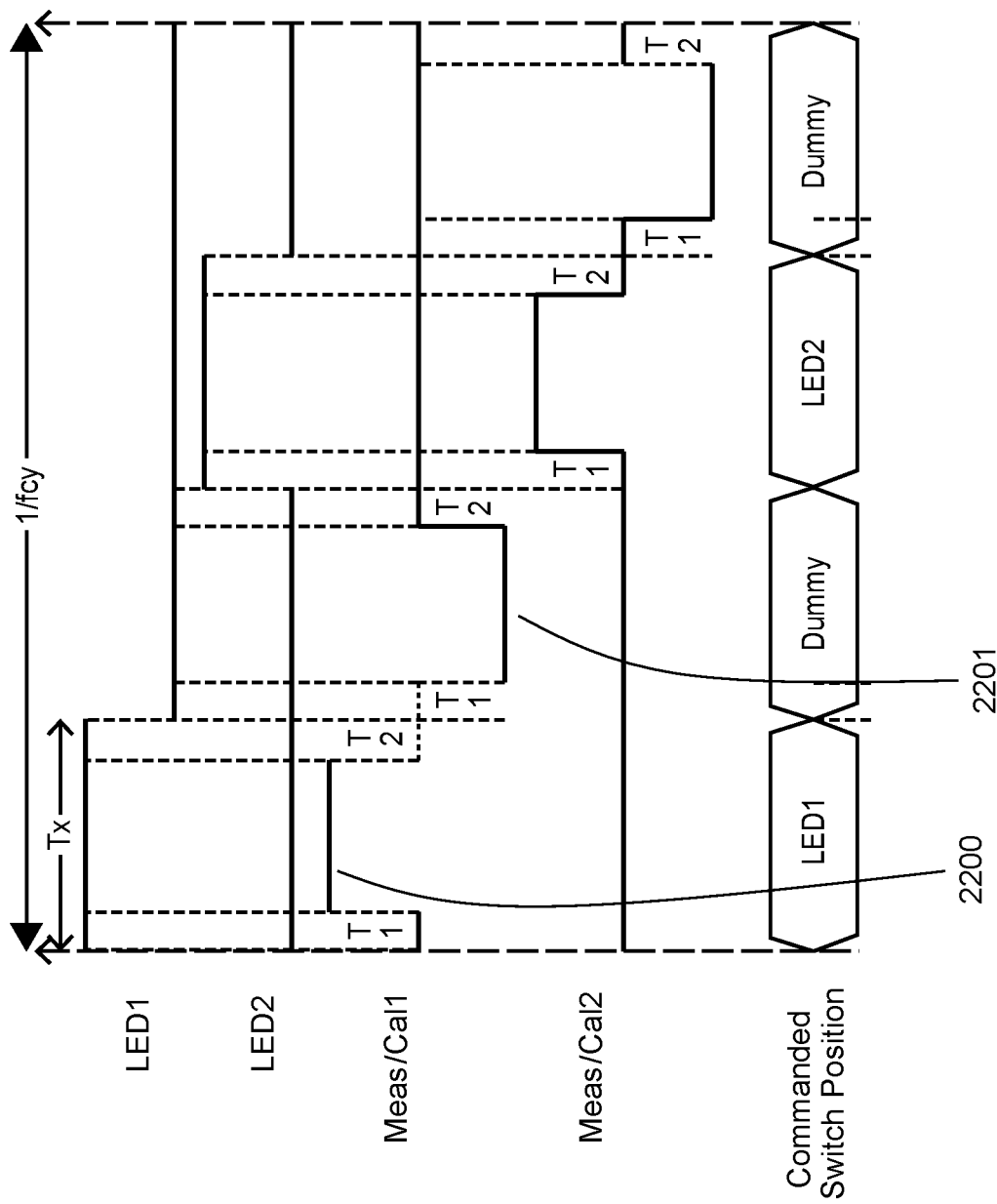
FIG. 22 depicts one embodiment of 2-way time division multiplexing as described herein.

As an example of 2-way time division multiplexing, in one embodiment depicted in FIG. 22, during a cycle (1/fcy) a first LED (LED1) of a first wavelength is toggled on for a time (Tx) equal to one quarter of the cycle. Correspondingly, later in the cycle a second LED (LED2) of a second wavelength is toggled on for a period of time equal to Tx. In addition, measurement and calibration windows may be configured to correspond with the toggling of each LED. For example, measurement and calibration of the channel corresponding to LED1 (Meas/Cal1) may be configured such that the measurement window for the channel (2200) corresponds only with the time LED1 is toggled on. Likewise the calibration window in the channel corresponding to LED1 (2201) may follow the measurement window and take place e.g., only when LED1 is toggled off. Similar measurement and calibration windows (Meas/Cal2) may be spaced throughout the cycle for the channel corresponding to LED2 such that measurement for the channel is only taken e.g., when LED2 is toggled on and calibration is taken when e.g., LED2 is toggled off. In some instances, the measurement windows for each channel are smaller than the time the LED of the channel is toggled on and may include time before (T1) and after (T2) measurement when the LED may be toggled on and no measurement is taken. Likewise, calibration windows may similarly make use of time periods before and after calibration that are smaller, e.g., by T1 and T2, than the actual dark period between LED toggling. As will be readily understood, calibration measurements need not be limited to time periods where LEDs are off and calibration measurements may, in some instances, be made when one or more LED elements are toggled on.

2-way time division multiplexing may find use in reducing noise within optical blocks that contain two or more toggle-able illumination elements, including e.g., toggle-able LED emitters. Where a system involves more than two channels, including e.g., two or more optics blocks each with two or more illumination elements (e.g., three optics blocks with two LED emitters each, three optics blocks with four LED emitters each, etc.), multiple 2-way time division multiplexing cycles can be utilized. In some instances where multiple 2-way time division multiplexing cycles are utilized the cycles may have generally the same scheme but with a different overall cycle times. In other instances, where multiple 2-way time division multiplexing cycles are utilized the cycles may have the same scheme and the same overall cycle times.

Frequency division multiplexing noise reduction, as it applies to the devices and systems described herein, generally involves modulation between shared optical paths (e.g., within an optical block) to provide optical and/or electrical rejection between blocks. Accordingly, the components of an optical block may be similarly modulated with respect to one another but differently modulated with respect to components of another optical block of the system (i.e., modulation may differ from block to block). For example, two channels sharing a first optical block may both modulate at frequency X, while two channels sharing a second optical block may both modulate at frequency Y, where frequencies X and Y are not equal. In some instances, the frequencies of different optical blocks of the system may be chosen to be as separated as possible.

Any convenient frequency modulation may find use in frequency division multiplexing as described herein, including but not limited to e.g., 0.1 kHz, 0.2 kHz, 0.3 kHz, 0.4 kHz, 0.5 kHz, 0.6 kHz, 0.7 kHz, 0.8 kHz, 0.9 kHz, 1 kHz, 1.1 kHz, 1.2 kHz, 1.3 kHz, 1.4 kHz, 1.5 kHz, 1.6 kHz, 1.7 kHz, 1.8 kHz, 1.9 kHz, 2 kHz, 2.1 kHz, 2.2 kHz, 2.3 kHz, 2.4 kHz, 2.5 kHz, 2.6 kHz, 2.7 kHz, 2.8 kHz, 2.9 kHz, 3 kHz, etc. For example, in some instances, a first channel may be frequency modulated at 1 kHz, a second channel at 1.6 kHz and a third channel at 2.3 kHz. In addition, where frequency modulation is employed at a particular frequency, system components receiving the modulated frequency will demodulate at a corresponding frequency.

In addition, where frequency modulation is employed, the detectors for a particular optical block will demodulate at a frequency corresponding to the modulation frequency of the channels of the block. As such, by demodulating the detectors of the block at a particular frequency, the detectors not only reject stray signal from the other channels of the other blocks, which are modulated at a different frequency, but also are more immune to ambient disturbances, including e.g., stray light.

Spatial separation noise reduction, as it applies to the devices and systems described herein, generally involves particular physical spacing of system components to prevent noise, including optical crosstalk and/or electrical crosstalk, transfer between system components. When spatial separation noise reduction is employed considerations may be made to limit spatial separation so not to needlessly increase the size of the overall system, the time required to make measurements in the system, etc.

In some instances, the methods as described herein include physical spacing of system components to physically prevent simultaneous activation and/or measurement by different components thereby preventing the transfer of noise, including optical noise and/or electrical noise, from one component to another.

For example, in some instances, spatial separation noise reduction may be employed in a multi-reaction monitoring method, as described herein, by permanently spacing the individual units of arrayed detection components and the individual units arrayed reaction vessels unequally such that, following a measurement, either the arrayed detection components or the arrayed reaction vessels must be physically moved to align for the next measurement. Accordingly, in certain embodiments, the spacing between individual units of arrayed detection components may be less than the spacing between the individual units of arrayed reaction vessels. In other embodiments, the spacing between individual units of arrayed detection components may be greater than the spacing between the individual units of arrayed reaction vessels.

Figure 23:
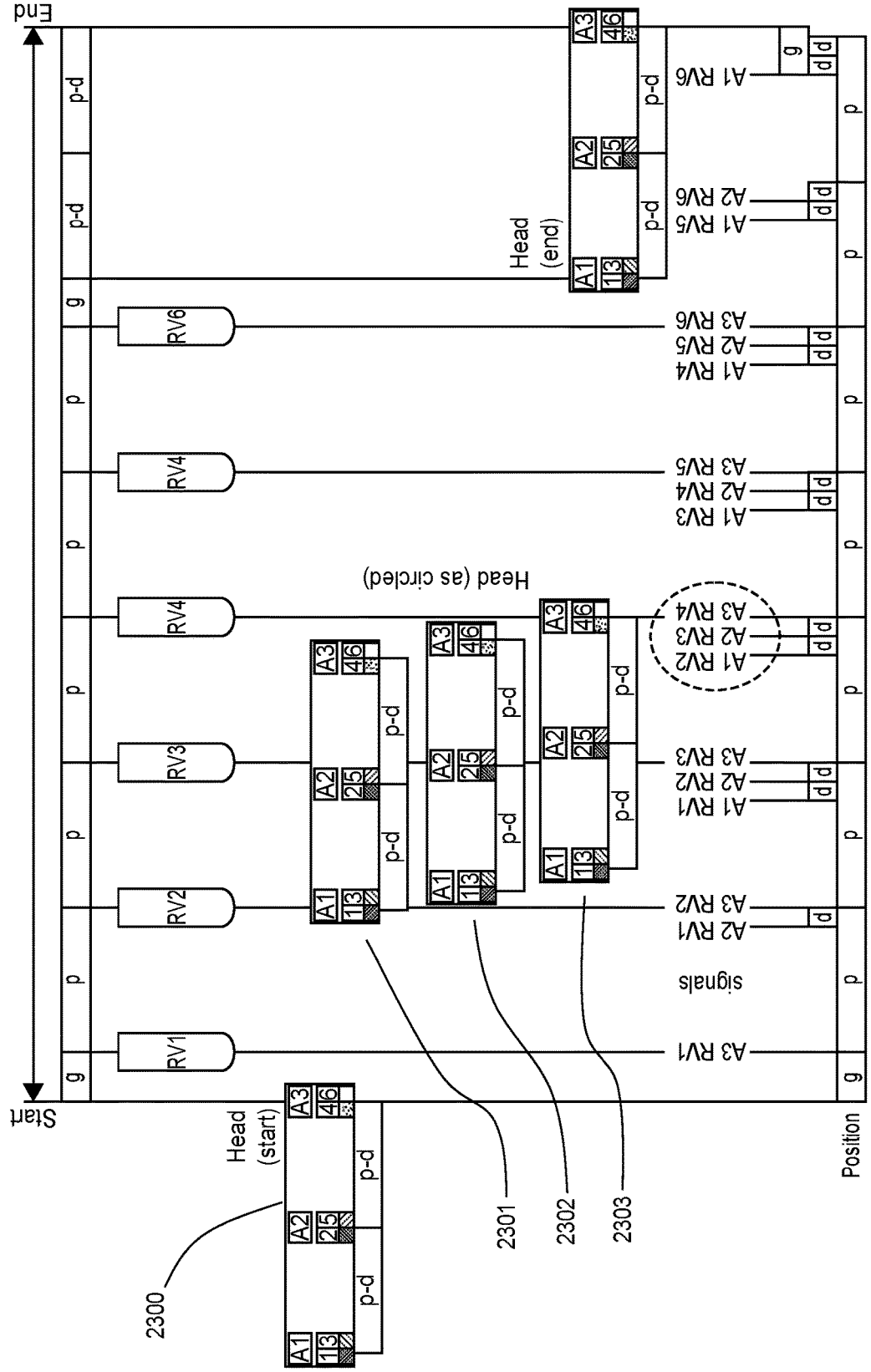
FIG. 23 provides a schematic representation of a multi-reaction vessel scan performed by an integrated system according to an embodiment as described herein.

In one embodiment, as depicted in FIG. 23, a scan of arrayed reaction vessels (R1-R6) with spacing "p" by an optical detection unit (2300) with three optical blocks (A1-A3) spaced "p-d" apart makes use of spatial separation to prevent simultaneous measurements of any two reaction vessels. For example, as the optical detection unit proceeds through the scan along the x-axis of the diagram in FIG. 23, at no time is more than one optical block (A1-A3) in alignment with a reaction vessel (R1-R6). Thus, the unequal spacing between the optical blocks as compared to the spacing between the reaction vessels prevents simultaneous alignment of two optical block/reaction vessel pairs thus preventing simultaneous measurements during the scan.

As shown the detail in FIG. 23, the optical block A1 aligned with reaction vessel RV2 (2301) makes a measurement of RV2 and proceeds to the next position (2302) where optical block A2 is aligned with reaction vessel RV3, yet neither A1 and RV2 nor A3 and Rv4 are in alignment when A2 is aligned with RV3. Following the measurement at RV3 (2302) the optical unit proceeds to the next position (2303) where RV4 is aligned with A3 and a measurement may be made, however when RV4 and A3 are in alignment, neither A1 nor A2 are aligned with any other reaction vessels. Accordingly, spaced measurements may be made essentially as depicted across the scan shown on the x-axis of FIG. 23, where from first to last: optics block A3 reads RV1; optics block A2 reads RV1; optics block A3 reads RV2; optics block A1 reads RV1; optics block A2 reads RV2; optics block A3 reads RV3; optics block A1 reads RV2; optics block A2 reads RV3; optics block A3 reads RV4; optics block A1 reads RV3; optics block A2 reads RV4; optics block A3 reads RV5; optics block A1 reads RV4; optics block A2 reads RV5; optics block A3 reads RV6; optics block A1 reads RV5; optics block A2 reads RV6; and optics block A1 reads RV6. Accordingly, each optics block reads each reaction vessel, however the spatial arrangement of the optics blocks relative to the reaction vessels during the scan assures that only one optics block reads only one reaction vessel at any one time during a scan.

Various different spacing schemes may be employed to make use of spatial separation noise reduction as described herein, depending, at least part, on the size of the components of the system and the conveyance means employed to physically move components of the system.

Figure 14:
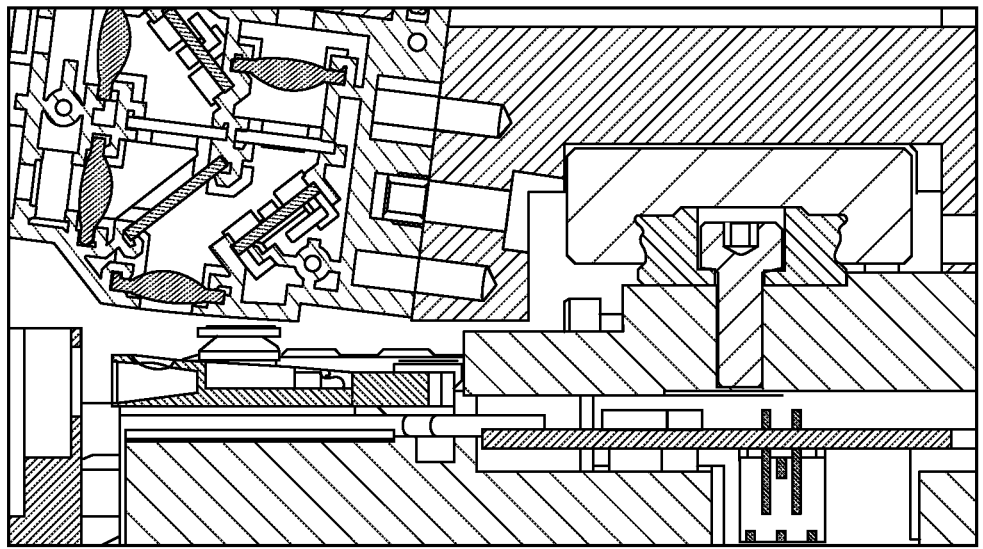
FIG. 14 provides a cut away view of an embodiment of integrated system that combines an amplification unit and a multi-reaction analysis unit as described herein.

In some instances, other spatial orientations of components of the described systems may be employed to decrease noise of the system. For example, in some instances optical measurements between an optics block and a reaction vessel may be made at an angle that decreases the introduction of noise into the measurements. For example, as depicted in FIG. 14, measurement may be made between a reaction vessel that is essentially vertical (at left) and an optics block (cutaway at right) that is at some angle away from horizontal, including e.g., where the analysis aperture of the optics block (i.e., the optics block aperture) is angled up from horizontal towards the reaction vessel. In some embodiments, e.g., as depicted in FIG. 14, the optics block and the thermal block(s) may be configured in relation to one another such that the angled side wall of the reaction vessel and the optics block aperture are parallel. In such instances, the optical path of the optics block may be essentially perpendicular to the angled sidewall of the reaction vessel as it rests in the thermal block. For example, in some embodiments, due to the angle of the reaction vessel side wall, the optics block may be correspondingly angled including e.g., where the optics block is angled between 1° or less to 15° or more from vertical including but not limited to e.g., 1°, 2°, 3°, 4°, 5°, 6°, 7°, 8°, 9°, 10°, 11°, 12°, 13°, 14°, or 15° from vertical, where vertical may be determined e.g., based on the system as a whole or the primary vertical axis of the reaction vessel as it rests in the thermal block.

In some instances, the methods as described herein include calibration of components of a described device or system. Such calibration measurements may be performed before, during or after, and combinations thereof, an analysis as described herein. Such calibration measurements may be applied to the system before, during or after, and combinations thereof, an analysis as described herein. In some instances, a calibration measurement is performed before a scan, including but not limited to before each scan. In other instances, a calibration measurement is performed after a scan including but not limited to after each scan. In some instances, a calibration measurement is performed before and after a scan including but not limited to before and after each scan. In some instances, calibration is performed during a scan including but not limited to during each scan. In instances where a calibration measurement is taken more than once, including e.g., when a calibration measurement is taken before and after a scan and/or during a scan the subsequent calibration measurement(s) may be used to adjust the applied calibration including adjusting the calibration applied to the system based on the preceding calibration measurement.

In some instances, a calibration may be associated with (e.g., applied to) each measurement or with a set of measurements, including e.g., each set of measurements of a scan. Calibration components may be built into the analysis components of the devices as described herein.

Figure 13:
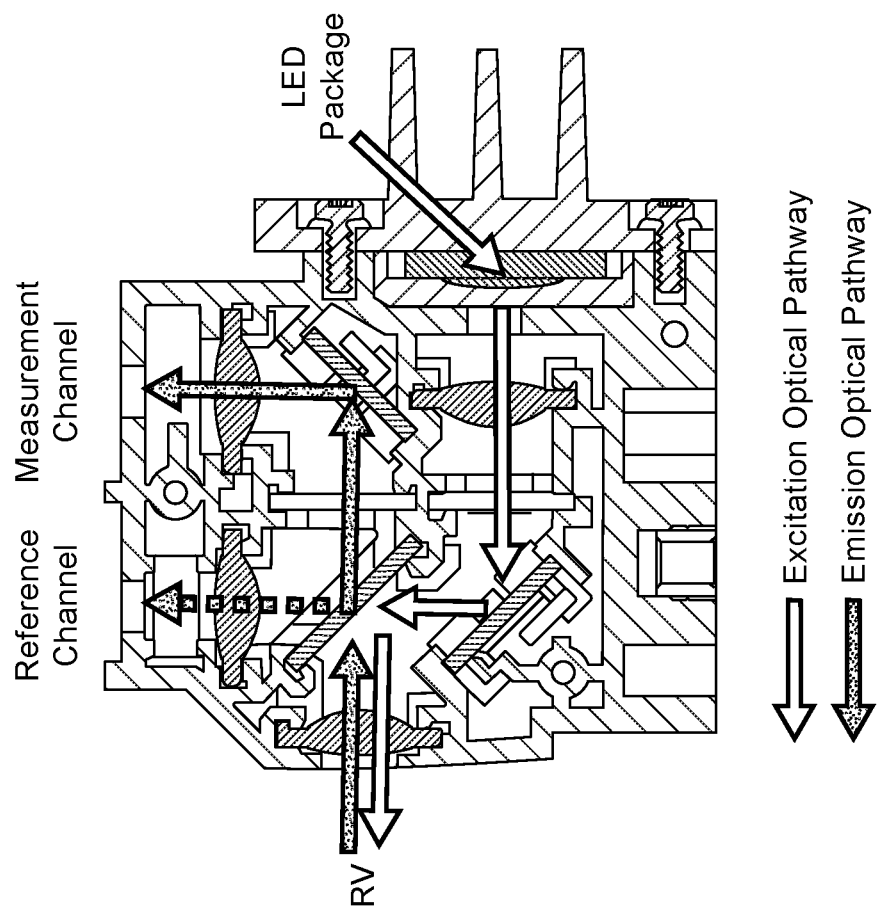
FIG. 13 provides a schematic cut away representation of the reference channel and the measurement channel light paths according to an embodiment of an optical block as described herein.

For example, in one embodiment of an optics block depicted in FIG. 13 an optics block of the instant disclosure may include a reference channel where such a reference channel serves in calibrating measurements made from the optics block. As shown in FIG. 13 an optics block may include a measurement channel and a reference channel. The light path of the measurement channel originates at the LED illumination component and is directed to the reaction vessel (RV) as excitation light. The RV returns emission light into the optics block and such emission light is directed to the measurement channel for measurement. In the reference channel, stray light passes through the reference channel aperture and is measured by an optical signal processor.

In some instances, an optics block may be calibrated by measuring the reference channel and the measurement channel in the absence of the emission light from a reaction vessel or in the presence of a reference light and then adjusting components of the optics block based on the measuring. For example, where the measurements from the reference channel and the measurement channel are unequal one or more components of the measurement channel may be adjusted until the reference channel and measurement channels are equal.

In some instances, at the beginning of a run, including but not limited to the beginning of every run, the LED drive currents may be set based on LED intensity values set for each channel during LED gain calibration. Such drive current adjustment may provide for consistent LED brightness run to run and may compensate for LED degradation where present. In some instances, once a current drive value is set for a run the value may be held constant for the length of the run and/or until current drive calibration is performed anew.

In one embodiment, at the beginning of a run the background signal of each reference channel is measured and each measurement is added to each LED reference intensity value to determine the set point for the reference channels. Once the set points are determined for each channel the LED drive currents are set to their default levels and a control loop is initiated to adjust the LED drive currents until the scan intensity to equal to the LED reference intensity plus the reference background signal.

In some instances, a "dark target" may be employed for calibration according to the methods as described herein, where an optical measurement is taken with the optics block aperture aligned to the dark target and a calibration is applied to the system based on the dark target measurement.

In embodiments of the methods described herein, before, during and/or after a scan, the detection unit may align with the dark target and a reading at the dark target may be taken. Accordingly, the dark target reading is analyzed to determine if adjustment of the applied calibration is necessary. In other embodiments, the dark target reading is used to calibrate one or more components of the optics block. In some instances, the detection unit must travel to the dark target to make a calibration reading. In other instances, the dark target is positioned in alignment with the optics block aperture of the optical unit when the optical unit is "at home" or "at rest" in its default position.

In some instances, two or more dark targets may be employed. For example, in some instances two dark targets may be used including but not limited to e.g., where a first dark target is present at one end of a linear optical scan and a second dark target is present at the other end of the linear optical scan. In such instances, a dark target measurement may be taken before, after or before and after each scan.

In instances where two or more calibration measurements are taken, use of the multiple measurements may vary. In some instances, the first and subsequent measurement(s), may be used in a statistical computation and the result of the statistical computation may be applied to the system. For example, the first and subsequent measurement(s), e.g., the first and second measurement, may be averaged and the resultant average may be applied to the system. In another example, the first and subsequent measurements may be complied and the median of the measurements may be applied to the system.

In other instances where two or more calibration measurements are taken, the first and subsequent measurement(s) may be applied differently to the system. For example, in some instances, the first measurement may be applied to one or more hardware components of the system, e.g., an electrical current of a component of the system may be adjusted based on the first measurement, and subsequent measurements may be applied to the data resulting from the instrument, e.g., based on a comparison of the first measurement to the subsequent measurement(s). In some instances, a calibration measurement may be made at the start of a run and the components of the system may be adjusted based on the calibration, then subsequent calibration measurements may be applied to the resultant data including e.g., where the subsequent measurement is compared to the first measurement and if the two are different the data is adjusted based on the difference between the first and second measurements.

Any component useful in normalizing the measurements between the reference channel and measurement channel may find use in applying a calibration as described herein. For example, in some instances, the power supplied to the illumination component, including e.g., one or more LED emitters of the illumination component, may be adjusted, e.g., increased or decreased, according to a calibration measurement made on the system. Such calibrations may be applied before or after a reaction vessel measurement including e.g., during a dark period. In other instances, such a calibration may be applied before or after a scan. Combinations of calibrations, e.g., applied both during scanning and before/after scans, may also find use in the methods as described herein.

In some instances, even when efforts are taken to limit noise and/or assure calibration of components, background noise may be collected with emission peak signals of the instant disclosure. Background noise present in a signal that also contains collected emission peaks may be minimized during collection and/or may be removed following to collection. For example, in some instances, background noise may be minimized during collection by collecting signal during a scan only when an optical block is in alignment with a reaction vessel. In some instances, the period of time an optical block is in alignment with a reaction vessel may be referred to as a reaction vessel window.

In some instances, the applied reaction vessel window may be smaller or larger than the actual time period that the optical block aperture is in alignment with a reaction vessel aperture. For example, in some instances, a reaction vessel window calibration may be performed to determine the actual time period the optical block aperture is in alignment with the reaction vessel aperture to determine the actual reaction vessel window and the applied reaction vessel window may be an expanded or contracted window based on the actual reaction vessel window. Determining and/or calibrating the actual reaction vessel window may be performed by any convenient means including but not limited to e.g., loading one or more reaction vessels with a fluorescent control (e.g., a control fluorescent dye, control fluorescent beads, control fluorescent nucleic acid, etc.), scanning the one or more reaction vessels with the optics block and measuring the control to determine the start and end of each control peak. In some instances, the applied reaction vessel window will be larger than the actual reaction vessel window including but not limited to e.g., one or more encoder counts larger than the actual reaction vessel window as determined by scanning a reaction vessel loaded with a fluorescent control.

In other instances, background noise may be removed following to collection e.g., through the use of one or more signal processing algorithms. For example, in instances where signal collection is not limited to reaction vessel windows, as described above, emission peaks may be determined in the scan data through the use of one or more peak finding algorithms or signal processing filters. Such post-collection signal processing methods may be used in combination with other methods of signal detection and/or reducing noise as described herein.

Following any noise reduction or noise removal and/or post-processing of the collected signal, a determination about the amplification state of the reaction may be made. Such determinations are generally based on a number of data points for the reaction collected over time, e.g., used in curve fitting, where e.g., the fitted curve can be used to calculate the starting amount of the target nucleic acid in the sample and/or whether the target nucleic acid is present in the sample. In some instances, the inability to generate a curve may indicate the absence of a particular nucleic acid analyte in a sample.

Signal processing steps of the instant disclosure will include one or more of signal acquisition (i.e., signal scan), detector background subtraction, match filtering, peak detection, intensity normalization, scale factor application, system background subtraction, crosstalk calibration, relative fluorescence unit calculation, and/or assay determination.

Figure 24:
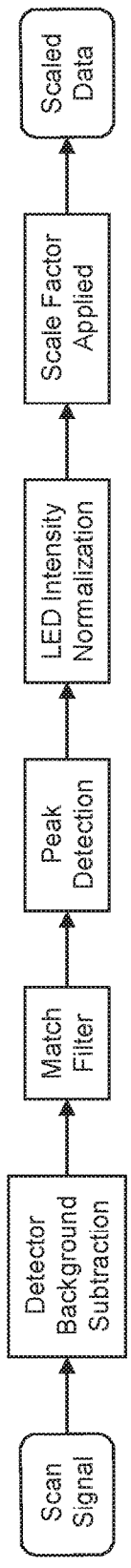
FIG. 24 provides a schematic representation of a signal processing pathway according to one embodiment as described herein.

In one embodiment, the signal processing steps of the system includes the signal processing pathway provided in FIG. 24 which includes signal acquisition (i.e., signal scan), detector background subtraction, match filtering, peak detection, intensity normalization and scale factor application to generate scaled data. Such processing may be performed, e.g., on an optical PCB including e.g., an optical master board.

In some instances, the signal processing pathway may further include system background subtraction, crosstalk calibration, relative fluorescence unit calculation, and assay determination. In some instances, such additional processing may or may not be performed on an optical master board and may e.g., take place on a processor separate from the optical master board.

In some instances, signal processing of the instant disclosure includes one or more signal acquisition (i.e., signal scan) steps. By signal scan step is meant the signal (produced from light emitted from the sample) detected on the measurement channel before going through any signal processing other than an amplifier. Such may represent the input to the entire signal processing pathway as measured on the measurement channel detectors, optionally after scaling with amplifiers. Each channel generally has a separate signal scan.

In some instances, signal processing of the instant disclosure includes one or more detector background subtraction steps. By detector background subtraction is meant the average signal when the illumination component (e.g., the respective LED(s) for a channel) are toggled off. Detector background may be measured at the beginning of each scan and detector background may be measured separately for each channel. In some instances, at the beginning of each scan, the background for each channel is measured as the average of the signal on the measurement channel when the LEDs are turned off in front of the optical dark target. In some instances, this background value may be subtracted from each obtained (i.e., scanned) data point.

In some instances, signal processing of the instant disclosure includes one or more match filtering steps. By match filtering is meant essentially noise filtering (e.g., filtering of high frequency noise) to match the measured data to the shape of a typical signal peak. In some instances, a single match filter is defined per module. In some instances, match filtering may be performed following detector background subtraction. In some instances, a match filter as used herein may be defined by a plurality of match filter taps or coefficients. The output of match filtering is filtered data.

In some instances, signal processing of the instant disclosure includes one or more peak detection steps. In some instances, following match filtering a peak detection algorithm may be applied to locate the maximum value within each reaction vessel window where a reaction vessel window is a window of encoder counts around the location of a signal peak for a given channel and position which defines the range of encoder counts in which the system searches for peaks. In one embodiment, each position has six reaction vessel windows, one per channel and because channels 1 and 4, 2 and 5, and 3 and 6 each share an optics sub-block, the reaction vessel (RV) windows for these channel pairs are the same. In some instances, a RV window halfwidth value may be used to define the width of all windows for all positions of a module. In some instances, the RV window serves to reduce data processing overhead by limiting the amount of data that needs to be checked for peaks.

In some instances, signal processing of the instant disclosure includes one or more intensity normalization steps including e.g., LED intensity normalization. In some instances, following peak detection, the detected peaks are divided by LED intensity used in the scan to correct for LED drift during an assay run. For example, at the beginning of each scan in front of the optical dark target, the LED Intensity for each channel is measured then, after the peaks are detected, the peaks are divided by the LED Intensity for the respective channel. In some instances, LED intensity normalization is performed on a scan by scan basis.

In some instances, signal processing of the instant disclosure includes one or more scale factor application steps. In some instances, following LED intensity normalization, the normalized data is multiplied by a scaling factor to generate scaled data. Scale factor application may be performed on a channel by channel basis where each channel has a calibrated scale factor, e.g., where the calibrated scale factor is determined such that the normalized/scaled data are comparable across their respective dynamic intensity ranges to saturation.

Figure 25:
FIG. 25 provides a schematic representation of a signal processing pathway according to one embodiment as described herein.

In some instances, signal processing of the instant disclosure includes the generation of scaled data. Scaled data, when produced from intensity normalized data, will correct for any variation in LED intensity from calibration during a protocol and allow comparison of data across a run and between channels of a run. In some instances, scaled data may be further processed. In one embodiment, scaled data is further processed through a signal processing pathway provided in FIG. 25 which includes system background subtraction on the scaled data to generate system background subtracted data, crosstalk correction application, relative fluorescence unit conversion, and analysis.

In some instances, signal processing of the instant disclosure includes one or more system background subtraction steps. In some instances, system background subtraction includes the subtraction of system background from the calibration for each of the channels and positions from the corresponding scaled data values for each scan. Such system background values may be generated in a variety of methods including but not limited to e.g., recording scaled data values for each channel in each position using reaction vessels loaded with a control buffer. In some instances, system background values may be determined periodically, including but not limited to e.g., once daily, once before starting a run, etc. In some instances, additional determinations of system background values may be performed including e.g., to compensate for potential variations in buffer, potential variations in reaction vessel material, etc.

In some instances, signal processing of the instant disclosure includes one or more crosstalk calibration or crosstalk correction steps. Such crosstalk correction corrects for crosstalk between the various dyes and channels. In some instances, e.g., where dyes with emission overlap are utilized in a method as herein described in a device having a plurality of optical blocks a crosstalk matrix may be generated and channel-to-channel crosstalk may be corrected for. For example, a reaction vessel containing a single dye at a known concentration may be scanned and the average scaled data, with system background subtracted, may be measured for each channel and the resultant values may be used to generate a crosstalk matrix. In some instances, a crosstalk matrix may be used to correct each measured value to remove any signal intensity due to crosstalk from another channel or dye and/or all other channels or dyes.

The emitted fluorescence intensity of various dyes is variable with temperature. Accordingly, in some instances, a crosstalk calibration matrix may take into account predicted changes in dye intensity over the applicable temperature range (e.g., from 30° C. to 65° C.). For example, in some instances, based on the assay being run and/or the temperature protocol used during amplification, a crosstalk correction factor may be used to adjust the crosstalk calibration. Predicted changes in dye intensity may be determined by any convenient method, including e.g., empirical testing of dye intensity over temperature ranges with or without associated curve fitting of such data. During data collection and/or subsequent signal processing, the known temperatures of a particular assay during cycling may be employed to select a crosstalk correction factor at particular temperatures for each dye used in the assay. A matrix of crosstalk correction factors across temperatures may allow for adjusting the crosstalk calibration based on specific dye combinations at certain temperatures.

Figure 26:
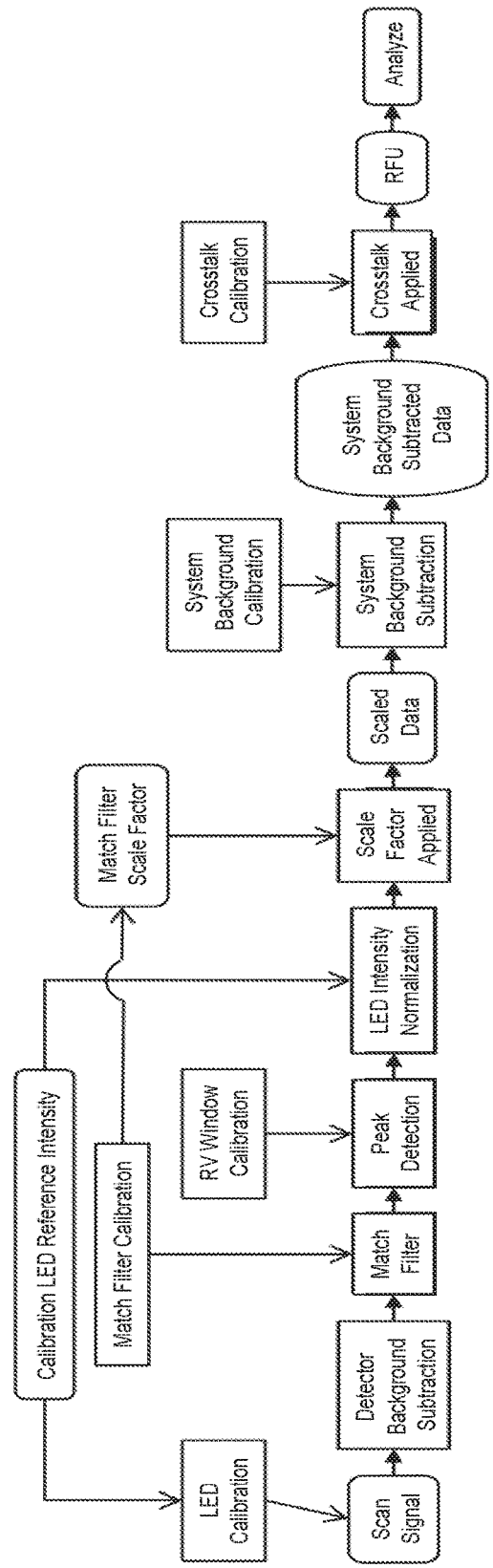
FIG. 26 depicts positions along a signal processing pathway that calibration measurements may be applied according to an embodiment as described herein.

Once reference calibration values are determined, e.g., from one or more calibration measurements as described herein, calibration may be applied to various points of one or more signal processing pathways where convenient and/ or appropriate. In one embodiment, various calibrations may be applied as indicated in FIG. 26.

Devices and Systems

The instant disclosure generally provides devices and systems for the amplification of nucleic acids in a reaction vessel and the analysis and monitoring of such amplification by optical measurements taken through the sidewall of the reaction vessel. The devices and systems disclosed herein may provide an amplification function or an analysis/monitoring function or may be integrated, providing both an amplification function and an analysis/monitoring function. Also provided are components of such devices and systems, including but not limited to e.g., a thermal block component, an optical block component, an illumination component and the like.

Nucleic Acid Amplification Devices

The instant disclosure provides thermal control devices useful in the amplification of nucleic acids. Such devices may be referred to as nucleic acid amplification devices and are often commonly referred to as thermocyclers.

Where electricity is employed to control thermal cycling, at a minimum, a thermocycler useful in nucleic acid amplification with include a thermal block, a thermoelectric cooler and a control unit, such components configured together to regulate the temperature of a reaction vessel in a controlled manner so as to cycle the reaction through multiple rounds of heating and cooling through a defined series of temperature steps.

A nucleic acid amplification device of the instant disclosure may include thermoregulatory components in addition to the thermal block and thermoelectric cooler including but not limited to e.g., a heatsink, a fan, a duct, a vent, etc. Two or more thermoregulatory components of a nucleic acid amplification device will generally be in thermal contact with one another. By "thermal contact" is meant that heat may flow from one component to the other, i.e., the components are not separated by a thermal insulator. Two components in thermal contact with one another may be in direct contact, i.e., direct physical contact. Alternatively, two components in thermal contact with one another may be in indirect contact including e.g., where one or more conductive materials between the two components places the two components in thermal contact with one another. For example, a thermal block and a thermoelectric cooler in thermal contact with one another may be in directed physical contact or may be in indirect contact, thermally joined by one or more conductive materials.

Conductive materials useful in thermally joining thermoregulatory components of the nucleic acid amplification devices as described herein include solids, semi-solids, semi-fluids and liquids that are sufficiently thermo-conductive to allow heat to readily flow between the components. A useful conductive material will generally, but not necessarily, have a thermal resistance that is less than that of the two or more components that it thermally joins. Conductive materials useful in thermally joining two components of the devices described herein include conductive metals and conductive non-metal solids as described herein. However, such conductive materials useful in thermally joining two components are not limited to solids any may include e.g., thermal greases, thermal adhesives, thermal gels, thermal coatings, thermal composites, encapsulated thermal materials (e.g., phase-change materials (e.g., encapsulated thermal liquids, etc.), and the like. In some instances, an adhesive used to join two components of a subject device or system (e.g., an epoxy) may serve as a conductive material between the two components.

The actual configuration of the thermal joining of two components with a conductive material will vary and may include e.g., where the entire interface between the two components is occupied or covered by the conductive material, where a portion of the interface between the two components is occupied or covered by the conductive material, where a majority of the interface between the two components is occupied or covered by the conductive material, where half of the interface between the two components is occupied or covered by the conductive material, where a minority of the interface between the two components is occupied or covered by the conductive material, etc.

In some instances, a conductive material that thermally joins two components may be in the form of a pad where the pad covers the entire interface between the two components. In other instances, a conductive material that thermally joins two components may be in the form of a pad where the pad covers only a portion of the interface between the two components. In instances where a pad is used that covers only a portion of the interface between the two components, in certain embodiments, multiple, i.e., a plurality of, pads may be used where the pads may be positioned such that there is space between the pads. In other instances, a plurality of pads may be arrayed such that there is essentially no space between the pads. Accordingly, where multiple pads are utilized the plurality of pads may collectively cover a portion of the interface between the components, a majority of the interface between the two components, a minority of the interface between the two components, or the entire interface between the two components.

Conductive solid materials useful in constructing thermoregulatory components and/or as a conductive material that thermally joins two or more thermoregulatory components include but are not limited to metals and/or metal alloys. Considerations that may be made considering the selection of a particular metal for use in a thermoregulatory component or as a conductive material that thermally joins two or more thermoregulatory components include but are not limited to the thermal conductivity of the metal and/or the thermal expansion of the metal. Such thermal properties of common metals that may find use in one or more components or to thermally join two or more components are as follows (thermal conductivity in British thermal unit per hour foot degree Fahrenheit (Btu/h×ft×° F.); thermal expansion in inch per inch per ° F.×$10^6$): Aluminum (136; 13.1), Antimony (120; NA), Brass (Yellow) (69.33; 11.2), Copper (231; 9.8), Gold (183; 7.9), Iron, Cast (46.33; 6), Lead, solid (20.39; 16.4), Nickel (52.4; 5.8), Platinum (41.36; 4.9), Silver (247.87; 10.8), Steel, mild (26.0-37.5; 6.7), Steel, Stainless 304 (8.09; 9.6), Steel, Stainless 430 (8.11; 6), Tin, solid (38.48; 13), Titanium 99.0% (12.65; 4.7), Tungsten (100.53; 2.5), Zinc (67.023; 22.1), Zirconium (145; 3.2). In some instances, useful metals or alloys include but are not limited to Aluminum, 2024, Temper-T351 (conductivity 143 W/m×deg. C), Aluminum, 2024, Temper-T4 (conductivity 121 W/m×deg. C), Aluminum, 5052, Temper-H32 (conductivity 138 W/m×deg. C), Aluminum, 5052, Temper-O (conductivity 144 W/m×deg. C), Aluminum, 6061, Temper-O (conductivity 180 W/m×deg. C), Aluminum, 6061, Temper-T4 (conductivity 154 W/m×deg. C), Aluminum, 6061, Temper-T6 (conductivity 167 W/m×deg. C), Aluminum, 7075, Temper-T6 (conductivity 130 W/m×deg. C), Aluminum, A356, Temper-T6 (conductivity 128 W/m×deg. C), Aluminum, Pure (conductivity 220 W/m×deg. C), Beryllium, Pure (conductivity 175 W/m×deg. C), Brass, Red, 85% Cu-15% Zn (conductivity 151 W/m×deg. C), Brass, Yellow, 65% Cu-35% Zn (conductivity 119 W/m×deg. C), Copper, Alloy, 11000 (conductivity 388 W/m×deg. C), Copper, Aluminum bronze, 95% Cu-5% Al (conductivity 83 W/m×deg. C), Copper, Brass, 70% Cu-30% Zn (conductivity 111 W/m×deg. C), Copper, Bronze, 75% Cu-25% Sn (conductivity 26 W/m×deg. C), Copper, Constantan, 60% Cu-40% Ni (conductivity 22.7 W/m×deg. C), Copper, Drawn Wire (conductivity 287 W/m×deg. C), Copper, German silver, 62% Cu-15% Ni-22% Zn (conductivity 24.9 W/m×deg. C), Copper, Pure (conductivity 386 W/m×deg. C), Copper, Red brass, 85% Cu-9% Sn-6% Zn (conductivity 61 W/m×deg. C), Gold, Pure (conductivity 318 W/m×deg. C), Invar, 64% Fe-35% Ni (conductivity 13.8 W/m×deg. C), Iron, Cast (conductivity 55 W/m×deg. C), Iron, Pure (conductivity 71.8 W/m×deg. C), Iron, Wrought, 0.5% C (conductivity 59 W/m×deg. C), Kovar, 54% Fe-29% Ni-17% Co (conductivity 16.3 W/m×deg. C), Lead, Pure (conductivity 35 W/m×deg. C), Magnesium, Mg—Al, Electrolytic, 8% Al-2% Zn (conductivity 66 W/m×deg. C), Magnesium, Pure (conductivity 171 W/m×deg. C), Molybdenum (conductivity 130 W/m×deg. C), Nichrome, 80% Ni-20% Cr (conductivity 12 W/m×deg. C), Nickel, Ni—Cr, 80% Ni-20% Cr (conductivity 12.6 W/m×deg. C), Nickel, Ni—Cr, 90% Ni-10% Cr (conductivity 17 W/m×deg. C), Nickel, Pure (conductivity 99 W/m×deg. C), Silver, Pure (conductivity 418 W/m×deg. C), Solder, Hard, 80% Au-20% Sn (conductivity 57 W/m×deg. C), Solder, Hard, 88% Au-12% Ge (conductivity 88 W/m×deg. C), Solder, Hard, 95% Au-3% Si (conductivity 94 W/m×deg. C), Solder, Soft, 60% Sn-40% Pb (conductivity 50 W/m×deg. C), Solder, Soft, 63% Sn-37% Pb (conductivity 51 W/m×deg. C), Solder, Soft, 92.5% Pb-2.5% Ag-5% In (conductivity 39 W/m×deg. C), Solder, Soft, 95% Pb-5% Sn (conductivity 32.3 W/m×deg. C), Steel, Carbon, 0.5% C (conductivity 54 W/m×deg. C), Steel, Carbon, 1.0% C (conductivity 43 W/m×deg. C), Steel, Carbon, 1.5% C (conductivity 36 W/m×deg. C), Steel, Chrome, Cr0% (conductivity 73 W/m×deg. C), Steel, Chrome, Cr1% (conductivity 61 W/m×deg. C), Steel, Chrome, Cr20% (conductivity 22 W/m×deg. C), Steel, Chrome, Cr5% (conductivity 40 W/m×deg. C), Steel, Chrome-Nickel, 18% Cr-8% Ni (conductivity 16.3 W/m×deg. C), Steel, Invar, 36% Ni (conductivity 10.7 W/m×deg. C), Steel, Nickel, Ni0% (conductivity 73 W/m×deg. C), Steel, Nickel, Ni20% (conductivity 19 W/m×deg. C), Steel, Nickel, Ni40% (conductivity 10 W/m×deg. C), Steel, Nickel, Ni80% (conductivity 35 W/m×deg. C), Steel, SAE 1010 (conductivity 59 W/m×deg. C), Steel, SAE 1010, Sheet (conductivity 63.9 W/m×deg. C), Steel, Stainless, 316 (conductivity 16.26 W/m×deg. C), Steel, Tungsten, W0% (conductivity 73 W/m×deg. C), Steel, Tungsten, W1% (conductivity 66 W/m×deg. C), Steel, Tungsten, W10% (conductivity 48 W/m×deg. C), Steel, Tungsten, W5% (conductivity 54 W/m×deg. C), Tin, Cast, Hammered (conductivity 62.5 W/m×deg. C), Tin, Pure (conductivity 64 W/m×deg. C), Titanium (conductivity 15.6 W/m×deg. C), Tungsten (conductivity 180 W/m×deg. C), Zinc, Pure (conductivity 112.2 W/m×deg. C), and the like.

Conductive solid materials useful in constructing thermoregulatory components and/or as a conductive material that thermally joins two or more thermoregulatory components include but are not limited to nonmetals. Considerations that may be made considering the selection of a particular nonmetal for use in a thermoregulatory component or as a conductive material that thermally joins two or more thermoregulatory components include but are not limited to the thermal conductivity of the nonmetal and/or the thermal expansion of the nonmetal. Useful nonmetal materials include but are not limited to e.g., carbon based materials and carbon containing materials (including engineered any synthetic materials) including but not limited to diamond, graphite, graphene, carbon nanotube, carbon fiber, etc. Thermal properties of such carbon based and carbon containing materials are well-known and include e.g., those described in e.g., Dasgupta et al. Journal of Composite Materials, 26 (1992) 2736-2758; Sweeting, Composites Part A: Applied Science and Manufacturing, 35 (2004) 933-938; Wetherhold et al., Journal of Composite Materials, 28 (1994) 1491-1498; Balandin, Nature Materials 10, (2011) 569-581; the disclosures of which are incorporated herein by reference in their entirety.

Physical joining of the components, including thermoregulatory components, of the subject nucleic acid amplification device may be achieved by a variety of means depending on the particular components to be joined. In certain instances, any convenient method of joining may find use including but not limited to fastening mediated by a mechanical fastener including e.g., a bolt (e.g., an anchor bolt), a captive fastener, a clamp (or cramp), a clasp, a clip, a flange, a grommet, a latch, a nail, a peg, a pin, a retaining ring, a rivet, a snap fastener, a staple, a strap, a threaded fastener (e.g., a captive threaded fastener, a nut, a screw, a threaded insert, a threaded rod, etc.), a tie, a toggle bolt, a wedge anchor, and the like. Such mechanical fasteners may join two components by various forces and combinations of forces including but not limited to e.g., frictional forces (e.g., sheer force), compression forces, tensile forces, and combinations thereof. Physical joining of the components the subject nucleic acid amplification device need not necessarily employ a fastener and may, e.g., involve the use of an adhesive, a weld, and the like. In some instances, a faster may be used in combination with a non-fastener means including but not limited to e.g., a faster and an adhesive, a fastener and a weld, etc. In other instances, a fastener may be used alone, i.e., essentially without any other fastening means, including e.g., without adhesive.

Fasteners useful in the devices described herein may be made out of various materials including but not limited to thermal conductive materials and non-thermal conductive materials. As such, useful materials for fasteners include metals and nonmetals, including conductive nonmetals and nonconductive nonmetals. In some instances, useful nonmetal fasteners include but are not limited to e.g., polymeric materials, e.g., plastics, ceramics (e.g., alumina ($Al_2O_3$), zirconia ($ZrO_2$), etc.), and the like.

In some instances, including where at least one of the two components to be joined is a thermoregulatory component the thermodynamic properties of the component (including e.g., thermal expansion) may be taken into account. For example, in some instances, a compression fitting, including e.g., a compression fitting mediated by a mechanical fastener, may join two thermoregulatory components that differ in their thermal expansion properties with sufficient compressive force, e.g., to prevent movement of the components under various temperature conditions and changes. However, is some instances, care should be taken to assure such compressive force is not excessive to e.g., to prevent warping of the components or cracking of the components, etc., under various temperature conditions and changes. In some instances, a conductive pad, as described herein, may find use in joining two thermoregulatory components having different thermal expansion properties.

When one or more fasteners are is used to join two or more thermoregulatory components under a compression force the overall compressive force between the two components will vary and may range e.g., from 20 to 500 pounds per square inch (psi) including but not limited to e.g., 20 to 500 psi, 30 to 500 psi, 40 to 500 psi, 50 to 500 psi, 60 to 500 psi, 70 to 500 psi, 80 to 500 psi, 90 to 500 psi, 100 to 500 psi, 100 to 450 psi, 100 to 400 psi, 100 to 350 psi, 100 to 300 psi, 100 to 250 psi, 100 to 200 psi, 110 to 200 psi, 120 to 200 psi, 130 to 200 psi, 140 to 200 psi, 100 to 190 psi, 100 to 180 psi, 100 to 170 psi, 100 to 160 psi, 70 to 300 psi, 80 to 290 psi, 90 to 280 psi, 100 to 270 psi, 110 to 260 psi, 120 to 250 psi, 130 to 240 psi, 140 to 230 psi, 70 to 200 psi, 80 to 190 psi, 90 to 180 psi, 100 to 170 psi, 110 to 160 psi, 120 to 160 psi, 130 to 160 psi, 140 to 160 psi, and the like. Such forces may be determined either theoretically through the use of mechanical force modeling or empirically by use of a force sensor, a force gauge or analytical testing (e.g., deformation testing, failure testing, etc.).

One application of nucleic acid amplification devices is in the monitoring of an amplification reaction during amplification to identify the presence of a target or template nucleic acid, which may in some instances be referred to herein as a "nucleic acid analyte" or simply "analyte". In some instances, a nucleic acid amplification device may find use in monitoring of an amplification reaction during amplification to quantify the amount of a target nucleic acid analyte in a sample, e.g., a biological sample. Accordingly, the nucleic acid amplification devices described herein may find use in the amplification required for real-time PCR applications as described herein.

Thermal Blocks

A thermal block of the instant disclosure provides a thermal mass to or from which heat is flowed in order to provide accurate control of the temperature of one or more reaction vessels in thermal contact with the block. This instant disclosure provides a multi-well block capable of simultaneous control of the temperature of multiple reaction vessels. In one embodiment, the thermal block is capable of simultaneous temperature control of two reaction vessels. However, thermal blocks are not limited to two reaction vessels and may, in certain instances, allow for the simultaneous temperature control of three or more, four or more, five or more, six or more, seven or more, eight or more, nine or more, ten or more, reaction vessels provided the thermal block is configured to contact each reaction vessel with essentially the same temperature.

Reaction vessels generally seat into a reaction vessel well of the thermal block where a reaction vessel well may be a depression in the thermal block that conforms to the outer shape of the reaction vessel. In some instances, a reaction vessel well may at least partially extend from the thermal block. In yet other instances, a reaction vessel well may make use of a combination of depression features and extension features to conform to the outer shape of the reaction vessel including e.g., where the top surface of the thermal block includes a raised flange or lip around the edge of the reaction vessel well such that the reaction vessel well is not flush with the top surface of the thermal block. In other instances, the reaction vessel well is flush with the top surface of the thermal block. In either instance, where the reaction vessel well is formed from a depression in the top of the thermal block or an extension from the top of the thermal block or a combination thereof the reaction vessel may be loaded vertically (i.e., from the top) into the reaction vessel well.

The reaction vessel well may be dimensioned to conform to the shape of the reaction vessel such that a majority of the reaction vessel remains in thermal contact with the reaction vessel well. Accordingly, where a reaction vessel is e.g., a commercially available reaction vessel (e.g., a commercially available PCR tube) or is dimensioned to match a commercially available reaction vessel the reaction vessel well may conform to the shape of a commercially available reaction vessel such that, upon vertical insertion into the reaction vessel, the majority of the reaction vessel and the reaction vessel well remain in thermal contact. In instances where a reaction vessel is of a custom design the reaction vessel well may conform to the shape of the custom designed vessel such that, upon vertical insertion into the reaction vessel, the majority of the reaction vessel and the reaction vessel well remain in thermal contact.

In certain instances, the reaction vessel well may be configured such that the sides, e.g., only the sides and not the bottom, of the reaction vessel well conforms to the shape of the reaction vessel. In such instances, upon insertion into the reaction vessel well, the sides of the reaction vessel well and not the bottom will remain in thermal contact with the reaction vessel well.

Although generally configured to conform to the shape of the reaction vessel, the reaction vessel well may, in some instances, have dimensions that purposefully do not conform to the shape of the reaction vessel. For example, in some instances, the reaction vessel well may have a circumference that conforms to the outer circumference of the reaction vessel (including where the reaction vessel is essentially conical, essentially a conical pyramid, or a combination thereof) but a vertical depth that is larger than the vertical dimension of the reaction vessel such that, upon insertion of the reaction vessel into the reaction vessel well, an empty space or cavity persists beneath the inserted reaction vessel. In some instances, such empty space may serve as a "reservoir" under an inserted reaction vessel, e.g., to collect any unintentional liquid (i.e., spillage, condensation, etc.) that may be adhered to the reaction vessel.

The reaction vessel wells of a thermal block of the instant disclosure may be oriented in relative position to one another within the thermal block such that the reaction vessel wells are subjected to essentially equal temperatures during thermal cycling. Accordingly, the reaction vessel wells may be evenly spaced from the center of the block including e.g., where the reaction vessel wells are equidistant from the vertical midline of the thermal block. Such thermal blocks with evenly spaced reaction vessels may be bilaterally symmetric, e.g., the thermal block has a vertical line of symmetry such that the right and left halves of the thermal block are mirror images.

The thermal block of the instant disclosure, although bilaterally symmetric, may be asymmetric other respects. For example, the thermal block may have a thermal transfer side of a different configuration or surface shape as compared to the non-thermal transfer side, where the "thermal transfer side" is defined as the side of the block where primary heat transfer takes place. In such instances, a thermal block of the instant disclosure may have a thermal transfer side that is essentially planar or flat and a non-thermal transfer side that is nonplanar or not flat, including but not limited to e.g., where the non-thermal transfer side comprises structural elements including but not limited to e.g., ridges which may provide structural rigidity to the thermal block.

In many embodiments, thermal transfer side of the thermal block is opposite non-thermal transfer side. As such, in many embodiments, the thermal block of the instant disclosure may be six sided with: (1) a thermal transfer side, (2) a non-thermal transfer side opposite the thermal transfer side, (3) a top side having openings for vertical insertion of the reaction vessel(s) into reaction vessel well(s), a (4) right side, a (5) left side, and (6) a bottom. In many instances, the right side, left side and bottom are thin and essentially featureless, with the exception of providing attachment points for particular components (including e.g., a support bar), making the a thermal transfer side, the non-thermal transfer side and the a top side the primary functional sides of the thermal block. Accordingly, in some instances, a thermal block of the instant disclosure includes a top side that is greater in area (as determined by the largest length and width dimensions of the top) than the bottom of the thermal block (as determined by the largest length and width dimensions of the bottom).

In such instances, the non-thermal transfer side may serve as the analysis side of the thermal block where the term "analysis side" is defined as the side of the block from which analysis of the reaction vessel(s) is performed. The analysis side of the thermal block may include analysis openings for the optical analysis of the reaction vessels. In some instances, the optical openings include one or more apertures in the reaction vessel well configured such that light may pass into, e.g., excitation light, and out of, e.g., emission light, the reaction vessel by way of the aperture. The position of an analysis aperture in a reaction vessel will vary and may include, e.g., where the aperture is configured for analysis at the side of the reaction vessel.

As will be understood through further description of the multi-reaction analysis systems and integrated systems described herein. The relative positioning of the thermal transfer side and the analysis side opposite each other on the thermal block allows for simultaneous thermal cycling and analysis of the reaction vessels.

In many embodiments, the overall shape of the thermal block provides for center mounting of the thermal block to other components of the nucleic acid amplification device. For example, in certain instances, the thermal block has a mounting hole centrally positioned on a face (i.e., the thermal transfer surface or surface opposite the thermal transfer surface) of the thermal block. As such, the mounting hole may be perpendicular to the planar axis of the thermal block (e.g., the mounting hole is positioned having a center axis perpendicular to the plane of the thermal transfer surface). In some instances, the central positioning of the mounting hole may provide certain functional benefits including but not limited to e.g., evenly distributed compression forces across the thermal block upon affixing the thermal block to other components with a compression fitting (e.g., limiting deformation of the block due to thermal expansion and contraction effects during thermal cycling).

In some instances, the reaction vessel wells may be positioned at equal distances from the central mounting hole, e.g., such that the thermal block is bilaterally symmetric on a vertical axis through the mounting hole. The thermal block may include structural features oriented around the central mounting hole including e.g., structural ridges the emanate radially from the central mounting hole. In some instances, the central mounting hole is positioned half way between the right and left sides of the thermal block. In some instances, the central mounting hole is positioned half way between the top and the bottom of the thermal block.

A thermal block of the instant disclosure may also have a temperature detection area configured for the application of a temperature sensor. Such a temperature detection are may be essentially flat to allow the flush (i.e., flat against) attachment of a flat sided temperature sensor to the thermal block. In some instances, a temperature detection area may be positioned proximal to a reaction vessel well such that the temperature reading at the temperature detection area serves as a proxy for the temperature of the reaction vessel. Accordingly, where a temperature detection area is used as a proxy for the temperature of the reaction vessel the area will be sufficiently close to the reaction vessel well including but not limited to e.g., less than 2 cm from the reaction vessel well. Any convenient position proximal to the reaction vessel well may find use as a temperature detection area for monitoring reaction temperature including but not limited to e.g., beneath the reaction vessel well, including but not limited to within 2 cm from the bottom of the reaction vessel well.

In some instances, a thermal block may include a separate temperature detection area positioned proximal to each reaction vessel well such that the temperature of each reaction vessel may be separately monitored. The size and shape of a temperature detection area on a thermal block will vary. In some instances, the temperature detection area may be dimensioned to receive a temperature sensor. In some instances, the temperature sensor area may include a recess that is essentially circular or half-circular. In some instances, the temperature sensor area may include an associated channel, including e.g., where the diameter of the temperature sensor area is essentially equal to the width of the channel (see e.g., the embodiment depicted in FIG. 1 having a temperature sensor area (104) that is essentially equal in diameter to the width of the corresponding channel (105)).

Figure 28:
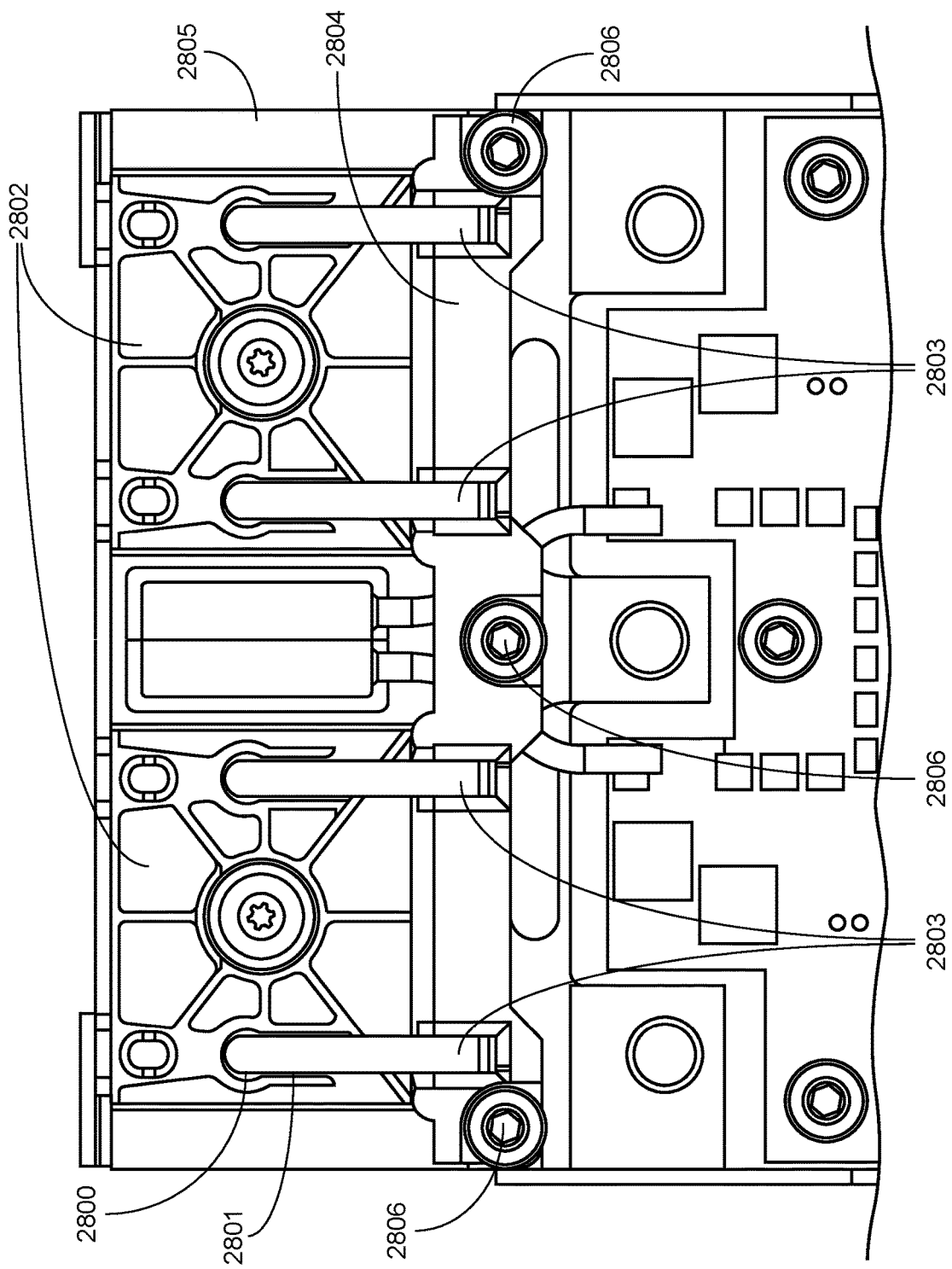
FIG. 28 depicts a frontal view of an embodiment of a nucleic acid amplification system with attached cantilever bar having a plurality of cantilever arms as described herein.

In some instances, the diameter of the temperature sensor area may be wider or narrower than the width of the associated channel. For example, in some instances, the temperature sensor area may be wider than the associated channel. Such an embodiment is depicted in FIG. 28 where e.g., the temperature sensor area (2800) has a diameter that is wider than the width of the associated channel (2801). In some instances, the temperature sensor area is dimensioned to receive a temperature sensor of a particular diameter or width and the associated channel has a width that is smaller than the diameter or width of the temperature sensor. In some instances, the temperature sensor employed has a diameter or width less than both the diameter of the temperature sensor area and any channel associated with the temperature sensor area.

The thermal block may be constructed of any convenient and appropriate thermally conductive material, including but not limited to metal including but not limited to e.g., one or more metal or metal alloy described herein including but not limited to e.g., aluminum. In some instances, the thermal mass of the thermal block may be kept relatively low, e.g., as in comparison to other thermal regulatory components of the system, to provide for rapid transitions between thermal cycling steps. The overall mass of the thermal block may vary and may range anywhere from e.g., 1 g to 10 g including but not limited to e.g., 1 g to 5 g, 1 g to 4.5 g, 1 g to 4.0 g, 1 g to 3.5 g, 1 g to 3.0 g, 1 g to 2.9 g, 1 g to 2.8 g, 1 g to 2.7 g, 1.5 g to 4 g, 1.5 g to 3.9 g, 1.5 g to 3.8 g, 1.5 g to 3.7 g, 1.5 g to 3.6 g, 1.5 g to 3.5 g, 1.5 g to 3.4 g, 1.5 g to 3.3 g, 1.5 g to 3.2 g., 1.5 g to 3.1 g, 1.5 g to 3.0 g, 1.5 g to 2.9 g, 1.5 g to 2.8 g, 2 g to 3.5 g, 2.5 g to 3.5 g, and the like.

One of more surfaces of the thermal block may be functionally coated or plated including but not limited to functional coating or plating to reduce corrosion, functional coating or plating to friction corrosion, and the like. Such functional coatings and/or platings will vary and may include e.g., metal plating, non-stick coating (e.g., dry lubricant), and the like. Examples of useful functional coatings and/or platings may include but are not limited to, electrolytic nickel plating, electroless nickel plating (e.g., Nye-Croloy (Nickel Chrome Plating), Sulfamate nickel, Kanigen, Nye-Kote), zinc electroplating, High Velocity Oxy-Fuel (HVOF) Combustive Spray, fluoropolymer-resin/lubricant blends, Xylan, molybdenum disulfide, epoxy coatings (including air dry and thermal cure coatings), phenolic coatings, phosphate ferrous metal coatings, polyurethane coatings, PTFE coatings, PPS/Ryton coatings, FEP coatings, PVDF/Dykor coatings, parylene coating, ECTFE/Halar coatings, ceramic epoxy coatings, and the like. In some instances, the entire thermal block may be coated or plated.

In some instances, a portion of the thermal block may be coated or plated, including but not limited to a majority of the thermal block, one or more surfaces of the thermal block, a minority of the thermal block, the surface of the reaction vessel well(s), the thermal transfer surface, the top surface, etc. In some instances, particular surfaces of the thermal block will not be coated or plated including but not limited to e.g., the thermal transfer surface.

In some instances, thermal blocks of the instant disclosure may be characterized in that, when combined with a particular TEC, the thermal block may have an empirical thermal slew rate of greater than 7° C./sec including but not limited to e.g., greater than 8° C./sec, greater than 9° C./sec, greater than 10° C./sec, etc., in cooling, heating or both cooling and heating. Such empirical thermal slew rates may be determined by a variety of methods including but not limited to e.g., "bang-bang" testing where heating and cooling are monitored while the component is cycled between minimum and maximum electrical currents. In some instances, empirical thermal slew rates may be determined within a temperature range or for two particular temperatures. For example, a thermal slew rate may be determined e.g., for heating between 25° C. and 95° C., for cooling between 25° C. and 95° C., for heating and cooling between 25° C. and 95° C., etc.

In some instances, the thermal slew rate of a thermal block as described herein may be expressed as an operating or applied thermal slew rate which is defined as the slew rate of the thermal block under normal operating conditions. In some instances, a thermal block of the instant disclosure may have an operating thermal slew rate of greater than 5° C./sec.

One embodiment of a thermal block according to the instant disclosure is depicted in FIG. 1 with the thermal transfer side of the thermal block oriented away from the viewer and the analysis side (100) oriented towards the viewer. The depicted thermal block is configured with a mounting hole (101) positioned with the central axis of the mounting hole oriented perpendicular to plane of the analysis side (100) of the block. The depicted thermal block contains two reaction vessel wells (102) each having a side aperture (103). The depicted thermal block further displays temperature monitoring areas (104) configured for the application of temperature sensors used to monitor the temperature of the thermal block in close proximity to the reaction vessels which can serve as a proxy for the reaction vessel temperature. The temperature monitoring areas (104) depicted further include associated channels (105).

Figure 2:
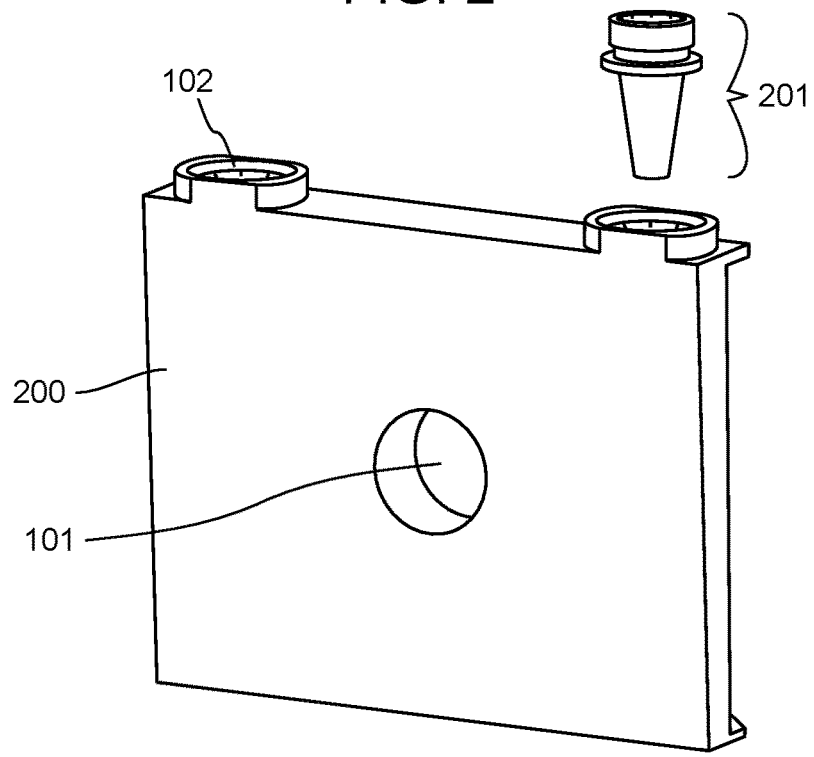
FIG. 2 provides an alternative view of the thermal block depicted in FIG. 1 and a corresponding reaction vessel for which the thermal block is configured.

FIG. 2 depicts the thermal transfer side (200) of the thermal block depicted in FIG. 1. From the thermal transfer side the reaction vessel wells (102) and mounting hole can be clearly seen (101). Also depicted is a reaction vessel (201) to which the depicted reaction vessel wells have been configured to conform. The reaction vessel is depicted in a vertical orientation above the reaction vessel well to generally indicate the vertical direction from which reaction vessels are loaded into the reaction vessel wells as shown in the particular embodiment.

Figure 3:
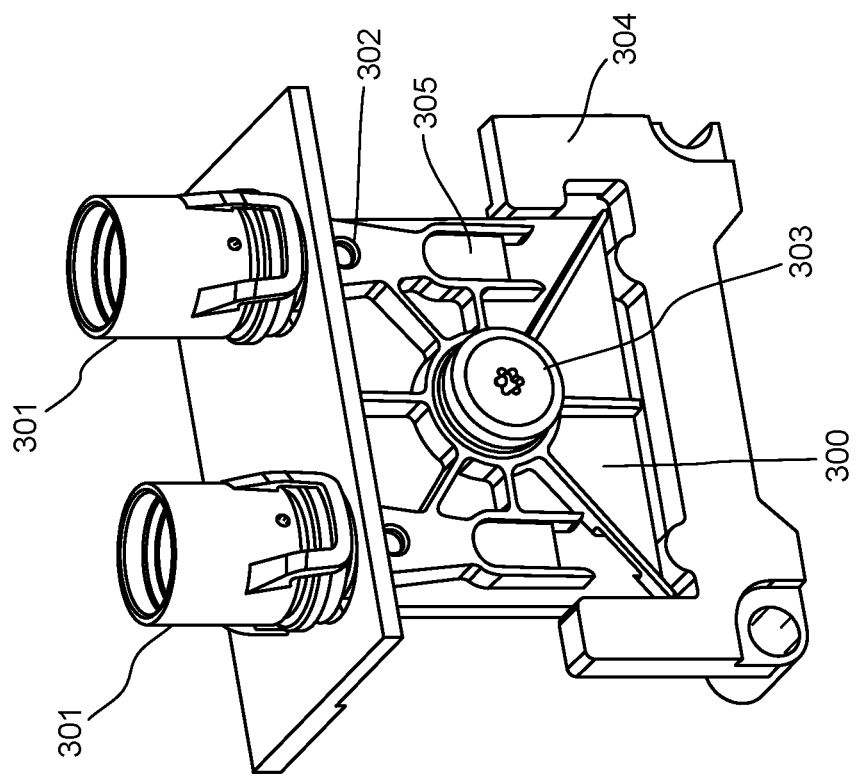
FIG. 3 depicts an embodiment of a partially mounted thermal block as described herein with capped reaction vessels loaded into the reaction vessel wells.

A thermal block (300) loaded with two capped reaction vessels is depicted in FIG. 3. The reaction vessel caps (301) can be seen protruding vertically from the reaction vessel which is recessed into the reaction vessel well. The analysis side of the thermal block is facing the viewer with a portion of a side aperture (302) of a reaction vessel well visible. The thermal block is depicted partially mounted with a mechanical fastener (303) present in the mounting hole and a support bar (304) positioned beneath the thermal block. Not pictured are the other thermoregulatory elements to which a thermal block of this particular embodiment would be mounted when in a complete nucleic acid amplification device configuration. The thermal block further depicts the presence of a temperature sensor (305) in the temperature monitoring area.

Thermoelectric Coolers

The nucleic acid amplification devices described herein generally include at least one thermoelectric cooler. A thermoelectric cooler (TEC) generally acts as a solid-state heat pump, functioning as a thermoelectric module that produces a heating, cooling or stabilization effect by running electrical energy through the device and transferring heat from one side of the device to the other against the temperature gradient. Thermoelectric coolers operate by the Peltier effect (or thermoelectric effect).

TECs generally have two sides such that when direct current (DC) flows through the device, heat is transferred from one side to the other, resulting in one side cooling while the other heats. Reversing the current results in an inversion of the thermal gradient such that the previously cooling side heats and the previously heating side cools. For sustained heating, cooling and/or temperature stabilization, the TEC may be placed in thermal contact with a heatsink.

In some embodiments, the TEC is made of ceramic materials including but not limited to e.g., Alumina, Beryllium Oxide, and Aluminum Nitride. In some instances, the TEC includes diced ceramic.

In many embodiments, the TEC may include a central mounting hole including where the central mounting hole is positioned with a central axis perpendicular to the primary plane of the TEC. In some instances, the central mounting hole of the TEC may be sized to correspond with the central mounting hole of a thermal block to which the TEC may be joined including but not limited to e.g., where the TEC and the thermal block have central mounting holes that are essentially equal in diameter. As such, in some instances, the central hole of the TEC will be the same or larger in diameter as compared to the diameter of a mechanical fastener used to join the TEC and the thermal block such that the mechanical fastener may pass through the central mounting hole and sufficiently join the TEC and the thermal block, e.g., a by compression force.

Figure 4:
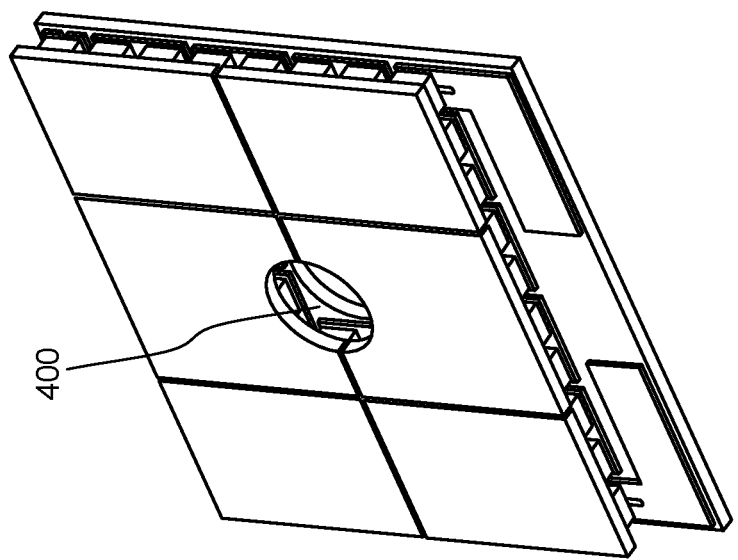
FIG. 4 depicts an embodiment of a thermoelectric cooler for use in a nucleic acid amplification device as described herein.

One embodiment of a TEC having a central mounding hole (400) is depicted in FIG. 4. The depicted TEC can be seen to have two sides or plates which, e.g., one of which would be positioned in thermal contact with the thermal transfer side of a thermal block and the other would be positioned in thermal contact with a heatsink as described herein. The two plates of a TEC may be different in the size in one dimension, as depicted, different in size in more than one dimension, or may be essentially equal in all dimensions.

Suitable thermoelectric coolers include but are not limited to e.g., those available from commercial suppliers including but not limited to e.g., Ferrotech Corp. (Bedford, NH), Marlow Industries, Inc. (Dallas, TX), TE Technology, Inc. (Traverse City, MI), and the like. In some instances, a TEC may be custom ordered to contain a central mounting hole. In other instances, a commercially available TEC may be modified to have a central mounting hole.

In some instances, a TEC used in a nucleic acid amplification device of the instant disclosure may be characterized as having a rapid thermal slew rate. In some instances, a TEC of a nucleic acid amplification device of the instant disclosure may have an empirical thermal slew rate of greater than 7° C./sec including but not limited to e.g., greater than 8° C./sec, greater than 9° C./sec, greater than 10° C./sec, etc., in cooling, heating or both cooling and heating. Such empirical thermal slew rates may be determined by a variety of methods including but not limited to e.g., "bang-bang" testing where heating and cooling are monitored while the component is cycled between minimum and maximum electrical currents. In some instances, empirical thermal slew rates may be determined within a temperature range or for two particular temperatures. For example, a thermal slew rate may be determined e.g., for heating between 25° C. and 95° C., for cooling between 25° C. and 95° C., for heating and cooling between 25° C. and 95° C., etc.

In some instances, the thermal slew rate of a TEC as described herein may be expressed as an operating or applied thermal slew rate which is defined as the slew rate of the TEC under normal operating conditions. In some instances, a TEC of the instant disclosure may have an operating thermal slew rate of greater than 5° C./sec.

Thermal Flow Components

The nucleic acid amplification devices described herein may also include additional thermal flow or heat transfer components configured to passively direct or actively control the flow of thermal energy within one or more components of the device. Thermal flow components that may be included in a nucleic acid amplification device as described herein may include but are not limited to e.g., a heatsink, a fan, a duct, and the like.

In many embodiments, the nucleic acid amplification devices described herein includes a heatsink. Any convenient heatsink configuration may find use in the nucleic acid amplification devices described herein. In some instances, a heatsink of the instant disclosure may be configured with a plurality of fins. For example, in some instances, a heatsink of the instant disclosure is configured with a plurality metal fins such that heat transferred to the heatsink is dissipated through the surface area of the fins. A heat sink of the instant disclosure will generally be constructed of a conductive material including but not limited to one or more of the conductive metals described herein including but not limited to e.g., copper.

Nucleic acid amplification devices, as described herein, may include a TEC in thermal contact with a heatsink such that heat generated by the TEC may be transferred to the heatsink and dissipated. In some instances, a nucleic acid amplification device of the instant disclosure may include a single heatsink in thermal contact with two or more TECs, including but not limited to e.g., where each TEC is in separate thermal contact with a thermal block.

In some instances, a heatsink of the instant disclosure is designed with one or more sockets configured for the attachment of a mechanical fastener. Such sockets may be configured for attachment in a variety of ways including but not limited to e.g., where one or more of the sockets is threaded, one or more of the sockets is configured with a compression fitting, one or more of the sockets is configured with a snap fitting, one or more of the sockets is notched, etc.

In some instances, a heatsink of the instant disclosure may be configured with two or more sockets each for the attachment of a thermal block and TEC pair. For example, a heatsink with two sockets may be connected to two thermal block/TEC pairs, each with a central mounting hole, for attachment to the heatsink using a mechanical fastener inserted through the mounting holes and secured to each socket. In some instances, thermal block/TEC pairs with central mounting holes are affixed to threaded sockets of a heatsink through the use of screw mechanical fasteners.

In one embodiment, as depicted in FIG. 5, a single heatsink (500) can be seen with two separate thermal blocks (501) mounted to the heatsink using separate mechanical fasteners (502). Parallel lines on the top surface of the heatsink depict the edges of many metal heat dissipation fins present in the heatsink. The TEC for each thermal block is mounted between the heatsink and the thermal block and is thus hidden from view. In this particular arrangement, four reaction vessels are affixed to the single heatsink and can be thermally cycled simultaneously.

Figure 6:
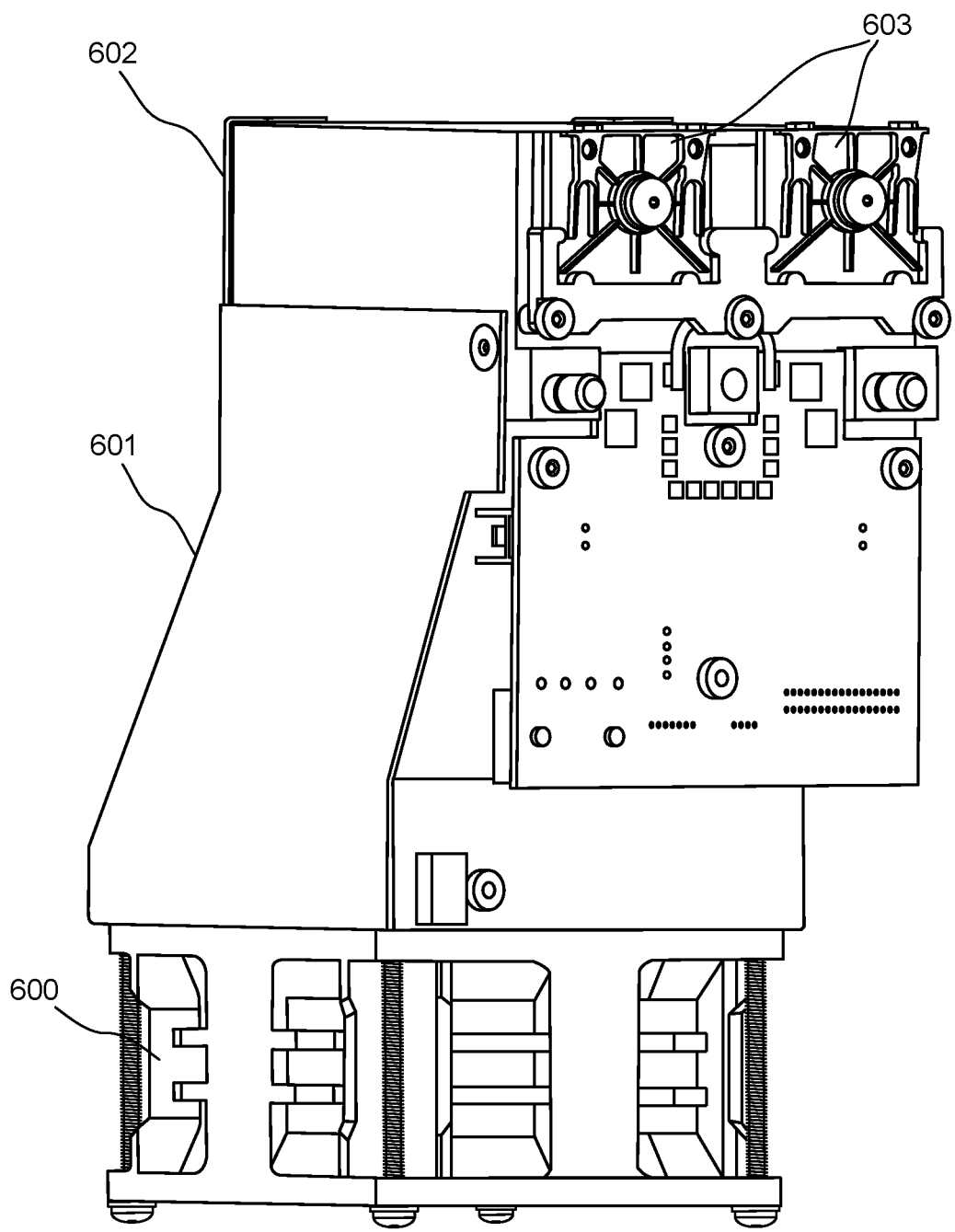
FIG. 6 depicts one embodiment of an assembled nucleic acid amplification device as described herein with associated thermoregulatory components.

In certain embodiments, e.g., as depicted in FIG. 6, a nucleic acid amplification device of the instant disclosure may further include a fan (600) and a duct (601) configured to draw or push air through the heatsink (602) and further assist in thermoregulation of the two thermal blocks (603) depicted in their fully mounted arrangement. For example, the fan may be adjusted on/off and/or the fan speed may be varied as needed to enhance the heat dissipation function of the heatsink. The fan direction may vary as desired and in some instances may be configured such that air is drawn from the heatsink down through the duct and out a vent beyond the fan. In some instances, the fan direction may be configured such that air is pushed through the duct up and out through the heatsink. Particular air flow directional configurations, such as inside-out flow direction, may limit the introduction of environmental contaminates into the device.

Figure 7:
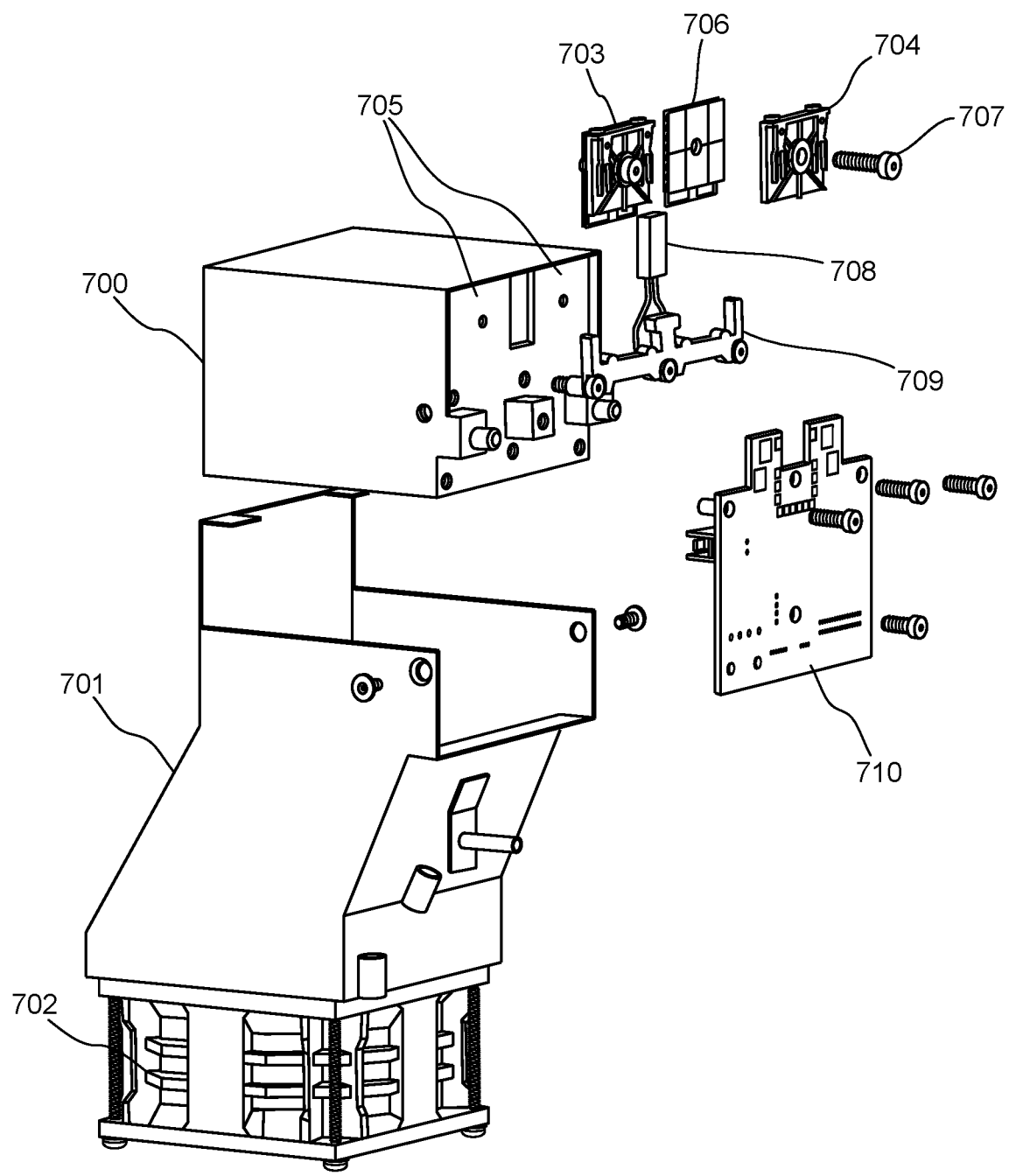
FIG. 7 provides a partially exploded view of the embodiment of an assembled nucleic acid amplification device with associated thermoregulatory components as depicted in FIG. 6.

FIG. 7 provides a partially exploded view of the embodiment depicted in FIG. 6 where the heatsink (700) can be seen exploded out from the duct (701) and fan (702), which remain joined. In addition, both thermal blocks (703 and 704) are exploded out from the heatsink (700) allowing a view of the mounting sockets (705) configured into the heatsink. One thermal block (703) is depicted in thermal contact with its corresponding TEC while the other thermal block (704) is exploded out from its TEC (706) and the mechanical fastener (707) used to secure the thermal block and TEC to the heatsink. Also depicted exploded out from the heatsink are the thermal cutoff (708), discussed in more detail below, the support bar (709) and the primary control board (710).

In addition to the thermoregulatory components utilized in assisting thermal control of the thermal cycler, the devices and systems described herein, including the analysis devices described below, may include additional thermoregulatory components, including but not limited to heatsinks, ducts, fans, vents and the like for managing heat generated during normal processes. For example, in some instances, a heat generating illumination unit may have an attached heatsink to assist in dissipating heat generated by the illumination unit. In other instances, a heat generating circuit board or processor may be in association with a fan to assist in dissipating heat generated by the circuit board or processor.

Sensors, Circuitry and Control

The nucleic acid amplification devices of the instant disclosure may include one or more sensors for receiving thermal measurement data. In some instances, a thermal sensor, e.g., a resistance temperature detector (RTD) may find use in measuring and/or monitoring the temperature of a surface the nucleic acid amplification device as described herein. For example, in some instances, an RTD may find use in monitoring the reaction vessel temperature, e.g., by measuring the temperature at a temperature monitoring area of the thermal block that is in close proximity to the reaction vessel.

RTDs appropriate for the applications, including the devices, systems and methods as described herein, will vary and may include but are not limited to e.g., 2 wire RTDs, 3 wire RTDs, 4 wire RTDs, thermistors, thermocouples, and the like.

Attachment of a RTD to a thermal block, e.g., at a temperature monitoring area, such that the RTD and the thermal block are and remain in thermal contact may be achieved by any convenient method. For example, in some instances, the RTD may be adhered to the thermal block using an adhesive, such as e.g., an epoxy.

Metals that undergo thermal cycling rapidly expand and contract. Accordingly, the maintenance of thermal contact between a sensor and a thermally cycling metal to which the sensor is mounted may be improved through the use of a cantilever bar mounted independently of the thermal cycling surface. For example, a cantilever arm may be mounted to a surface independent of the thermal cycling surface in such a configuration that that the tip of the cantilever arm applies pressure to the sensor such that the sensor maintains contact with the thermal cycling surface despite the rapid expansion and contraction of the metal of the thermal cycling surface. In certain embodiments, the cantilever arm is a separate element from the remaining components of the system and is mounted to a portion of the system and holds the RDP in close proximity to the thermal block.

Cantilever bars may be constructed of any convenient and appropriate material, including e.g., those materials that have flexible and/or elastic properties and/or those materials that resist creep from continuous applied force. In some instances, a cantilever bar may be constructed from a thermally and/or electrically non-conductive material. Useful materials for fashioning a cantilever bar, as described herein, include but are not limited to e.g., polymeric materials such as plastics, including e.g., polyaryletherketone (PAEK) family polymeric materials (e.g., polyether ether ketone (PEEK). A cantilever bar may be constructed from multiple different materials or may, in some instances, be constructed from a single material, such as e.g., only a PAEK family polymer such as e.g., PEEK. In some instances, a cantilever bar may be constructed of a first material and a cantilever arm extending from the cantilever bar may be constructed of a second material, e.g., as separate components. In some instances, the cantilever bar and a cantilever arm extending from the cantilever bar may be constructed of the same material or may be constructed as a single component. In some instances, a material used in constructing a cantilever bar or a cantilever arm of the present disclosure may have multiple beneficial properties including e.g., where the material used both prevents heat flow from the sensor and resists creep from continuous applied force.

A cantilever bar may be configured to have one or more cantilever arms extending from the cantilever bar, including but not limited to e.g., 2 or more cantilever arms, 3 or more cantilever arms, 4 or more cantilever arms, 2 cantilever arms, 3 cantilever arms, 4 cantilever arms, etc. A subject cantilever arm may extend from the cantilever bar at any convenient and appropriate angle including e.g., where the cantilever arm and the cantilever bar are perpendicular to one another.

A cantilever arm will generally have a tip which contacts a sensor and a base end that connects to or is borne from the cantilever bar. A cantilever bar may have one or more features (e.g., a hole, socket, flange, lip, etc.) for attaching the cantilever bar to a device or a specific component of a device, such as a component of the device that is independent of the thermal cycling component(s) of the device. In some instances, a cantilever arm may be directly attached to a device or a component of a device, such as a component of the device that is independent of the thermal cycling component(s) of the device, without the use of a cantilever bar. In such instances, the cantilever arm may include one or more features (e.g., a hole, socket, flange, lip, etc.) for direct attachment to the component of the device.

In some instances, a sensor that is contacted by the tip of a cantilever arm may be held in place (i.e., held in thermal contact with the thermal cycling component) solely by a cantilever arm. In some instances, despite the use of a cantilever arm, a sensor may nonetheless be otherwise adhered to the thermal cycling component by another means, e.g., through the use of an adhesive (e.g., an epoxy). In some cases, a cantilever arm may prevent loss of thermal contact between the sensor and the thermal cycling component upon failure of an adhesive. In some cases, despite structural failure of an adhesive used to attach a sensor to a thermal cycling component, a cantilever arm may provide the compression force necessary to maintain thermal contact between the sensor and the thermal cycling component and the adhesive, although structurally inadequate to maintain thermal contact between the sensor and the thermal cycling component in the absence of the cantilever arm, may provide a thermal conduit through which such thermal contact is maintained.

Figure 27:
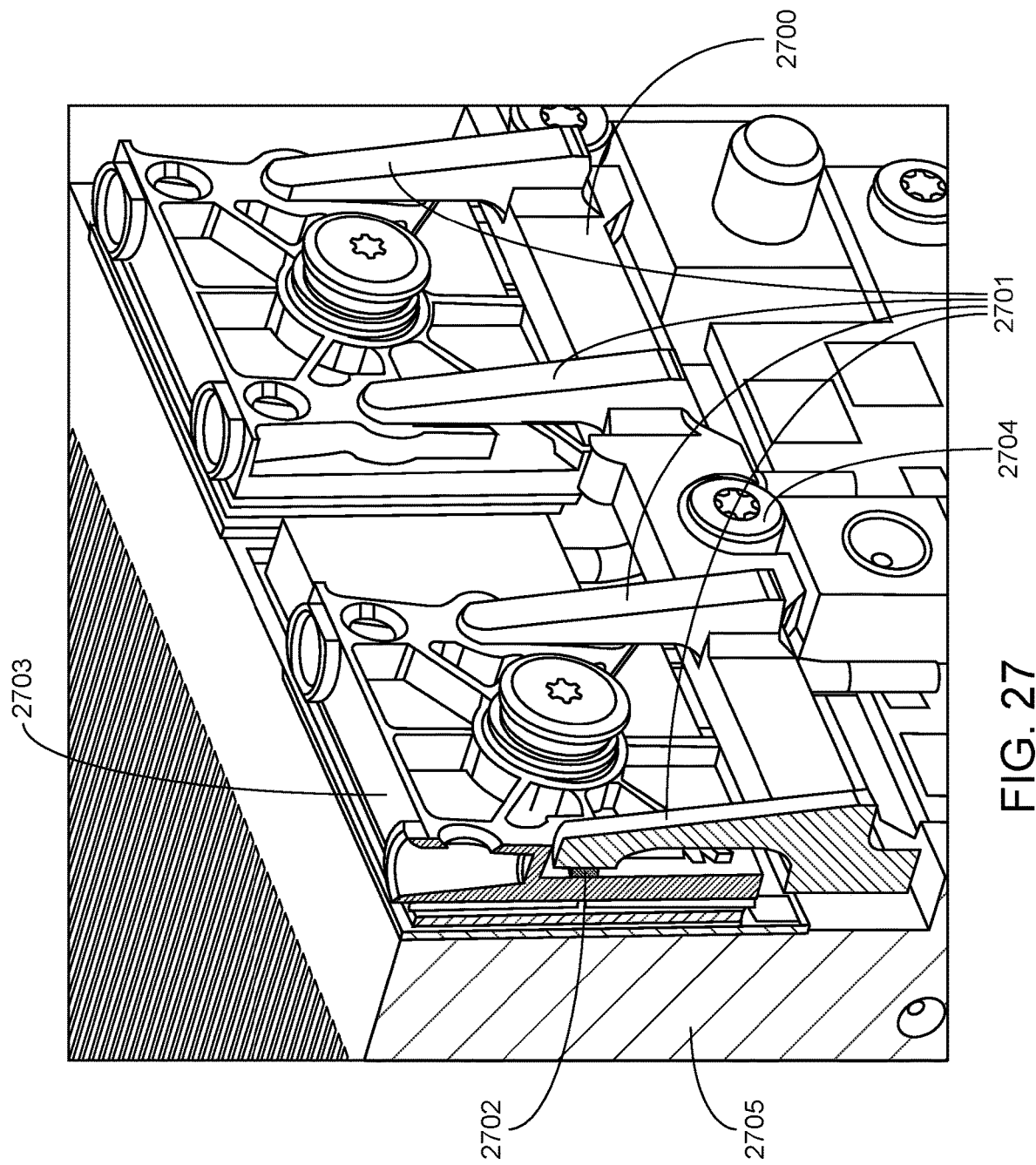
FIG. 27 depicts an embodiment of a nucleic acid amplification system with attached cantilever bar having a plurality of cantilever arms as described herein.

Turning to the embodiment depicted in FIG. 27, a cantilever bar (2700) may, in some instances, include four cantilever arms (2701) each having a tip that contacts a RTD (2702) present in a temperature monitoring area of the thermal block (2703). The left most cantilever arm (2701) depicted in FIG. 27 is shown in cross section, highlighting the shape of the cantilever arm which, in concert with the PEEK polymer material used to construct the cantilever arm, contributes to the elasticity or "spring action" of the cantilever arm, resulting in constant pressure on the RTD at the cantilever arm tip. As depicted, in some instances, the cantilever arm tip may, but need not necessarily, be flat. The cantilever bar may be affixed, e.g., via a fastener (2704), independently from the thermal cycling component (i.e., the thermal block), e.g., by attaching the cantilever bar to the heatsink (2705) as depicted.

Figure 29:
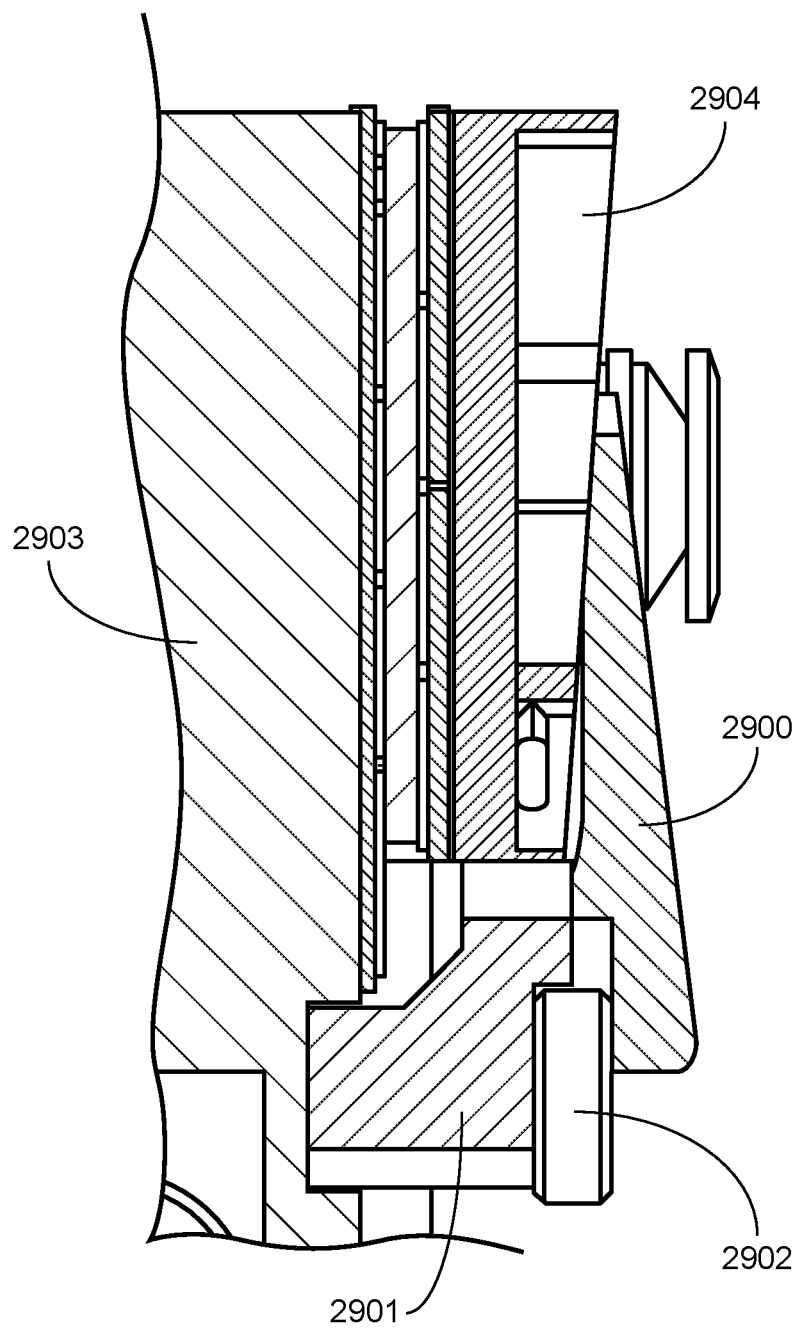
FIG. 29 depicts a profile view of an embodiment of a cantilever bar having a cantilever arm as described herein.

FIG. 28 provides a frontal view of an embodiment where thermal contact between RTDs and the thermal block is maintained through the use of a cantilever bar with a plurality of cantilever arms. As depicted in FIG. 28, each thermal block (2802), having a temperature monitoring area (2800) and associated channel (2801), has two attached RTDs (hidden) that are held in place by cantilever arms (2803) of a cantilever bar (2804). The subject cantilever bar is attached at the heat sink (2805) independently of the thermal blocks by three separate fasteners (2806). A profile view of one embodiment of a cantilever arm (2900) is provided in FIG. 29, displaying the cantilever bar (2901), fastener (2902) used to attach the cantilever bar to the heatsink (2903), and the associated thermal block (2904). As will be readily apparent to one of ordinary skill in the relevant art, the use of the subject cantilever arm and/or cantilever bar may not be limited to the particular described application of maintaining thermal contact between a RTD and a thermal block, but may also find use in maintaining thermal contact between sensors and thermal cycling components generally.

In some instances, one or more RTDs attached to the thermal block may provide thermal feedback to a PCB to control the temperature of the thermal block including e.g., to control the thermal cycling temperature(s) of the thermal block. In some instances, a thermal block having two attached RTDs, including but not limited to e.g., a thermal block having two reaction vessel wells each with an associated RTD, will be thermally regulated according to feedback from both attached RTDs including but not limited to e.g., where the temperature of the thermal block is determined as the temperature calculated as the average from the temperature measured at both RTDs.

In some instances, one or more RTDs of the thermal block may be calibrated including e.g., calibrated such that the temperature reading at the RTD is representative of the thermal block or representative of the reaction vessel wells of the thermal block. In addition, calibration of the RTD attached to the thermal block may serve to assure the thermal controller is capable of bringing the thermal block up to a correct temperature, down to a correct temperature, etc. RTD calibration serves to provide a known output with respect to a known temperature. In some instances, thermal block RTD calibration is performed by inserting a calibrated temperature sensor into the reaction vessel well and then recording the calibrated sensor's value and the RTD's output and determining if any difference exists between the two and if so to what degree the two measurements differ. If differences are detected, one or more components of the system may be adjusted or values processed by the system (e.g., temperature readings from the RTDs) may be adjusted to improve system functioning.

In other instances, an RTD may be used for general monitoring of the functioning of the nucleic acid amplification device or a component thereof. For example, in some instances, a RTD may find use in monitoring the temperature of the heatsink, e.g., as a means of detecting an abnormal temperature situation occurring in the device. In some instances, a RTD may find use in monitoring the temperature of one or more TECs, e.g., as a means of detecting an abnormal temperature situation occurring in the device. In some instances, a RTD may find use in monitoring the temperature of one or more thermal blocks, e.g., as a means of detecting an abnormal temperature situation occurring in the device.

Abnormal temperature situations that could be detected by system monitoring RTDs include but are not limited to e.g., insufficient heating, insufficient cooling, runaway heating, runaway cooling, temperature miscalibration, etc. "Runaway" conditions, including runaway heating and runaway cooling, as used herein generally refer to a loss of thermal control where the thermal output is the opposite of the desired condition, e.g., where the thermal output is continued heating when the system calls for cooling and vice versa.

In some instance, a device as described herein may include a "thermal cutoff" that deactivates the heating and/or cooling components of a device when certain abnormal conditions are met or a thermal error condition is detected including e.g., when a runaway condition is detected. Such deactivation may involve the cessation of power to the abnormally functioning component or a disconnection of the abnormally functioning component from the normal thermal control circuitry. Thermal cutoffs may be software controlled or hardware controlled switches or physical fuses. For example, in some embodiments, an RTD on a thermal block may, when a thermal error condition is detected, trigger a shutdown of the thermal block and associated components through a software controlled mechanism. In other embodiments, a physical fuse, e.g., as present on a heatsink, may rupture when a thermal error condition is reached triggering a shutdown of the heatsink and components connected to the heatsink.

A thermal cutoff may be independently triggered, e.g., when an internally monitored condition is met including e.g., a maximum temperature, a minimum temperature, a prolonged temperature, etc., or may be externally triggered including e.g., triggered by a circuit external to the thermal cutoff that receives monitoring information from one or more sensors external to the thermal cutoff. Any component of the herein described systems having a RTD may be programed to respond to a thermal error condition including for various purposes including but not limited to e.g., to indicate to the user that an error has occurred, to trigger a shutdown of one or more components of the system (e.g., to protect one or more components of the system, to protect a sample being run in the system, to protect parallel assays running in the system, etc.).

RTDs of the instant disclosure may function to send temperature monitoring data to one or more circuit boards to monitor the functioning of the device and/or the progression of the thermal cycling reaction. In some instances, data from the RTD is processed by one or more circuit boards to indicate a deviation in the system, including e.g., a thermal deviation from the programed thermal cycling program. In some instances, a detected deviation may signal a control unit to stop processing a particular sample or all samples being processed. In other instances, including e.g., where a deviation is within a safe range, the deviation may trigger circuitry to notify a user of the deviation. User notifications may vary and, regardless of the particular type of signal indicated, may include but are not limited to e.g., where the signal includes the use of a visual indicator (e.g., an indicator light, a notification on a graphical user interface, etc.), an or an audible alarm (e.g., a buzzer), and the like.

Figure 8:
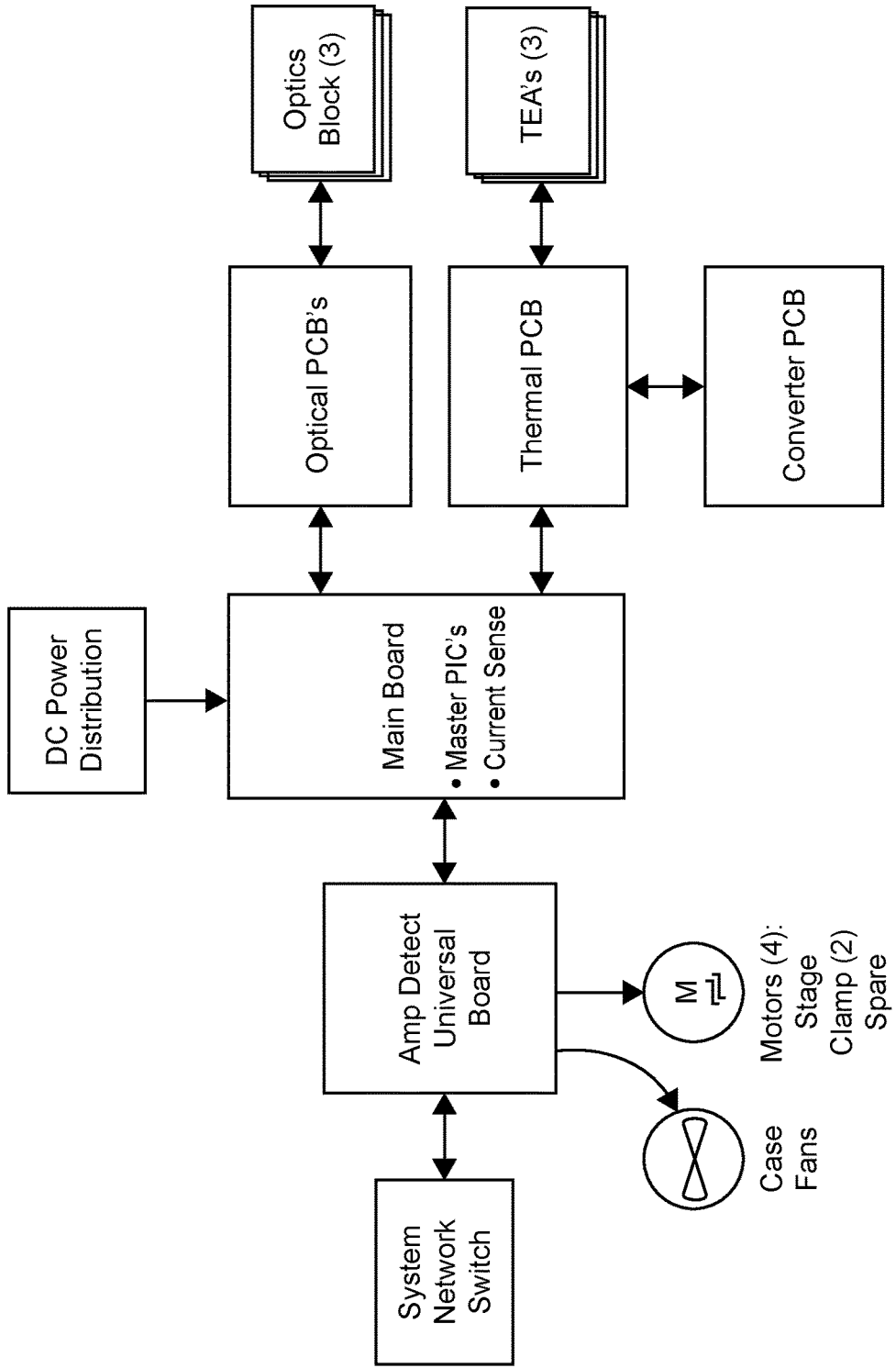
FIG. 8 provides a functional block diagram of an integrated amplification and detection unit as described herein.

Circuitry and/or data processing units of the instantly described nucleic acid amplification devices include control systems configured to control one or more components of the device including but not limited to e.g., one or more TECs, one or more fans, one or more sensors, etc. In some instances, circuitry of the instant disclosure may include component specific, or device specific circuit boards configured specifically to control a particular component or a particular device. For example, in some embodiments, a nucleic acid amplification device of the instant disclosure may include a thermal control circuit board configured (e.g., a thermal printed circuit board (thermal PCB)) where the thermal control circuit board is physically mounted to the nucleic acid amplification device as described herein or a component of the device. In other instances, the PCB responsible for thermal control may be mounted externally from the nucleic acid amplification device and the nucleic acid amplification device may include a mounted PCB that relays thermal information to the external thermal control PCB. Such specific circuit boards may be linked, directed or indirectly, to other components or circuits of the system, e.g., as depicted in the function block diagram of FIG. 8 representing an integrated system, described in more detail below, that includes a described nucleic acid amplification device.

Programing for circuits and/or components of the described devices may be embedded programing or may be programming stored in a computer readable storage medium including but not limited to an external storage medium or a non-transitory computer readable medium, and the like.

Multi-Reaction Analysis Devices

The instant disclosure includes multi-reaction analysis devices configured for the analysis of multiple amplification reaction vessels during the amplification reactions. For example, multi-reaction analysis devices of the instant disclosure allow for the monitoring of multiple real-time PCR reactions. Such multi-reaction analysis devices include optical components, conveyor components and signal detection/processing components wherein such components are configured for the frequent monitoring of multiple reaction vessels.

Optics

Multi-reaction analysis devices of the instant disclosure include optical components sufficient for the optical analysis of nucleic acid amplification reactions, including real-time PCR reactions, as described herein. Such optical components will include illumination components, including one or more excitation components, and components for receiving emission light from the reaction vessel.

As described herein a multi-reaction analysis device of the instant disclosure includes an optics detection unit where an optics detection unit includes an optical signal processor useful in processing received optical signals into relevant electrical signals that can be used in subsequent analyses and a plurality of optical blocks containing optical components sufficient for excitation of the sample and collection of emitted light from the excited sample which is passed to the optical signal processor.

Figure 9:
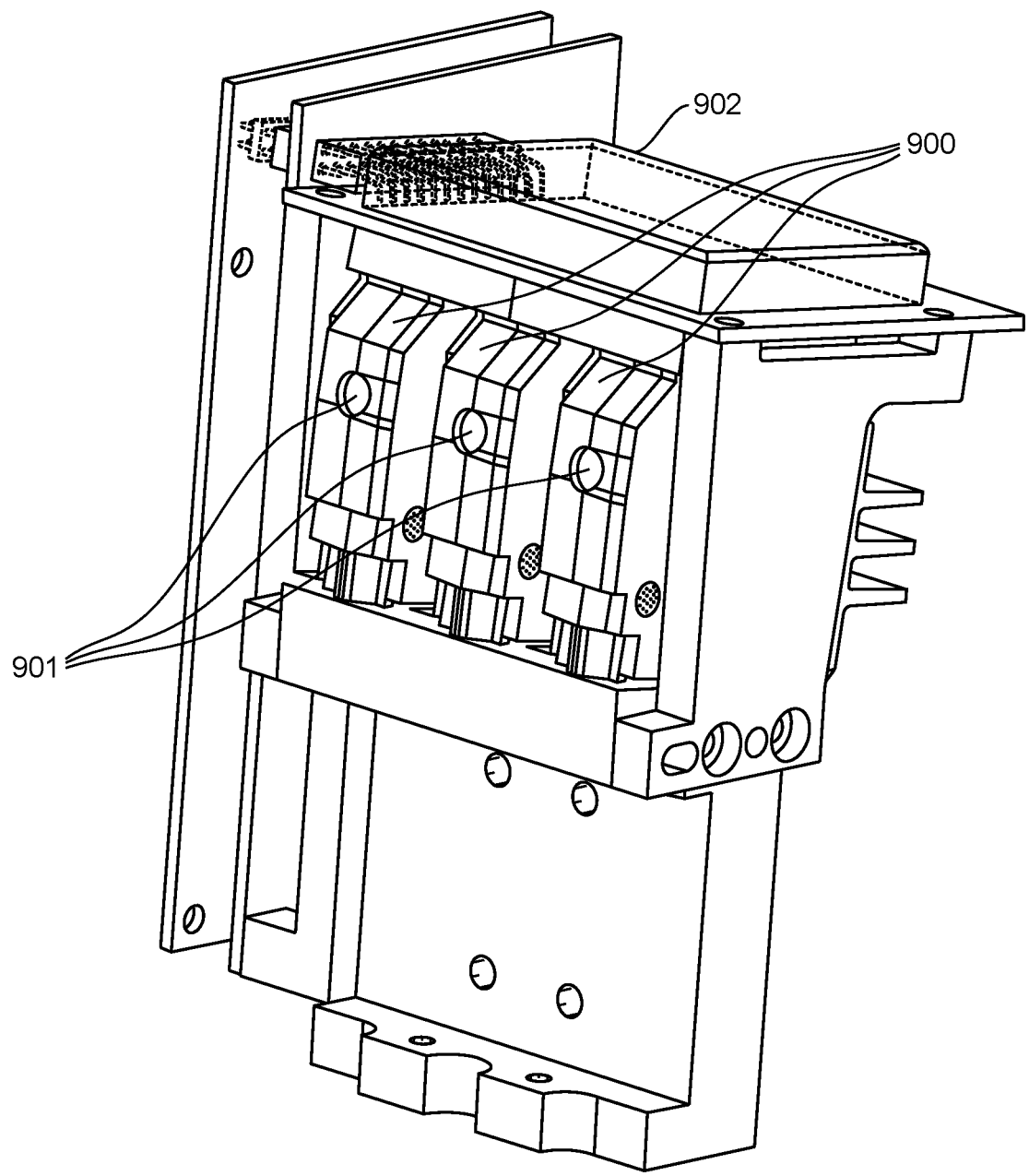
FIG. 9 depicts the optical aperture (i.e., optics block aperture) side of an embodiment of an optics detection unit as described herein.

In one embodiment, an optics detection unit, as depicted in FIG. 9, includes three optical blocks (900) in linear arrangement. Each optical block includes a side facing optical aperture (901), also referred to herein as a "optics block aperture", for passing excitation light from the optics block to the reaction vessel and passing emitted light from the reaction vessel back into the optics block. The optics detection unit also includes an optical signal processor (902) for processing the received emission light into electrical signals useful to performing an analysis of the amplification reaction as described herein.

Figure 10:
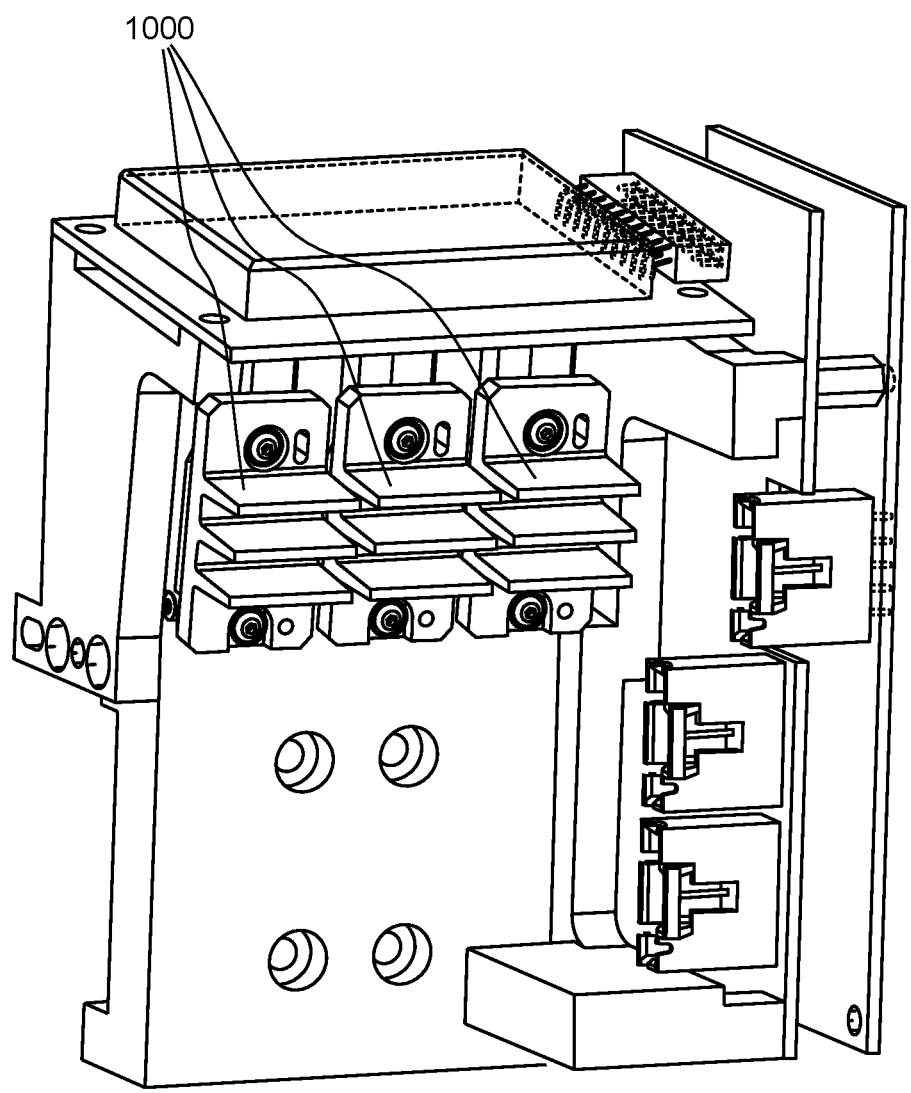
FIG. 10 provides an alternative view of the embodiment of the optics detection unit depicted in FIG. 9.

FIG. 10 provides a rear view of the optics detection unit depicted in FIG. 9, which shows the heatsinks (1000) positioned on the rear of each optics block adjacent to the illuminator component of each optics block. Such heatsinks in thermal contact with an optics block and, specifically the illumination unit of the optics block, serves to dissipate heat generated by the optics block, including but not limited to e.g., heat generated by the illumination unit of each optics block.

Illumination components of the instant disclosure include any excitation light source sufficient to generate excitation light that, after passing through the optics block, excites a fluorophore present in the amplification reaction which, in turn, produces emission light. Accordingly, the subject illumination components of the instant disclosure will vary and may include but are not limited to e.g., lamps, lasers, light emitting diodes (LED) emitters, and the like.

In some instances, the illumination component contains one or more LED emitters including but not limited to e.g., two or more LED emitters, three or more LED emitters, four or more LED emitters, one LED emitter, two LED emitters, three LED emitters, four LED emitters, etc. In some instances, an illumination component containing four LED emitters may contain two pairs of identical LEDs or one pair of LEDs of a first wavelength and a second pair of LEDs of a second wavelength. In instances where a plurality of LED emitters is employed, any useful arrangement of the LED emitters may find use in the illumination component including but not limited to e.g., linear arrangement, staggered arrangement, arrayed (e.g., "checker-board") arrangement, and the like. Useful LED emitters of the subject disclosure will vary, e.g., based on the particular assay to be performed by the device the optical, electrical or physical constraints of the device and the like.

LED emitters useful in an illumination component of the subject optics block may include but are not limited to e.g., LED emitters with a peak minimum wavelength (A) in nanometers (nm) of between 350 and 750 nm, including but not limited to e.g., between 350 and 450, between 350 and 400, between 400 and 450, between 450 and 550, between 450 and 500, between 500 and 550, between 550 and 650, between 550 and 600, between 600 and 650, between 650 and 750, between 650 and 700, between 700 and 750, about 400 nm, about 580 nm, about 470 nm, about 628 nm, about 528 nm, about 674 nm, and the like.

LED emitters useful in an illumination component of the subject optics block may include but are not limited to e.g., LED emitters with a peak maximum wavelength (A) in nanometers (nm) of between 350 and 750 nm, including but not limited to e.g., between 350 and 450, between 350 and 400, between 400 and 450, between 450 and 550, between 450 and 500, between 500 and 550, between 550 and 650, between 550 and 600, between 600 and 650, between 650 and 750, between 650 and 700, between 700 and 750, about 400 nm, about 405 nm, about 592 nm, about 480 nm, about 648 nm, about 542 nm, about 689 nm, and the like.

In some instances, an illumination component of an optics block as described herein may include two or more LED emitters. In optical blocks having two or more LED emitters each LED emitter may be defined as belonging to a channel including but not limited to e.g., a first channel, a second channel, etc. In some instances, three optical blocks each having two LED emitters may be referred to as having six channels, including where all six channels have an LED with a peak min/max of a different wavelength. In certain instances, the LED emitters of a multi-channel, multi-block system may be configured such that the average difference between the peak min/max wavelengths of each pair of LED emitters that share an optics block is maximized. For example, in such instances, six LED emitters having six different peak min/max wavelengths of A, B, C, X, Y, Z (where A<B<C<X<Y<Z) may be paired in optics blocks as, e.g., A and X, B and Y, C and Z. In such instances, where the average difference between the peak min/max wavelengths of each pair of LED emitters that share an optics block is maximized, overlap (i.e., crosstalk) between the emission wavelength of the LED emitters in each block may be minimized.

In some instances, an optical block may contain two LED emitters of different wavelengths where the distance between the different wavelengths will vary and may range from 5 nm to 300 nm or more including but not limited to e.g., at least 5 nm apart, at least 10 nm apart, at least 15 nm apart, at least 20 nm apart, at least 25 nm apart, at least 30 nm apart, at least 35 nm apart, at least 40 nm apart, at least 45 nm apart, at least 50 nm apart, at least 55 nm apart, at least 60 nm apart, at least 65 nm apart, at least 70 nm apart, at least 75 nm apart, at least 80 nm apart, at least 85 nm apart, at least 90 nm apart, at least 95 nm apart, at least 100 nm apart, at least 105 nm apart, at least 110 nm apart, at least 115 nm apart, at least 120 nm apart, at least 125 nm apart, at least 130 nm apart, at least 135 nm apart, at least 140 nm apart, at least 145 nm apart, at least 150 nm apart, at least 155 nm apart, at least 160 nm apart, at least 165 nm apart, at least 170 nm apart, at least 175 nm apart, at least 180 nm apart, at least 185 nm apart, at least 190 nm apart, at least 195 nm apart, at least 200 nm apart, not more than 300 nm apart, not more than 290 nm apart, not more than 280 nm apart, not more than 270 nm apart, not more than 260 nm apart, not more than 250 nm apart, not more than 240 nm apart, not more than 230 nm apart, not more than 220 nm apart, not more than 210 nm apart, not more than 200 nm apart, not more than 190 nm apart, not more than 180 nm apart, not more than 170 nm apart, not more than 160 nm apart, not more than 150 nm apart, not more than 140 nm apart, not more than 130 nm apart, not more than 120 nm apart, not more than 110 nm apart, not more than 100 nm apart, etc.

In some instances, LED emitters of the subject disclosure may be capable of being toggled (i.e., capable being turned on and off, including turned on/off repeatedly). In some instances, the wiring circuitry of an optics block having two or more LED emitters is configured or the programing controlling such an optic block is configured such that only one LED emitter may be toggled on at a time. In such instances, when a first LED emitter of an optic block is toggled on the second LED emitter of the optic block is toggled off and vice versa.

In some instances, the toggling of LED emitters of an optic block includes a time period where neither LED emitter of the optic block is toggled on. In some instances, such a time period where neither LED emitter of the optic block is toggled on is between toggling the toggling off of a first emitter and the toggling on of a second emitter.

LEDs of the disclosed multi-reaction analysis devices may include physical or electrical components and/or configurations allowing for use or one or more of the noise reduction methods described herein, including but not limited to e.g., components and/or configurations for time division multiplexing, components and/or configurations for frequency division multiplexing, components and/or configurations for spatial separation, and the like.

Figure 11:
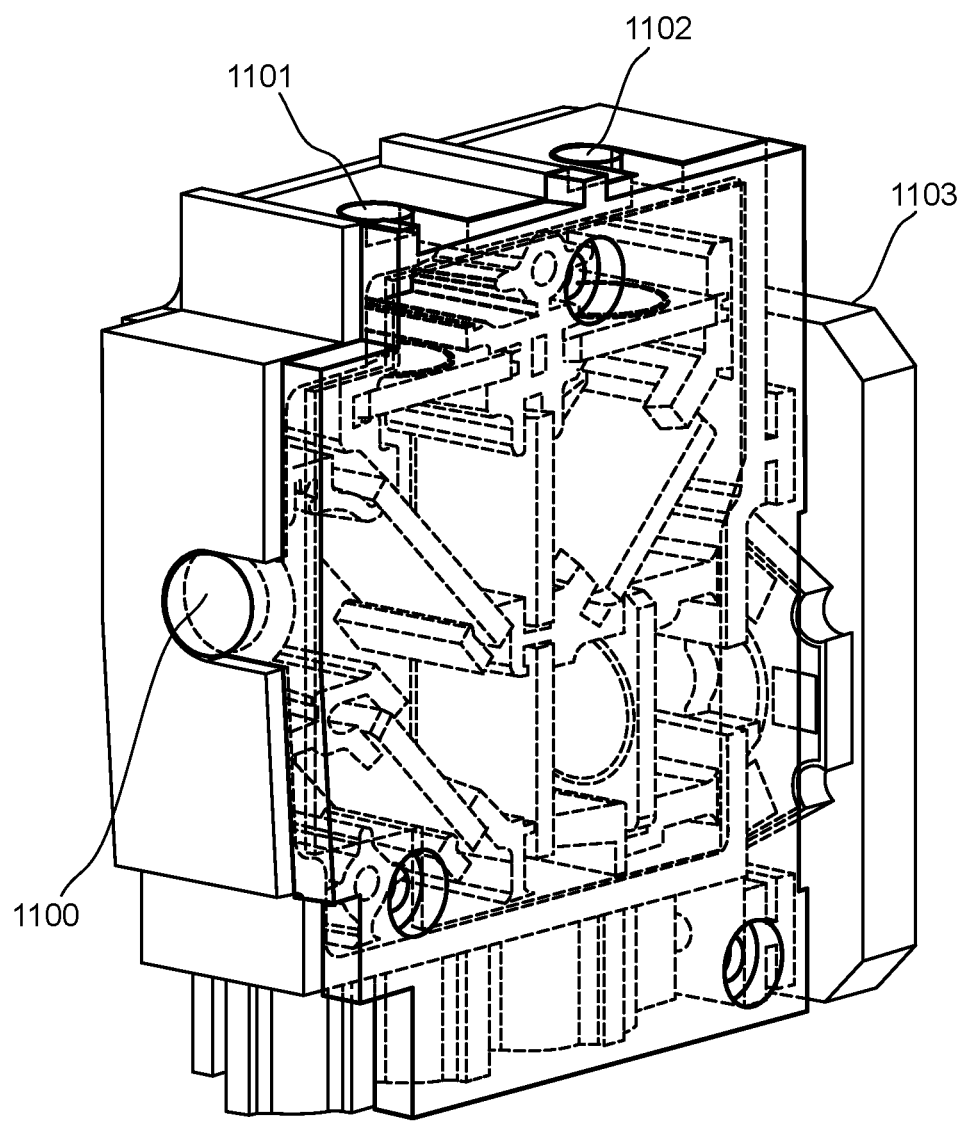
FIG. 11 provides an internal view of an embodiment of an optical block as described herein.

Optics blocks of the instant disclosure will include a variety of optical elements including but not limited to e.g., lenses, optical filters, mirrors (including e.g., dichroic mirrors), apertures, etc. For example, in one embodiment depicted in FIG. 11, an optics block of the instant disclosure includes an optics block aperture (1100) allowing excitation light (generated by the LED unit (1103)) to pass to the reaction vessel and emission light to pass back to the optics block, a reference channel aperture (1101) allowing light to pass from the optics block to the signal processing unit in the reference channel, a measurement channel aperture (1102) allowing light to pass from the optics block to the signal processing unit in the measurement channel.

Figure 12:
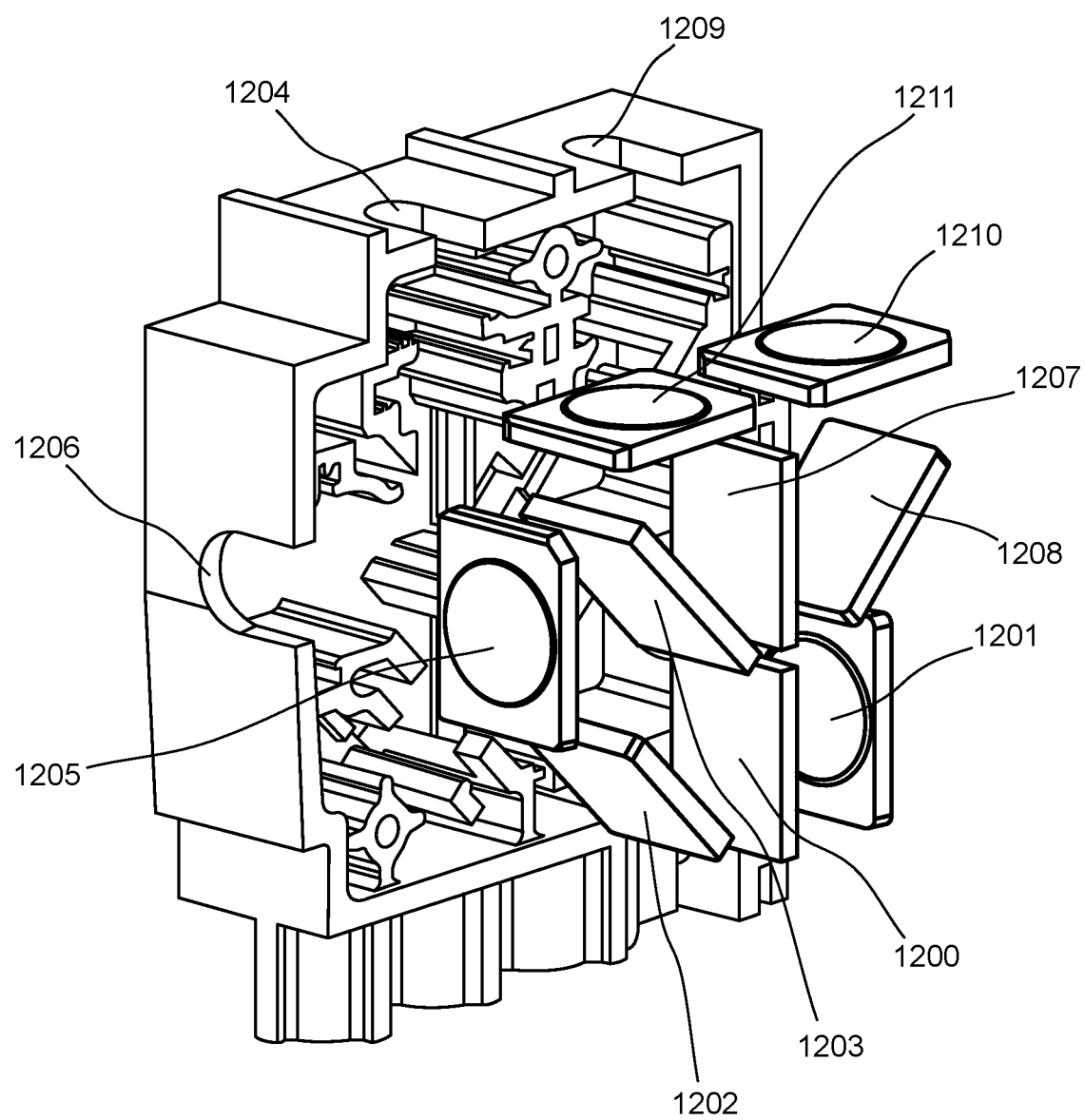
FIG. 12 provides an exploded view of the internal components of an embodiment of an optical block as described herein.

FIG. 12 provides an exploded view of the optical elements according to one embodiment of an optics block the instant disclosure. Such optical elements include illumination filters, detection filters, lenses and minors. The arrangement of the optical elements within the optics block may be sufficient to generate measurement and reference light paths including e.g., measurement and reference light paths as depicted in FIG. 13. Along the excitation light path to the measurement channel aperture, an optics block of the instant disclosure may include a first lens (1200) positioned proximal to the illumination component aperture, referred to herein as a illumination aperture lens, through which the excitation light from the illumination component passes. Illumination light passes from the illumination aperture lens to a illumination filter (1201) and to a first mirror (1202), referred to herein as the excitation light mirror, which deflects the excitation light upward towards a dichroic mirror (1203) and the reference channel aperture (1204). Excitation light below a wavelength threshold of the dichroic mirror is redirected through the optics block aperture lens (1205) and out the optics block aperture (1206), e.g., towards a reaction vessel.

Emission light, e.g., from a reaction vessel or a control surface such as a dark target, proceeds through the optics block aperture (1206) and the optics block aperture lens (1205). Emission light above the threshold wavelength of the dichroic mirror (1203) proceeds through the dichroic mirror towards the detection filter (1207). Emission light passing through the detection filter (1207) is redirected by a second mirror (1208), referred to herein as the detection channel mirror, up towards the detection (i.e., measurement) channel aperture (1209). After passing through the detection channel aperture lens (1210), emission light proceeds through the detection channel aperture (1209), e.g., into a measurement detector as part of or coupled to an optical signal processor. Light in the reference channel, including e.g., illumination light configured to pass vertically through the dichroic mirror (1203), stray light within the optical block, or combinations thereof and the like, proceeds up through the reference channel aperture lens (1211) and out the reference channel aperture (1204), e.g., into a reference detector as part of or coupled to an optical signal processor.

The arrangement of the optical elements within the optics block is not limited to those arrangements specifically depicted and may vary provided the necessary elements for producing the described light paths are included and sufficient to generate, pass and filter excitation and emission light as described herein.

Illumination filters useful in an optics block of the instant disclosure include but are not limited to e.g., illuminations filters having a center wavelength (CWL) in nanometers (nm) between 350 and 750 nm, including but not limited to e.g., between 350 and 450, between 350 and 400, between 400 and 450, between 450 and 550, between 450 and 500, between 500 and 550, between 550 and 650, between 550 and 600, between 600 and 650, between 650 and 750, between 650 and 700, between 700 and 750, about 409 nm, about 583 nm, about 475 nm, about 638 nm, about 535 nm, about 690 nm, and the like. Illumination filters useful in an optics block of the instant disclosure also include but are not limited to e.g., illuminations filters having a full width have maximum (FWHM) in nm ranging from 5 nm to 100 nm, including but not limited to e.g., about 5 nm to 10 nm, about 10 nm to 15 nm, about 15 nm to 20 nm, about 20 nm to 25 nm, about 25 nm to 30 nm, about 30 nm to 35 nm, about 35 nm to 40 nm, about 40 nm to 45 nm, about 45 nm to 50 nm, about 50 nm to 55 nm, about 55 nm to 60 nm, about 60 nm to 65 nm, about 65 nm to 70 nm, about 70 nm to 75 nm, about 75 nm to 80 nm, about 80 nm to 85 nm, about 85 nm to 90 nm, about 90 nm to 95 nm, about 95 nm to 100 nm, about 10 nm to 90 nm, about 10 nm to 80 nm, about 10 nm to 70 nm, about 10 nm to 60 nm, about 10 nm to 50 nm, about 10 nm to 40 nm, about 10 nm to 30 nm, about 10 nm to 20 nm, about 20 nm to 90 nm, about 30 nm to 90 nm, about 40 nm to 90 nm, about 50 nm to 90 nm, about 60 nm to 90 nm, about 70 nm to 90 nm, about 80 nm to 90 nm, 65 nm, 22 nm, 36 nm, 24 nm, 18 nm, 25 nm, and the like.

In some instances an illumination filter useful in an optics block as described herein may be characterized in having a particular combination of CWL and FWHM, including e.g., combinations of the CWL and the FWHM described above. For example, in some instances an illumination filter of the subject disclosure may be characterized as having a 409 nm CWL and a 65 nm FWHM, 583 nm CWL and a 22 nm FWHM, 475 nm CWL and a 36 nm FWHM, 638 nm CWL and a 24 nm FWHM, 535 nm CWL and a 18 nm FWHM, 690 nm CWL and a 25 nm FWHM, and the like.

Detection filters useful in an optics block of the instant disclosure include but are not limited to e.g., detection filters having a center wavelength (CWL) in nanometers (nm) between 350 and 750 nm, including but not limited to e.g., between 350 and 450, between 350 and 400, between 400 and 450, between 450 and 550, between 450 and 500, between 500 and 550, between 550 and 650, between 550 and 600, between 600 and 650, between 650 and 750, between 650 and 700, between 700 and 750, about 490 nm, about 617 nm, about 524 nm, about 673 nm, about 565 nm, about 715 and the like. Detection filters useful in an optics block of the instant disclosure also include but are not limited to e.g., detection filters having a full width have maximum (FWHM) in nm ranging from 5 nm to 100 nm, including but not limited to e.g., about 5 nm to 10 nm, about 10 nm to 15 nm, about 15 nm to 20 nm, about 20 nm to 25 nm, about 25 nm to 30 nm, about 30 nm to 35 nm, about 35 nm to 40 nm, about 40 nm to 45 nm, about 45 nm to 50 nm, about 50 nm to 55 nm, about 55 nm to 60 nm, about 60 nm to 65 nm, about 65 nm to 70 nm, about 70 nm to 75 nm, about 75 nm to 80 nm, about 80 nm to 85 nm, about 85 nm to 90 nm, about 90 nm to 95 nm, about 95 nm to 100 nm, about 10 nm to 90 nm, about 10 nm to 80 nm, about 10 nm to 70 nm, about 10 nm to 60 nm, about 10 nm to 50 nm, about 10 nm to 40 nm, about 10 nm to 30 nm, about 10 nm to 20 nm, about 20 nm to 90 nm, about 30 nm to 90 nm, about 40 nm to 90 nm, about 50 nm to 90 nm, about 60 nm to 90 nm, about 70 nm to 90 nm, about 80 nm to 90 nm, 42 nm, 22 nm, 24 nm, 20 nm, 18 nm, 36 nm, and the like.

In some instances an illumination filter useful in an optics block as described herein may be characterized in having a particular combination of CWL and FWHM, including e.g., combinations of the CWL and the FWHM described above. For example, in some instances an illumination filter of the subject disclosure may be characterized as having a 490 nm CWL and a 42 nm FWHM, 617 nm CWL and a 22 nm FWHM, 524 nm CWL and a 24 nm FWHM, 673 nm CWL and a 20 nm FWHM, 565 nm CWL and a 18 nm FWHM, 715 nm CWL and a 36 nm FWHM, and the like.

In certain instances, the devices and systems described herein may include an optical component external to the optical analysis unit where such external components are useful in, e.g., making calibration measurements and/or measurements used in determining proper functioning of the system or device.

In other instances, an external optical component may include a dark target, wherein a "dark target" is a darkly colored (i.e., black) component of the system or device from which a "dark measurement" may be made. Such dark measurements may be employed for calibration according to the methods as described herein, where an optical measurement is taken with the optics block aperture aligned to the dark target and a calibration is applied to the system based on the dark target measurement. Any convenient and appropriate optically dark element may be employed as a dark target including but not limited to e.g., black polycarbonate, black plastic, and the like.

Figure 17:
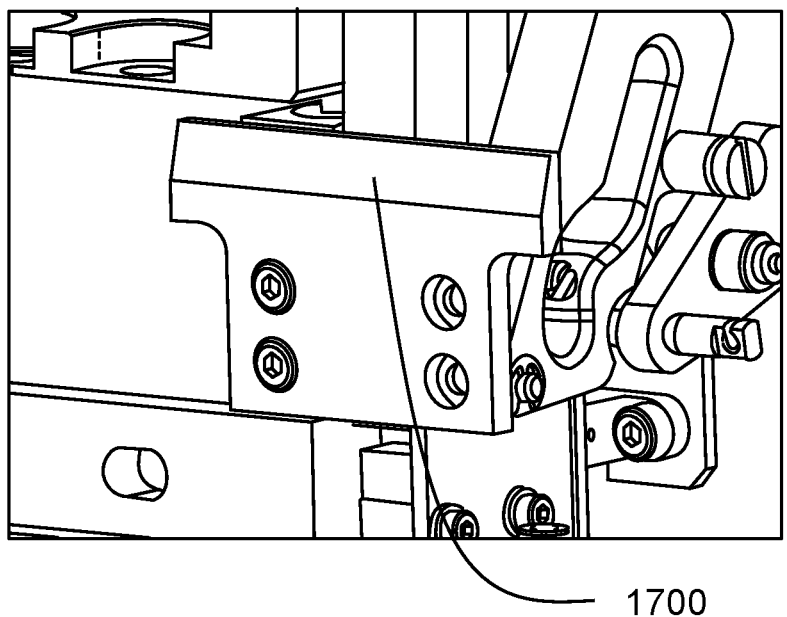
FIG. 17 depicts a dark target according to an embodiment of the instant disclosure.
Figure 18:
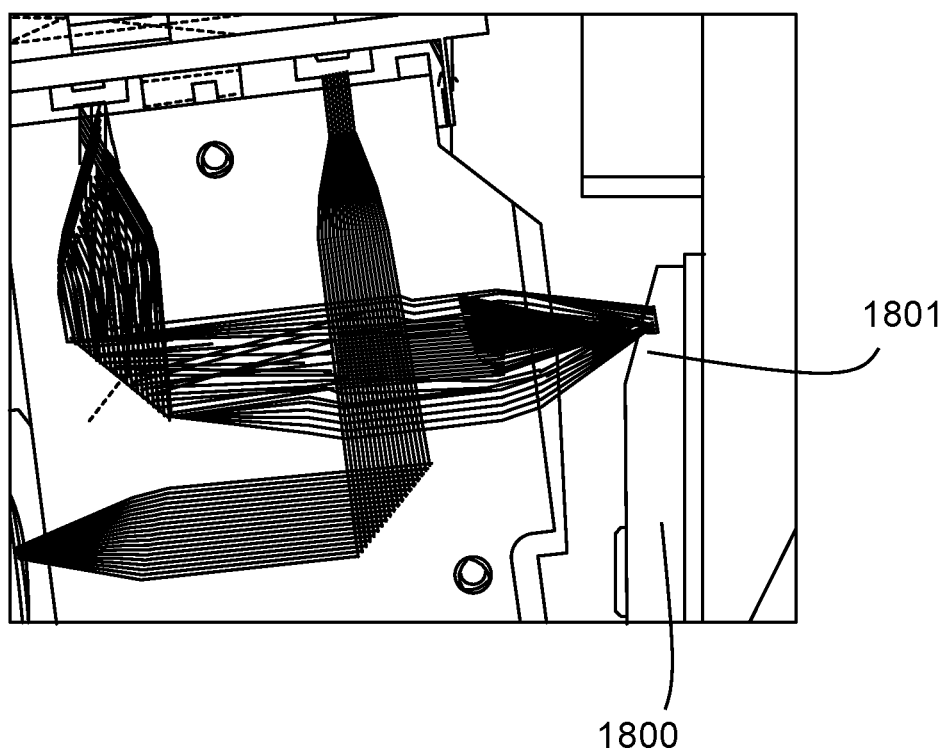
FIG. 18 provides a schematic representation of a dark target measurement according to an embodiment of the instant disclosure.

In some instances, the dark target may contain a specific angle or be mounted at a specific angle to further enhance a dark measurement by preventing stray light, including e.g., reflected light, from returning to the optics block during a dark target measurement. A specific embodiment of a dark target configuration is provided in FIG. 17 where the dark target is observed to have an upper edge configured to have an angle (1700). The effect of a dark target (1800) having an angled portion (1801) upon which the dark measurement is made is depicted in the light-path diagram of FIG. 18. Accordingly, the dark target surface from which a dark target measurement is made may, in some instances, not be perpendicular to the emission light directed at the dark target.

Conveyors and Moveable Components

Multi-reaction analysis devices of the instant disclosure include conveyors configured to scan an optical analysis unit past a plurality of reaction vessels. In certain embodiments a linear conveyer is paired with linearly arranged components, including linearly arranged reaction vessels, linearly arranged optical blocks, and the like. As described herein, in certain embodiments the reaction vessels may remain stationary and the optical analysis unit may travel past the reaction vessels, e.g., in a scanning or linearly traveling motion.

Figure 15:
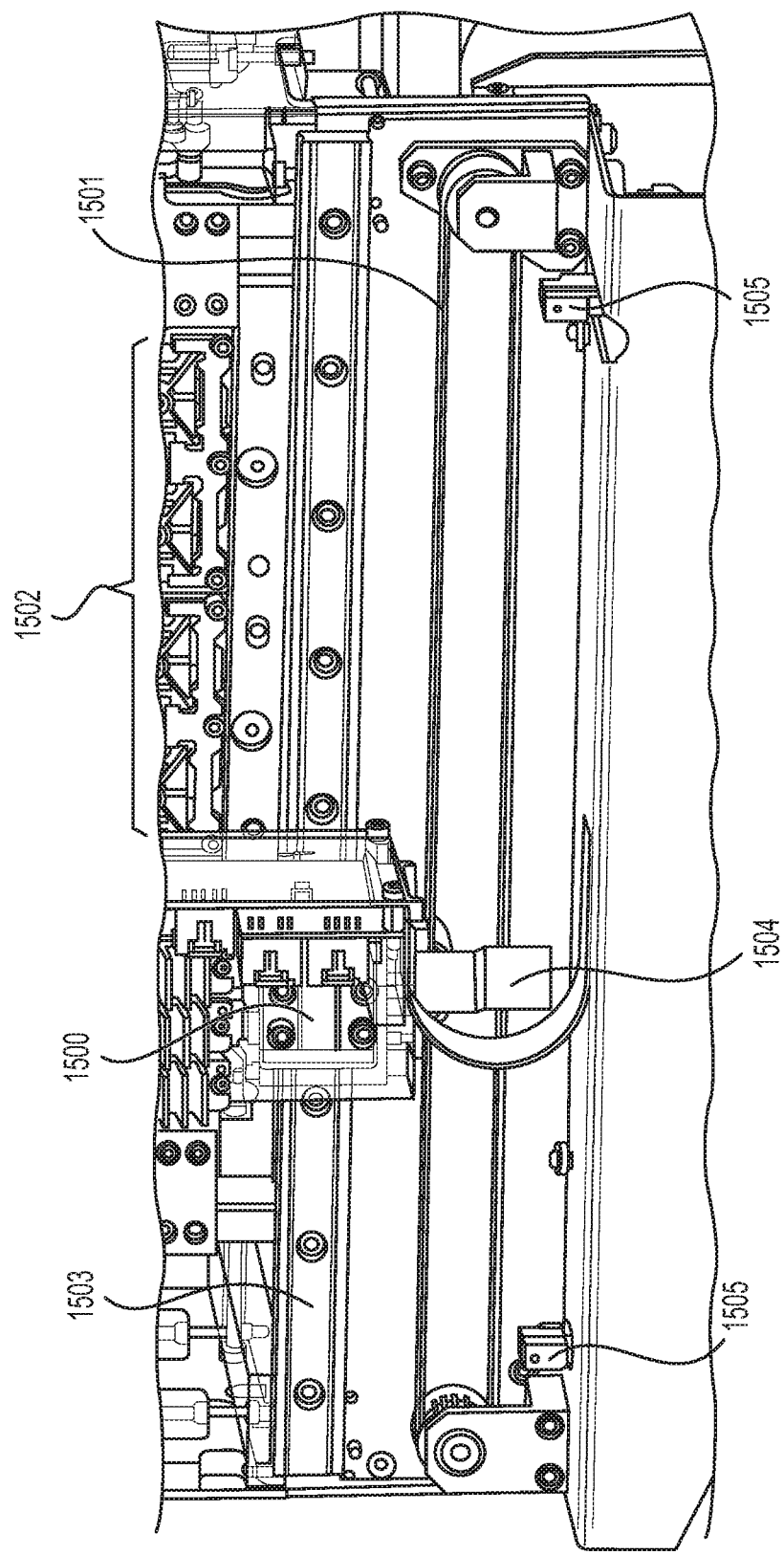
FIG. 15 depicts an embodiment of a linear conveyor as described herein.

For example, in one embodiment as depicted in FIG. 15, a traveling optical analysis unit (1500) having a plurality of linearly arranged optical blocks is attached a belt (1501) driven conveyor so as to scan a plurality of linearly arranged thermal blocks (1502) that contain linearly arranged reaction vessels. The optical analysis unit (1500) travels on a track (1503), and in some instances, may include one or more control and/or position monitoring elements including a flag (1504) and flag sensors (1505). Such flag and flag monitoring components provide a means of, e.g., during automation, providing a processor with the location of the optical analysis unit along the conveyor or generating other useful data including e.g., the speed of travel of the optical analysis device, etc.

Conveyor systems of the instant disclosure are not limited to belt driven systems, e.g., as depicted in FIG. 15, and may also include e.g., wheel/motor driven systems, actuator driven systems, piston driven systems, lead-screw systems, etc. Any convenient conveyor system may find use in the instant devices provided the conveyor system is capable of passing, e.g., linearly passing, an optical analysis unit past reaction vessels as described herein. In yet other embodiments, a traveling linearly arranged set of reaction vessels is passed, i.e., scanned, by a stationary optical analysis unit.

In certain embodiments, multi-reaction analysis systems may further include additional moveable components or moving elements. For example, in some instances a multi-reaction analysis system as described herein may include a reaction vessel clamping mechanism, a reaction vessel extraction mechanism, etc.

Figure 19:
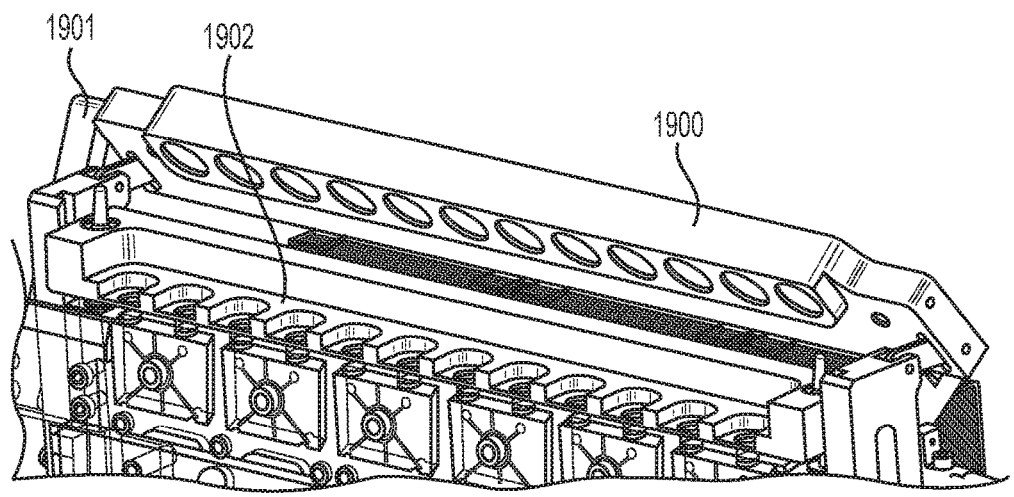
FIG. 19 depicts an embodiment of a reaction vessel clamping and extraction device as described herein.

One embodiment of a reaction vessel clamping and extraction mechanism includes but is not limited to that depicted in FIG. 19, where the top clamping bar (1900) is lifted and lowered through the use of a mechanical linkage (1901) to clamp and unclamp reaction vessels placed in the reaction vessel wells. The mechanism may further include a reaction vessel extraction bar (1902) that may be raised following completion of amplification and analysis of a set of samples to facilitate extraction of the reaction vessels from the reaction vessel wells. Any convenient mechanical linkages, and combinations thereof, for the clamping bar and/or the extraction bar may find use in reaction vessel clamping and/or reaction vessel extraction as described including but not limited to e.g., multi-bar linkages, lifter plates, actuators, cam arms, pistons, alignment pins, etc.

Clamping mechanisms may serve various purposes including but not limited to e.g., securing the reaction vessels against movement during various processes as described herein, shielding the reaction vessels from light, e.g., to promote accurate optical signal analysis, reducing thermal resistance between the reaction vessel and the reaction vessel well, and the like. Extraction mechanisms may serve various purposes including but not limited to e.g., removing reaction vessels from reaction vessel wells where thermal cycling causes the reaction vessels to adhere to the reaction vessel wells.

In one embodiment, the compressive force of the clamping mechanism is sufficient to reduce thermal interface resistance between the reaction vessel and the reaction vessel well. In some instances, sufficient compressive force reduces the thermal resistance to less than 5.0 watts per degree Celsius (W/° C.) including but not limited to e.g., less than 4.9 W/° C., less than 4.8 W/° C., less than 4.7 W/° C., less than 4.6 W/° C., less than 4.5 W/° C., less than 4.4 W/° C., less than 4.3 W/° C., less than 4.2 W/° C., less than 4.1 W/° C., less than 4.0 W/° C., less than 3.9 W/° C., less than 3.8 W/° C., etc., as measured using the Yovanovich Method of air interface. The compressive force sufficient to reduce the interface thermal resistance will vary and may range from less than 2 newtons (N) to more than 50 N including but not limited to e.g., 2 N to 50 N, 3 N to 50 N, 4 N to 50 N, 5 N to 50 N, 6 N to 50 N, 7 N to 50 N, 8 N to 50 N, 9 N to 50 N, 10 N to 50 N, 5 N to 45 N, 5 N to 40 N, 5 N to 35 N, 5 N to 30 N, 5 N to 25 N, 5 N to 20 N, 5 N to 15 N, 5 N to 10 N, 4 N to 45 N, 4 N to 40 N, 4 N to 35 N, 4 N to 30 N, 4 N to 25 N, 4 N to 20 N, 4 N to 15 N, 4 N to 10 N, 3 N to 45 N, 3 N to 40 N, 3 N to 35 N, 3 N to 30 N, 3 N to 25 N, 3 N to 20 N, 3 N to 15 N, 3 N to 10 N, etc. In some instances, the compressive force sufficient to reduce the interface thermal resistance to less than 5.0 W/° C. will vary and will range from less than 4 N to 20 N or more including but not limited to e.g., 4 N to 50 N, 5 N to 50 N, 6 N to 50 N, 7 N to 50 N, 8 N to 50 N, 9 N to 50 N, 10 N to 50 N, 5 N to 45 N, 5 N to 40 N, 5 N to 35 N, 5 N to 30 N, 5 N to 25 N, 5 N to 20 N, 5 N to 15 N, 5 N to 10 N, 4 N to 45 N, 4 N to 40 N, 4 N to 35 N, 4 N to 30 N, 4 N to 25 N, 4 N to 20 N, 4 N to 15 N, 4 N to 10 N, etc. Accordingly, the compressive force of a clamping mechanism will vary and may range from 2 N or less to 20 N or more including but not limited to e.g., 2 N or more, 3 N or more, 4 N or more, 5 N or more, 6 N or more, 7 N or more, 8 N or more, 9 N or more, 10 N or more, etc.

Clamping bar(s) of the instant disclosure may or may not be heated, e.g., electrically heated. For example, in some instances, the top clamp bar is heated. Such heating of clamp bars may serve various purposes including but not limited to e.g., to heat the reaction vessel cap and/or upper portion of the reaction vessel including but not limited to e.g., the assist in thermoregulation of the reaction vessel, to establish an even thermal gradient, to prevent condensation of reaction components on cool surfaces of the reaction vessel cap, to prevent condensation of reaction components on cool surfaces of the reaction vessel, and the like. In some instances, the system may not require such functions and, as such, the clamping bar(s) of the system may not be heated.

Signal Detection and Processing

Multi-reaction analysis devices of the instant disclosure include signal detection and signal and data processing units. For example, when emission light is passed back through an optical block as described herein, the emission light is directed to an optical detector configured to measure the emission light, e.g., measure the intensity of the emission light. In general, useful optical detectors for such purposed will, when light falls on the detector, convert the light into electrical current. Accordingly, useful optical detectors include photodiodes.

Photodiodes of signal detection devices as described herein may be dedicated to a particular light path or channel or wavelength or may be shared, e.g., shared between two or more wavelengths. Sharing of a photodiode of the instant disclosure may include one or more methods of reducing noise, e.g., cross-talk, as described herein, including but not limited to e.g., time division multiplexing, frequency division multiplexing, and the like. Photodiodes may be configured as part a circuit board, including but not limited where one or more photodiodes are operably attached to an optics circuit board or a detector circuit board.

Figure 20:
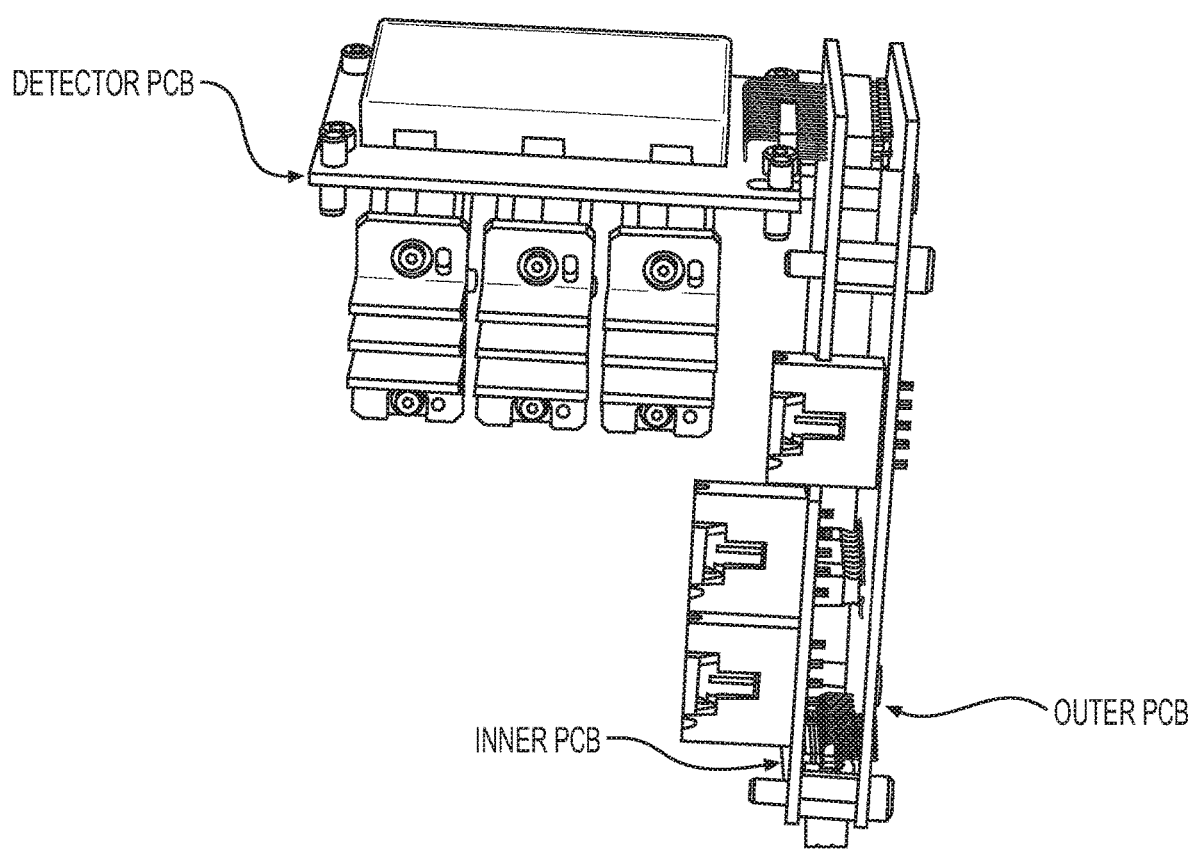
FIG. 20 depicts the circuit boards of an optics detection unit according to an embodiment of the instant disclosure.
Figure 21:
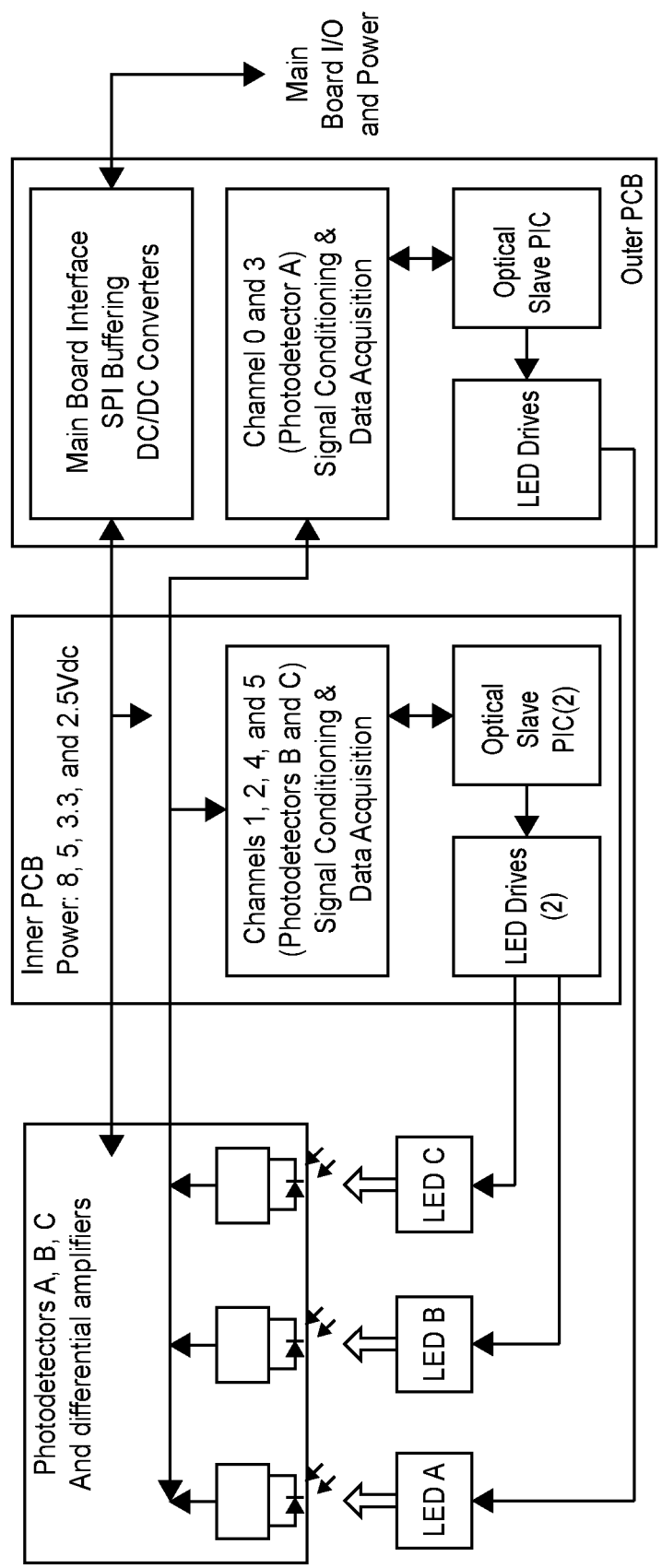
FIG. 21 provides a block diagram schematizing the communication between components of an embodiment of an optics detection unit as described here.

FIG. 20 provides a configuration of multi-reaction analysis device circuit boards, including a detection printed circuit board (PCB), an inner PCB and an outer PCB configured to attach to the components of a multi-reaction analysis device as described herein and provide the signal detection and processing functions of the above described methods. Such PCBs, in some instances, may be configured to perform one or more of the functions depicted in the block diagram of FIG. 21.

Signal processing functions including e.g., noise filtering, peak finding algorithms, and the like, may be performed with local circuitry including e.g., where such functions or portions thereof are performed on a local PCB including e.g., a PCB attached one or more components of a multi-reaction analysis unit as described herein. Alternatively, Signal processing functions including e.g., noise filtering, peak finding algorithms, and the like, may be performed by remote circuitry including e.g., where such functions or portions thereof are performed on a remote PCB or other signal processing circuitry. Signals may be transferred from local to remote circuitry through a variety of means including but not limited to e.g., wired connections, wireless connections, etc.

Integrated Systems

The instant disclosure includes integrated systems that make use of the devices described herein, including but not limited to integrated multi-reaction nucleic acid amplification and analysis systems. As applications of the described devices relate at least in part to real-time PCR, a method requiring the monitoring of an ongoing PCR reaction, integration of the described nucleic acid amplification devices and multi-reaction analysis devices may result, in many instances, in an integrated system for real-time PCR analysis.

Integrated systems will provide for the simultaneous functioning of both systems together where the systems are connected by a physical connection, electrical connection or both. For example, an integrated multi-reaction nucleic acid amplification and analysis system may include a nucleic acid amplification system physically mounted to a multi-reaction analysis unit as described herein. In other instances, an integrated multi-reaction nucleic acid amplification and analysis system may include a nucleic acid amplification system electrically connected (e.g., thought a wired connection) to a multi-reaction analysis unit as described herein. Physical and/or electrical connections in integrated systems promotes or allows for such devices to function together either through physical coordination and/or data or command transfer across devices.

The individual devices and components thereof may be reconfigured into integrated devices in various ways provided such reconfiguration does not render the element of the device or the overall system incapable of performing the functions described herein. In some instances, devices and systems, including integrated systems and methods as described herein may make use of a device or system or one or more components thereof as described in e.g., which claims priority to U.S. Ser. No. 62/308,617 and U.S. Ser. No. 62/357,772, the disclosures of which are incorporated herein by reference in their entireties. In some instances, devices and/or systems of the instant disclosure may be configured to be used in conjunction with or be connected to one or more sample preparation units as described in e.g., which claims priority to U.S. Ser. No. 62/308,618, the disclosures of which are incorporated herein by reference in their entireties.

Computer Related Embodiments

In some instances, the components of the systems as described herein may be connected by a wired data connection. Any suitable and appropriate wired data connection may find use in connecting the components of the described systems, e.g., as described herein, including but not limited to e.g., commercially available cables such as a USB cable, a coaxial cable, a serial cable, a C2G or Cat2 cable, a Cat5/Cat5e/Cat6/Cat6a cable, a Token Ring Cable (Cat4), a VGA cable, a HDMI cable, a RCA cable, an optical fiber cable, and the like. In some instances, e.g., where data security is less of a concern, wireless data connections may be employed including but not limited to e.g., radio frequency connections (e.g., PAN/LAN/MAN/WAN wireless networking, UHF radio connections, etc.), an infrared data transmission connection, wireless optical data connections, and the like.

The devices and systems of the instant disclosure may further include a "memory" that is capable of storing information such that it is accessible and retrievable at a later date by a computer. Any convenient data storage structure may be chosen, based on the means used to access the stored information. In certain aspects, the information may be stored in a "permanent memory" (i.e. memory that is not erased by termination of the electrical supply to a computer or processor) or "non-permanent memory". Computer hard-drive, CD-ROM, floppy disk, portable flash drive and DVD are all examples of permanent memory. Random Access Memory (RAM) is an example of non-permanent memory. A file in permanent memory may be editable and re-writable.

Substantially any circuitry can be configured to a functional arrangement within the devices and systems for performing the methods disclosed herein. The hardware architecture of such circuitry, including e.g., a specifically configured computer, is well known by a person skilled in the art, and can comprise hardware components including one or more processors (CPU), a random-access memory (RAM), a read-only memory (ROM), an internal or external data storage medium (e.g., hard disk drive). Such circuitry can also comprise one or more graphic boards for processing and outputting graphical information to display means. The above components can be suitably interconnected via a bus within the circuitry, e.g., inside a specific-use computer. The circuitry can further comprise suitable interfaces for communicating with general-purpose external components such as a monitor, keyboard, mouse, network, etc. In some embodiments, the circuitry can be capable of parallel processing or can be part of a network configured for parallel or distributive computing to increase the processing power for the present methods and programs. In some embodiments, the program code read out from the storage medium can be written into a memory provided in an expanded board inserted in the circuitry, or an expanded unit connected to the circuitry, and a CPU or the like provided in the expanded board or expanded unit can actually perform a part or all of the operations according to the instructions of the programming, so as to accomplish the functions described.

In addition to the components of the devices and systems of the instant disclosure, e.g., as described above, systems of the disclosure may include a number of additional components, such as data output devices, e.g., monitors and/or speakers, data input devices, e.g., interface ports, keyboards, etc., actuatable components, power sources, etc.

The instant disclosure includes computer readable medium, including non-transitory computer readable medium, which stores instructions for methods described herein. Aspects of the instant disclosure include computer readable medium storing instructions that, when executed by a computing device, cause the computing device to perform one or more steps of a method as described herein.

In certain embodiments, instructions in accordance with the methods described herein can be coded onto a computer-readable medium in the form of "programming", where the term "computer readable medium" as used herein refers to any storage or transmission medium that participates in providing instructions and/or data to a computer for execution and/or processing. Examples of storage media include a floppy disk, hard disk, optical disk, magneto-optical disk, CD-ROM, CD-R, magnetic tape, non-volatile memory card, ROM, DVD-ROM, Blue-ray disk, solid state disk, and network attached storage (NAS), whether or not such devices are internal or external to the computer. A file containing information can be "stored" on computer readable medium, where "storing" means recording information such that it is accessible and retrievable at a later date by a computer.

The computer-implemented method described herein can be executed using programming that can be written in one or more of any number of computer programming languages. Such languages include, for example, Java (Sun Microsystems, Inc., Santa Clara, CA) Visual Basic (Microsoft Corp., Redmond, WA), and C++ (AT&T Corp., Bedminster, NJ), as well as any many others.

Notwithstanding the appended claims, the disclosure is also defined by the following clauses:

1. A thermal block for simultaneous nucleic acid amplification and reaction analysis; the thermal block comprising:
   a) at least two reaction vessel wells, each well comprising:
      i) a top opening configured to receive a reaction vessel inserted vertically into the well;
      ii) a side aperture configured to allow light to pass laterally into the reaction vessel well, wherein upon insertion of a reaction vessel into the well a majority of the sidewall of the reaction vessel is in thermal contact with the well and a portion of the sidewall is exposed to light by the aperture;
   b) a thermal transfer surface opposite the side apertures of the two reaction vessel wells; and
   c) a mounting hole positioned between the two reaction vessel wells and having a center axis perpendicular to the plane of the thermal transfer surface.

2. The thermal block of clause 1, wherein the block is bilaterally symmetrical along a vertical axis.

3. The thermal block of any of clauses 1-2, wherein the thermal transfer surface is essentially flat.

4. The thermal block of any of clauses 1-3, wherein the mounting hole is positioned equidistant from the two reaction vessels.

5. The thermal block of clause 4, wherein the mounting hole is centrally positioned between the top and bottom sides of the thermal block.

6. The thermal block of clause 4, wherein the mounting hole is centrally positioned between the right and left sides of the thermal block.

7. The thermal block of any of clauses 1-6, wherein the top surface of the thermal block comprises a raised flange encircling the circumference of each of the two reaction vessel wells.

8. The thermal block of any of clauses 1-7, wherein the surface of the thermal block opposite the thermal surface comprises a plurality of raised ridges.

9. The thermal block of clause 8, wherein the plurality of raised ridges emanate radially from the mounting hole.

10. The thermal block of any of clauses 1-9, wherein the thermal block is constructed of aluminum.

11. The thermal block of any of clauses 1-10, wherein at least the two reaction vessel wells are nickel plated.

12. The thermal block of clause 11, wherein at least a portion of the thermal block other than the two reaction vessel wells is nickel plated.

13. The thermal block of clause 12, wherein the entire thermal block is nickel plated.

14. The thermal block of any of clauses 1-13, wherein the two reaction vessel wells comprise a lubrication coating.

15. The thermal block of clause 14, wherein the lubrication coating is a dry lubrication coating.

16. The thermal block of any of clauses 1-15, wherein the thermal block further comprises a temperature detection area configured for the functional attachment of a temperature detector positioned proximally to each reaction vessel well.

17. The thermal block of clause 16, wherein the temperature detection areas are positioned below the reaction vessel wells.

18. The thermal block of any of clauses 1-17, wherein each reaction vessel well further comprises a basal reservoir configured such that upon insertion of the reaction vessel into the well the reaction vessel does not contact the bottom of the well.

19. The thermal block of any of clauses 1-18, wherein the thermal block has a mass of 2 to 4 grams.

20. A nucleic acid amplification module, the module comprising:
  a) a thermoelectric cooler unit comprising a mounting hole;
  b) a thermal block of any of clauses 1-19, wherein the thermal transfer surface is in thermal contact with a first surface of the thermoelectric cooler unit; and
  c) a heatsink configured to receive a mechanical fastener, wherein the heatsink is in thermal contact with a second surface of the thermoelectric cooler unit and the mounting holes are aligned such that the thermal block, thermoelectric cooler unit, and the heatsink are joined by a mechanical fastener positioned through the mounting holes and affixed to the heatsink.

21. The module of clauses 20, further comprising a conductive pad between the thermal block and the thermoelectric cooler unit or between the thermoelectric cooler unit and the heatsink.

22. The module of clause 21, wherein the conductive pad is a graphite pad.

23. The module of any of clauses 20-22, wherein the module comprises conductive pads both between the thermal block and the thermoelectric cooler unit and between the thermoelectric cooler unit and the heatsink.

24. The module of any of clauses 20-23, wherein the mechanical fastener joins the thermal block, thermoelectric cooler unit, and the heatsink by a compression force.

25. The module of clause 24, wherein the mechanical fastener is a compression screw.

26. The module of any of clauses 24-25, wherein the compression force is between 100 and 200 pounds per square inch (psi).

27. The module of any of clauses 20-26, wherein the thermal block and the thermoelectric cooler are supported by a support bar fastened to the heatsink.

28. The module of any of clauses 20-27, wherein the module further comprises a heatsink fan configured to force air past the heatsink.

29. The module of clause 28, wherein the heatsink is joined to the heatsink fan by a duct.

30. The module of any of clauses 20-29, wherein the thermal block has an operating thermal slew rate of greater than 5° C. per second.

31. The module of any of clauses 20-30, wherein the module further comprises one or more resistance thermometers (RTDs) in thermal contact with the thermal block.

32. The module of clause 31, wherein the module comprises two RTDs in thermal contact with the thermal block, wherein each of the two RTDs are in proximity with a reaction vessel well of the thermal block.

33. The module of clauses 31 or 32, wherein the thermal contact between the one or more RTDs and the thermal block is maintained by a cantilever bar comprising one or more cantilever arms.

34. The module of any of clauses 20-33, wherein the module comprises an attached printed circuit board (PCB) for monitoring or controlling at least one electrical component of the module.

35. The module of clause 34, wherein the PCB is conformal coated.

36. The module of any of clauses 31-35, wherein the module comprises at least one RTD in thermal contact with the thermal block and electrically connected to the PCB.

37. The module of any of clauses 20-36, wherein the module comprises a RTD in thermal contact with the thermal block or the heatsink, wherein the RTD in thermal contact with the thermal block or the heatsink is configured to monitor the temperature of the thermal block or heatsink and trigger a cutoff of power to the thermal block or heatsink if the temperature indicates a thermal error condition.

38. The module of any of clauses 20 to 37, wherein the heatsink is configured to receive a second mechanical fastener and the nucleic acid amplification module further comprises a second thermal block in thermal contact with a second thermoelectric cooler unit in thermal contact with the heatsink, wherein the second thermal block, the second thermoelectric cooler unit and the heatsink are joined by a second mechanical fastener positioned through mounting holes in the second thermal block and the second thermoelectric cooler unit and affixed to the heatsink.

39. The module of clause 38, wherein the first thermal block and the second thermal block comprise separate electrical connections and are controlled independently.

40. The module of any of clauses 20-39, wherein the module further comprises one or more reaction vessel clamping bars.

41. The module of clause 40, wherein the one or more reaction vessel clamping bars provides a compression force on reaction vessels within the reaction vessel wells of 5 N or more.

42. A multi-reaction analysis module for the optical analysis of a plurality of amplification reaction vessels, the module comprising:
  a) an optics detection unit comprising an optical signal processor and a plurality of linearly arranged optical blocks, each optical block comprising:
    i) an illumination component configured to illuminate a reaction with excitation light;
    ii) a optics block aperture configured to pass excitation light to the reaction vessel and receive emission light from the reaction vessel;
    iii) a measurement channel configured to pass emission light to the optical signal processor; and
    iv) a reference channel configured to pass reference light to the optical signal processor;
  b) a linear conveyer configured to convey the optics detection unit linearly past each reaction vessel of the plurality of amplification reactions, wherein each optics block aperture of the plurality of linearly arranged optical blocks is optically exposed to the sidewall of each reaction vessel.

43. The module of clause 42, wherein the illumination component comprises one or more light emitting diode (LED) emitters.

44. The module of clause 43, wherein the illumination component comprises two or more light emitting diode (LED) emitters of different emission wavelengths.

45. The module of clauses 44, wherein the wavelengths of the two or more LED emitters are at least 50 nm apart.

46. The module of any of clauses 42-45, wherein the illumination component comprises frequency modulation.

47. The module of any of clauses 42-46, wherein the illumination component comprises time division modulation.

48. The module of any of clauses 42-47, wherein the optics detection unit comprises two or more optical blocks.

49. The module of clause 48, wherein the optics detection unit comprises three optical blocks.

50. An integrated multi-reaction nucleic acid amplification and analysis system, the system comprising:
  a) a nucleic acid amplification module of any of clauses 20-40; and
  b) a multi-reaction analysis module of any of clauses 41-48, wherein the spacing between the side apertures of the reaction vessel wells is unequal to the spacing between the optics block apertures of the optical blocks such that no more than one side aperture and one optics block aperture may be in alignment at any one time.

51. The system of clause 50, wherein the spacing between the side apertures is greater than the spacing between the optics block apertures.

52. The system of clause 50, wherein the spacing between the side apertures is less than the spacing between the optics block apertures.

53. The system of any of clauses 50-52, wherein the nucleic acid amplification module comprises two thermal blocks affixed to a single heatsink.

54. The system of any of clauses 50-53, wherein the multi-reaction analysis module comprises three optical blocks.

55. The system of any of clauses 50-54, wherein each illumination component comprises two or more LED emitters of differing wavelengths.

56. The system of clause 55, wherein the wavelengths of the two or more LED emitters are at least 50 nm apart.

57. An integrated multi-reaction nucleic acid amplification and analysis system, the system comprising:
  a) a multi-reaction nucleic acid amplification module comprising two or more thermal blocks comprising two or more linearly arranged and evenly spaced reaction vessel wells each having a side aperture configured to allow light to pass laterally into the reaction vessel well;
  b) a traveling optics detection unit comprising:
    i) an optical signal processor;
    ii) a plurality of linearly arranged even spaced optical blocks, each optical block comprising an illumination component and a optics block aperture configured to pass excitation light to a reaction vessel and receive emission light from the reaction vessel; and
    iii) a linear conveyer configured to convey the traveling optics detection unit linearly past the side aperture of each of the two or more reaction vessel wells,
  wherein the spacing between the side apertures of the reaction vessel wells is unequal to the spacing between the optics block apertures of the optical blocks such that no more than one side aperture and one optics blockaperture may be in alignment at any one time.

58. The system of clause 57, wherein the traveling optics detection unit comprises three optical blocks.

59. The system of any of clauses 57-58, wherein the illumination component comprises two or more LED emitters of differing wavelengths.

60. The system of clause 59, wherein the wavelengths of the two or more LED emitters are at least 50 nm apart.

61. A method of monitoring nucleic acid amplification in a plurality of amplification reaction vessels, the method comprising:
  a) linearly scanning a traveling optics detection unit having an excitation component and a plurality of optics block apertures past the plurality of amplification reaction vessels, wherein no more than one optics block aperture is in optical alignment with a amplification reaction vessel at any one time;
  b) receiving a scan signal from the optics detection unit comprising background noise and emission peaks;
  c) determining emission peaks within the background noise according to a plurality of reaction vessel windows;
  d) measuring an intensity value for each reaction vessel window to monitor the amplification in each reaction vessel of the plurality.

62. The method of clause 61, wherein the optics unit comprises a plurality of excitation components that are time modulated.

63. The method of any of clauses 61-62, wherein the optics unit comprises a plurality of excitation components that are frequency modulated.

64. The method of any of clauses 61-63, wherein each optics block aperture is part of an optics block and the method further comprises cross-talk subtraction.

65. The method of any of clauses 61-64, wherein the method further comprises one or more calibration measurement steps before or during the linearly scanning step.

66. The method of clause 65, wherein the one or more calibration measurement steps comprise aligning the plurality of optics block apertures with a dark target.

67. The method of clause 66, wherein the dark target comprises black polycarbonate.

68. The method of any of clauses 65-67, wherein the one or more calibration measurement steps comprises toggling the excitation component on or off.

69. The method of clauses 68, wherein the one or more calibration measurement steps comprises measuring a reference channel and adjusting the power supplied to the excitation component based on the measured reference channel.

70. The method of any of clauses 65-69, wherein at least one of the one or more calibration measurement steps is performed at least once per scan.

71. The method of any of clauses 65-70, wherein at least one of the one or more calibration measurement steps is performed at least twice per scan.

72. The method of any of clauses 65-71, wherein the measurement from the calibration measurement step is applied to a value obtained from the scan during a signal processing pathway.

Although the foregoing invention has been described in some detail by way of illustration and example for purposes of clarity of understanding, it is readily apparent to those of ordinary skill in the art in light of the teachings of this invention that certain changes and modifications may be made thereto without departing from the spirit or scope of the appended claims.

Accordingly, the preceding merely illustrates the principles of the invention. It will be appreciated that those skilled in the art will be able to devise various arrangements which, although not explicitly described or shown herein, embody the principles of the invention and are included within its spirit and scope. Furthermore, all examples and conditional language recited herein are principally intended to aid the reader in understanding the principles of the invention and the concepts contributed by the inventors to furthering the art, and are to be construed as being without limitation to such specifically recited examples and conditions. Moreover, all statements herein reciting principles, aspects, and embodiments of the invention as well as specific examples thereof, are intended to encompass both structural and functional equivalents thereof. Additionally, it is intended that such equivalents include both currently known equivalents and equivalents developed in the future, i.e., any elements developed that perform the same function, regardless of structure. The scope of the present invention, therefore, is not intended to be limited to the exemplary embodiments shown and described herein. Rather, the scope and spirit of present invention is embodied by the appended claims.

What is claimed is:

1. A method of monitoring nucleic acid amplification in a plurality of amplification reaction vessels, the method comprising:
   a) scanning the plurality of amplification reaction vessels with a traveling optics detection unit having an excitation component and a plurality of optics block apertures, wherein the spacing between amplification reaction vessels is unequal to the spacing between the optics block apertures and only one of the plurality of optics block apertures optically aligns with one of the plurality of amplification reaction vessels;
   b) receiving a scan signal from the optics detection unit comprising background noise and emission peaks;
   c) determining emission peaks within the background noise according to a plurality of reaction vessel windows;
   d) measuring an intensity value for each reaction vessel window to monitor the amplification in each reaction vessel of the plurality.

2. The method of claim 1, wherein the optics unit comprises a plurality of excitation components that are time modulated.

3. The method of claim 1, wherein the optics unit comprises a plurality of excitation components that are frequency modulated.

4. The method of claim 1, wherein each optics block aperture is part of an optics block and the method further comprises cross-talk subtraction.

5. The method of claim 1, wherein the method further comprises one or more calibration measurement steps before or during scanning the plurality of amplification reaction vessels.

6. The method of claim 5, wherein the one or more calibration measurement steps comprise aligning the plurality of optics block apertures with a dark target.

7. The method of claim 6, wherein the dark target comprises black polycarbonate.

8. The method of claim 5, wherein the one or more calibration measurement steps comprises toggling the excitation component on or off.

9. The method of claim 8, wherein the one or more calibration measurement steps comprises measuring a reference channel and adjusting the power supplied to the excitation component based on the measured reference channel.

10. The method of claim 5, wherein at least one of the one or more calibration measurement steps is performed at least once per scan.

11. The method of claim 5, wherein at least one of the one or more calibration measurement steps is performed at least twice per scan.

12. The method of claim 5, wherein the measurement from the calibration measurement step is applied to a value obtained from the scan during a signal processing pathway.

13. The method of claim 1, wherein the amplification reaction vessels comprise side-apertures that align with the optics block apertures.

14. The method of claim 1, wherein the plurality of amplification reaction vessels is linearly aligned and the traveling optics detection unit passes all the amplification reaction vessels of the plurality in a linear scanning.

15. The method of claim 1, wherein an optics block and an amplification reaction vessel are at an angle that decreases introduction of noise into the scan signal.

16. The method of claim 15, wherein the amplification reaction vessel is essentially vertical and the optics block is at some angle away from horizontal such that the optics block aperture is angled up from horizontal towards the amplification reaction vessel.

17. The method of claim 1, comprising collecting a scan signal during scanning the plurality of amplification reaction vessels only when an optics block aperture is aligned with an amplification reaction vessel.

* * * * *